US009884112B2

(12) United States Patent
Zepp et al.

(10) Patent No.: US 9,884,112 B2
(45) Date of Patent: *Feb. 6, 2018

(54) IMMUNOMODULATORY AGENT-POLYMERIC COMPOUNDS

(71) Applicant: Selecta Biosciences, Inc., Watertown, MA (US)

(72) Inventors: Charles Zepp, Hardwick, MA (US); Grayson B. Lipford, Watertown, MA (US); Yun Gao, Southborough, MA (US); Lloyd Johnston, Belmont, MA (US); Fen-ni Fu, Northborough, MA (US); Mark J. Keegan, Groton, MA (US); Sam Baldwin, Westford, MA (US)

(73) Assignee: Selecta Biosciences, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/658,040

(22) Filed: Mar. 13, 2015

(65) Prior Publication Data

US 2015/0328300 A1 Nov. 19, 2015

Related U.S. Application Data

(63) Continuation of application No. 14/138,601, filed on Dec. 23, 2013, now Pat. No. 9,006,254, which is a continuation of application No. 12/788,266, filed on May 26, 2010, now Pat. No. 8,629,151.

(60) Provisional application No. 61/217,129, filed on May 27, 2009, provisional application No. 61/217,117, filed on May 27, 2009, provisional application No.
(Continued)

(51) Int. Cl.
| A61K 39/385 | (2006.01) |
| C07D 473/34 | (2006.01) |
| C07D 471/04 | (2006.01) |
| C08J 3/24 | (2006.01) |
| A61K 9/51 | (2006.01) |
| B82Y 5/00 | (2011.01) |
| C08G 63/08 | (2006.01) |
| C08G 63/91 | (2006.01) |
| C08G 64/42 | (2006.01) |
| A61K 39/39 | (2006.01) |
| C08G 63/06 | (2006.01) |
| A61K 47/60 | (2017.01) |
| A61K 47/58 | (2017.01) |
| A61K 47/59 | (2017.01) |
| A61K 47/64 | (2017.01) |
| A61K 47/69 | (2017.01) |
| A61K 39/00 | (2006.01) |

(52) U.S. Cl.
CPC .......... *A61K 39/385* (2013.01); *A61K 9/5138* (2013.01); *A61K 39/0013* (2013.01); *A61K 39/39* (2013.01); *A61K 47/58* (2017.08); *A61K 47/59* (2017.08); *A61K 47/593* (2017.08); *A61K 47/60* (2017.08); *A61K 47/64* (2017.08); *A61K 47/6925* (2017.08); *A61K 47/6935* (2017.08); *A61K 47/6937* (2017.08); *B82Y 5/00* (2013.01); *C07D 471/04* (2013.01); *C07D 473/34* (2013.01); *C08G 63/06* (2013.01); *C08G 63/08* (2013.01); *C08G 63/912* (2013.01); *C08G 64/42* (2013.01); *C08J 3/24* (2013.01); *A61K 2039/55511* (2013.01); *A61K 2039/55544* (2013.01); *A61K 2039/55555* (2013.01); *A61K 2039/55561* (2013.01); *A61K 2039/6093* (2013.01); *A61K 2039/62* (2013.01); *A61K 2039/627* (2013.01); *C08J 2367/04* (2013.01)

(58) Field of Classification Search
CPC .. A61K 39/0013; A61K 39/385; A61K 39/39; A61K 47/482; A61K 47/48207; A61K 47/48238; A61K 47/48907; A61K 47/48192; A61K 47/48246; A61K 47/48869; A61K 47/48915; A61K 47/48176; A61K 47/48215; A61K 9/5138; A61K 2039/62; A61K 2039/627; A61K 2039/55511; A61K 2039/55544; A61K 2039/55555; A61K 2039/6093; A61K 2039/55561; C07D 473/34; C07D 471/04; C08J 3/24; C08J 2367/04; C08G 63/06; C08G 63/08; C08G 63/912; C08G 64/42; B82Y 5/00

See application file for complete search history.

(56) References Cited

U.S. PATENT DOCUMENTS

| 3,608,066 A | 9/1971 | Illartein |
| 4,009,257 A | 2/1977 | Thomas et al. |

(Continued)

FOREIGN PATENT DOCUMENTS

| CN | 1 692 943 A | 11/2005 |
| EP | 1 035 123 A1 | 9/2000 |

(Continued)

OTHER PUBLICATIONS

International Search Report and Written Opinion for PCT/US2010/001560 dated Apr. 14, 2011.

(Continued)

*Primary Examiner* — Robert Jones, Jr.
(74) *Attorney, Agent, or Firm* — Wolf, Greenfield & Sacks, P.C.

(57) ABSTRACT

This invention relates to compositions, and related compounds and methods, of conjugates of immunomodulatory agents and polymers or unit(s) thereof. The conjugates may be contained within synthetic nanocarriers, and the immu- (Continued)

nomodulatory agents may be released from the synthetic nanocarriers in a pH sensitive manner.

36 Claims, 5 Drawing Sheets

Related U.S. Application Data

61/217,124, filed on May 27, 2009, provisional application No. 61/217,116, filed on May 27, 2009.

(56) References Cited

U.S. PATENT DOCUMENTS

| | | |
|---|---|---|
| 4,021,364 A | 5/1977 | Speiser et al. |
| 4,225,581 A | 9/1980 | Kreuter et al. |
| 4,631,211 A | 12/1986 | Houghten |
| 4,756,907 A | 7/1988 | Beck et al. |
| 4,929,624 A | 5/1990 | Gerster et al. |
| 4,994,281 A | 2/1991 | Muranishi et al. |
| 5,114,703 A | 5/1992 | Wolf et al. |
| 5,118,528 A | 6/1992 | Fessi et al. |
| 5,213,812 A | 5/1993 | Jean-Marc |
| 5,229,490 A | 7/1993 | Tam |
| 5,500,161 A | 3/1996 | Andrianov et al. |
| 5,514,378 A | 5/1996 | Mikos et al. |
| 5,543,158 A | 8/1996 | Gref et al. |
| 5,565,215 A | 10/1996 | Ruxandra et al. |
| 5,578,325 A | 11/1996 | Domb et al. |
| 5,582,172 A | 12/1996 | Papisov et al. |
| 5,620,708 A | 4/1997 | Amkraut et al. |
| 5,656,298 A | 8/1997 | Kitchell et al. |
| 5,733,572 A | 3/1998 | Unger et al. |
| 5,733,925 A | 3/1998 | Kunz et al. |
| 5,762,904 A | 6/1998 | Okada et al. |
| 5,792,475 A | 8/1998 | Davis et al. |
| 5,837,752 A | 11/1998 | Shastri et al. |
| 5,869,103 A | 2/1999 | Yeh et al. |
| 5,871,747 A | 2/1999 | Gengoux-Sedlik |
| 5,912,017 A | 6/1999 | Mathiowitz et al. |
| 5,916,539 A | 6/1999 | Pilgrimm |
| 5,916,597 A | 6/1999 | Lee et al. |
| 5,928,647 A | 7/1999 | Rock |
| 5,977,089 A | 11/1999 | Arimilli et al. |
| 6,007,845 A | 12/1999 | Domb et al. |
| 6,060,082 A | 5/2000 | Chen et al. |
| 6,159,502 A | 12/2000 | Russell-Jones et al. |
| 6,197,229 B1 | 3/2001 | Ando et al. |
| 6,225,460 B1 | 5/2001 | Bischofberger et al. |
| 6,254,890 B1 | 7/2001 | Hirosue et al. |
| 6,288,040 B1 | 9/2001 | Muller et al. |
| 6,306,640 B1 | 10/2001 | Nicolette |
| 6,309,669 B1 | 10/2001 | Setterstrom et al. |
| 6,365,187 B2 | 4/2002 | Mathiowitz et al. |
| 6,387,397 B1 | 5/2002 | Chen et al. |
| 6,444,192 B1 | 9/2002 | Mattrey |
| 6,605,299 B2 | 8/2003 | Zalipsky |
| 6,632,671 B2 | 10/2003 | Unger |
| 6,635,283 B2 | 10/2003 | Edwards et al. |
| 6,723,429 B2 | 4/2004 | Bengs et al. |
| 6,767,702 B2 | 7/2004 | Mirkin et al. |
| 6,800,296 B1 | 10/2004 | Langer et al. |
| 6,815,170 B1 | 11/2004 | Morton |
| 6,849,270 B2 | 2/2005 | Zalipsky |
| 6,881,421 B1 | 4/2005 | Da Silveira et al. |
| 6,989,435 B2 | 1/2006 | Grainger et al. |
| 7,008,411 B1 | 3/2006 | Mandrusov et al. |
| 7,097,837 B2 | 8/2006 | Nielsen et al. |
| 7,129,222 B2 | 10/2006 | Van Nest et al. |
| 7,132,475 B2 | 11/2006 | Hubbell et al. |
| 7,238,368 B2 | 7/2007 | Zalipsky et al. |
| 7,238,711 B1 | 7/2007 | Grainger et al. |
| 7,250,403 B2 | 7/2007 | Van Nest et al. |
| 7,250,499 B2 | 7/2007 | Mirkin et al. |
| 7,285,289 B2 | 10/2007 | Nagy et al. |
| 7,375,234 B2 | 5/2008 | Sharpless et al. |
| 7,390,780 B2 | 6/2008 | Huang et al. |
| 7,501,134 B2 | 3/2009 | O'Hagan et al. |
| 7,517,520 B2 | 4/2009 | Manolova et al. |
| 7,550,441 B2 | 6/2009 | Farokhzad et al. |
| 7,727,969 B2 | 6/2010 | Farokhzad |
| 7,842,312 B2 | 11/2010 | Burgermeister et al. |
| 8,367,113 B2 | 2/2013 | Gu et al. |
| 8,629,151 B2 | 1/2014 | Zepp et al. |
| 8,652,487 B2 | 2/2014 | Maldonado et al. |
| 9,006,254 B2 | 4/2015 | Zepp et al. |
| 9,066,978 B2 | 6/2015 | Ilyinskii et al. |
| 9,265,815 B2 | 2/2016 | Fraser et al. |
| 9,289,476 B2 | 3/2016 | Fraser et al. |
| 9,289,477 B2 | 3/2016 | Fraser et al. |
| 9,295,718 B2 | 3/2016 | Fraser et al. |
| 2002/0055477 A1 | 5/2002 | Nest et al. |
| 2003/0009029 A1 | 1/2003 | Buchholz et al. |
| 2003/0035804 A1 | 2/2003 | D'Amico et al. |
| 2003/0108565 A1 | 6/2003 | Johnson et al. |
| 2003/0133988 A1 | 7/2003 | Fearon et al. |
| 2003/0138432 A1 | 7/2003 | Glazier |
| 2003/0165478 A1 | 9/2003 | Sokoll |
| 2003/0175950 A1 | 9/2003 | McSwiggen |
| 2003/0223938 A1 | 12/2003 | Nagy et al. |
| 2003/0232013 A1 | 12/2003 | Sieckman et al. |
| 2004/0022840 A1 | 2/2004 | Nagy et al. |
| 2004/0038406 A1 | 2/2004 | Unger et al. |
| 2004/0059094 A1 | 3/2004 | Bachmann et al. |
| 2004/0067503 A1 | 4/2004 | Tan et al. |
| 2004/0092470 A1 | 5/2004 | Leonard et al. |
| 2004/0142887 A1 | 7/2004 | Cui et al. |
| 2004/0156846 A1 | 8/2004 | Daum et al. |
| 2004/0191215 A1 | 9/2004 | Froix et al. |
| 2004/0192626 A1 | 9/2004 | McSwiggen et al. |
| 2004/0247680 A1 | 12/2004 | Farokhzad et al. |
| 2005/0020525 A1 | 1/2005 | McSwiggen et al. |
| 2005/0032733 A1 | 2/2005 | McSwiggen et al. |
| 2005/0037075 A1 | 2/2005 | Farokhzad et al. |
| 2005/0042298 A1 | 2/2005 | Pardridge et al. |
| 2005/0048063 A1 | 3/2005 | Ruoslahti et al. |
| 2005/0074812 A1 | 4/2005 | Ruoslahti et al. |
| 2005/0107322 A1 | 5/2005 | O'Hagan et al. |
| 2005/0113697 A1 | 5/2005 | Ottononi et al. |
| 2005/0158390 A1 | 7/2005 | Rana et al. |
| 2005/0163745 A1 | 7/2005 | Sokoll et al. |
| 2005/0191294 A1 | 9/2005 | Arap et al. |
| 2005/0233948 A1 | 10/2005 | D'Amico et al. |
| 2005/0244504 A1 | 11/2005 | Little et al. |
| 2005/0276850 A1 | 12/2005 | Podhipleux et al. |
| 2006/0002852 A1 | 1/2006 | Saltzman et al. |
| 2006/0002995 A1 | 1/2006 | Harwigsson |
| 2006/0051317 A1 | 3/2006 | Batrakova et al. |
| 2006/0073114 A1 | 4/2006 | Grainger et al. |
| 2006/0111271 A1 | 5/2006 | Cerny et al. |
| 2006/0017339 A1 | 8/2006 | Tornes et al. |
| 2006/0173339 A1 | 8/2006 | Tornes et al. |
| 2006/0189554 A1 | 8/2006 | Mumper et al. |
| 2006/0257359 A1 | 11/2006 | Francois et al. |
| 2007/0014804 A1 | 1/2007 | Burkhard |
| 2007/0014807 A1 | 1/2007 | Maida, III |
| 2007/0087986 A1 | 4/2007 | Premack et al. |
| 2007/0098713 A1 | 5/2007 | Unger et al. |
| 2007/0116768 A1 | 5/2007 | Chorny et al. |
| 2007/0184068 A1 | 8/2007 | Renner et al. |
| 2008/0014144 A1 | 1/2008 | Saltzman et al. |
| 2008/0014281 A1 | 1/2008 | Shibata et al. |
| 2008/0031899 A1 | 2/2008 | Reddy et al. |
| 2008/0044484 A1 | 2/2008 | Minev |
| 2008/0081074 A1 | 4/2008 | Gu et al. |
| 2008/0145441 A1 | 6/2008 | Penades et al. |
| 2008/0160089 A1 | 7/2008 | Vitiello et al. |
| 2008/0171059 A1 | 7/2008 | Howland et al. |
| 2008/0213377 A1 | 9/2008 | Bhatia et al. |
| 2008/0233181 A1 | 9/2008 | Nagy et al. |
| 2008/0268063 A1 | 10/2008 | Jon et al. |
| 2008/0305161 A1 | 12/2008 | Shah et al. |
| 2008/0317784 A1 | 12/2008 | O'Hagan et al. |
| 2009/0004118 A1 | 1/2009 | Nie et al. |
| 2009/0028910 A1 | 1/2009 | DeSimone et al. |

(56) References Cited

U.S. PATENT DOCUMENTS

| | | |
|---|---|---|
| 2009/0053293 A1 | 2/2009 | Liang et al. |
| 2009/0074828 A1 | 3/2009 | Alexis et al. |
| 2009/0104268 A1 | 4/2009 | Himmler et al. |
| 2009/0169636 A1 | 7/2009 | O'Hagan et al. |
| 2009/0202571 A1 | 8/2009 | Davis et al. |
| 2009/0226525 A1 | 9/2009 | de los Rios et al. |
| 2009/0257950 A1 | 10/2009 | Sligar et al. |
| 2009/0297609 A1 | 12/2009 | Shoichet et al. |
| 2009/0297621 A1 | 12/2009 | Lim et al. |
| 2009/0298710 A1 | 12/2009 | Farokhzad et al. |
| 2009/0325292 A1 | 12/2009 | Baker et al. |
| 2010/0022680 A1 | 1/2010 | Karnik et al. |
| 2010/0055189 A1 | 3/2010 | Hubbell et al. |
| 2010/0062968 A1 | 3/2010 | Pulendran et al. |
| 2010/0068285 A1 | 3/2010 | Zale et al. |
| 2010/0069426 A1 | 3/2010 | Zale et al. |
| 2010/0075995 A1 | 3/2010 | Biggadike et al. |
| 2010/0092425 A1 | 4/2010 | Von Andrian et al. |
| 2010/0129392 A1 | 5/2010 | Shi et al. |
| 2010/0129439 A1 | 5/2010 | Alexis et al. |
| 2010/0144845 A1 | 6/2010 | Farokhzad et al. |
| 2010/0151000 A1 | 6/2010 | Thomas et al. |
| 2010/0160299 A1 | 6/2010 | Baker et al. |
| 2010/0172993 A1 | 7/2010 | Singh et al. |
| 2010/0183727 A1 | 7/2010 | Iannacone et al. |
| 2010/0196482 A1 | 8/2010 | Radovic-Moreno et al. |
| 2010/0203142 A1 | 8/2010 | Zhang et al. |
| 2010/0233251 A1 | 9/2010 | Von Andrian et al. |
| 2010/0266491 A1 | 10/2010 | Farokhzad et al. |
| 2010/0297233 A1 | 11/2010 | Moretti et al. |
| 2010/0303723 A1 | 12/2010 | Farokhzad et al. |
| 2010/0303850 A1 | 12/2010 | Lipford et al. |
| 2010/0323019 A1 | 12/2010 | Lim et al. |
| 2010/0323199 A1 | 12/2010 | Gu et al. |
| 2011/0008435 A1 | 1/2011 | Devane et al. |
| 2011/0020388 A1 | 1/2011 | Zepp et al. |
| 2011/0027217 A1 | 2/2011 | Zepp et al. |
| 2011/0052697 A1 | 3/2011 | Farokhzad et al. |
| 2011/0110965 A1 | 5/2011 | Fraser et al. |
| 2011/0151015 A1 | 6/2011 | Hubby et al. |
| 2011/0171248 A1 | 7/2011 | Pittet et al. |
| 2011/0223201 A1 | 9/2011 | Lipford et al. |
| 2011/0229556 A1 | 9/2011 | Irvine et al. |
| 2011/0262491 A1 | 10/2011 | Keegan et al. |
| 2011/0272836 A1 | 11/2011 | Keegan et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2011/0294717 A1 | 12/2011 | Ali et al. |
| 2012/0027806 A1 | 2/2012 | Ilyinskii et al. |
| 2012/0058153 A1 | 3/2012 | Ilyinskii et al. |
| 2012/0058154 A1 | 3/2012 | Ilyinskii et al. |
| 2012/0064110 A1 | 3/2012 | Ilyinskii et al. |
| 2012/0070493 A1 | 3/2012 | Fraser et al. |
| 2012/0114677 A1 | 5/2012 | Zepp et al. |
| 2012/0171229 A1 | 7/2012 | Zepp et al. |
| 2012/0244222 A1 | 9/2012 | Altreuter et al. |
| 2012/0276109 A1 | 11/2012 | Fraser et al. |
| 2012/0276133 A1 | 11/2012 | Maldonado et al. |
| 2012/0276134 A1 | 11/2012 | Fraser et al. |
| 2012/0276155 A1 | 11/2012 | Kishimoto et al. |
| 2012/0276156 A1 | 11/2012 | Fraser et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2013/0028857 A1 | 1/2013 | Gao et al. |
| 2013/0028941 A1 | 1/2013 | Altreuter et al. |
| 2013/0039954 A1 | 2/2013 | Pittet et al. |
| 2013/0058894 A1 | 3/2013 | Maldonado et al. |
| 2013/0058901 A1 | 3/2013 | Maldonado et al. |
| 2013/0058902 A1 | 3/2013 | Kishimoto et al. |
| 2013/0058963 A1 | 3/2013 | Maldonado et al. |
| 2013/0058970 A1 | 3/2013 | Kishimoto et al. |
| 2013/0058974 A1 | 3/2013 | Maldonado et al. |
| 2013/0058975 A1 | 3/2013 | Maldonado et al. |
| 2013/0058976 A1 | 3/2013 | Kishimoto et al. |
| 2013/0058977 A1 | 3/2013 | Maldonado et al. |
| 2013/0058978 A1 | 3/2013 | Maldonado et al. |
| 2013/0059009 A1 | 3/2013 | Kishimoto et al. |
| 2014/0030344 A1 | 1/2014 | Zepp et al. |
| 2014/0199340 A1 | 7/2014 | Maldonado |
| 2014/0242173 A1 | 8/2014 | Zepp et al. |
| 2014/0328854 A1 | 11/2014 | Maldonado et al. |
| 2014/0328921 A1 | 11/2014 | Maldonado |
| 2014/0328922 A1 | 11/2014 | Maldonado |
| 2014/0328923 A1 | 11/2014 | Maldonado et al. |
| 2014/0328924 A1 | 11/2014 | Kishimoto |
| 2014/0356361 A1 | 12/2014 | Maldonado et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328309 A1 | 11/2015 | Ilyinskii et al. |
| 2015/0328333 A1 | 11/2015 | Fraser et al. |
| 2015/0335762 A1 | 11/2015 | Fraser et al. |
| 2015/0359865 A1 | 12/2015 | Kishimoto |
| 2015/0374815 A1 | 12/2015 | Kishimoto et al. |
| 2016/0022650 A1 | 1/2016 | Fraser et al. |
| 2016/0030554 A1 | 2/2016 | Kishimoto et al. |
| 2016/0030555 A1 | 2/2016 | Kishimoto et al. |
| 2016/0067228 A1 | 3/2016 | Kishimoto et al. |
| 2016/0074372 A1 | 3/2016 | Kishimoto |
| 2016/0074427 A1 | 3/2016 | Kishimoto |
| 2016/0074531 A1 | 3/2016 | Kishimoto |
| 2016/0074532 A1 | 3/2016 | Kishimoto |
| 2016/0128986 A1 | 5/2016 | O'Neil et al. |
| 2016/0128987 A1 | 5/2016 | Griset et al. |
| 2016/0220501 A1 | 8/2016 | Fraser et al. |
| 2016/0243253 A1 | 8/2016 | Fraser et al. |
| 2016/0256401 A1 | 9/2016 | Fraser et al. |
| 2016/0279234 A1 | 9/2016 | Kishimoto et al. |

FOREIGN PATENT DOCUMENTS

| | | |
|---|---|---|
| EP | 1 752 141 A1 | 2/2007 |
| JP | 2007-532572 A | 11/2007 |
| JP | 2008-540558 A | 11/2008 |
| JP | 2012-525153 A | 10/2012 |
| WO | WO 95/22963 A1 | 8/1995 |
| WO | WO 96/20698 A2 | 7/1996 |
| WO | WO 97/004747 A1 | 2/1997 |
| WO | WO 99/28321 A1 | 6/1999 |
| WO | WO 00/06123 A1 | 2/2000 |
| WO | WO 00/027363 A1 | 5/2000 |
| WO | WO 2004/030608 A2 | 4/2004 |
| WO | WO 2004/071493 A1 | 8/2004 |
| WO | WO 2004/084871 A1 | 10/2004 |
| WO | WO 2004/098509 A2 | 11/2004 |
| WO | WO 2005/014110 A1 | 2/2005 |
| WO | WO 2005/046572 A2 | 5/2005 |
| WO | WO 2005/110013 A2 | 11/2005 |
| WO | WO 2005/120574 A1 | 12/2005 |
| WO | WO 2006/037979 A2 | 4/2006 |
| WO | WO 2006/066158 A2 | 6/2006 |
| WO | WO 2006/102395 A2 | 9/2006 |
| WO | WO 2006/117217 A2 | 11/2006 |
| WO | WO 2006/122223 A2 | 11/2006 |
| WO | WO 2006/137934 A2 | 12/2006 |
| WO | WO 2007/001448 A2 | 1/2007 |
| WO | WO 2007/003054 A1 | 1/2007 |
| WO | WO 2007/019678 A1 | 2/2007 |
| WO | WO 2007/068747 A1 | 6/2007 |
| WO | WO 2007/070682 A2 | 6/2007 |
| WO | WO 2007/089870 A2 | 8/2007 |
| WO | WO 2007/098254 A2 | 8/2007 |
| WO | WO 2007/118653 A2 | 10/2007 |
| WO | WO 2007/133807 A2 | 11/2007 |
| WO | WO 2007/137117 A2 | 11/2007 |
| WO | WO 2007/144150 A1 | 12/2007 |
| WO | WO 2007/150030 A2 | 12/2007 |

(56) References Cited

FOREIGN PATENT DOCUMENTS

| WO | WO 2008/019142 A2 | 2/2008 |
|---|---|---|
| WO | WO 2008/051245 A2 | 5/2008 |
| WO | WO 2008/071774 A1 | 6/2008 |
| WO | WO 2008/079924 A1 | 7/2008 |
| WO | WO 2008/105773 A2 | 9/2008 |
| WO | WO 2008/115319 A2 | 9/2008 |
| WO | WO 2008/115641 A2 | 9/2008 |
| WO | WO 2008/118861 A2 | 10/2008 |
| WO | WO 2008/121926 A1 | 10/2008 |
| WO | WO 2008/124632 A1 | 10/2008 |
| WO | WO 2008/124634 A1 | 10/2008 |
| WO | WO 2008/124639 A2 | 10/2008 |
| WO | WO 2008/127532 A1 | 10/2008 |
| WO | WO 2008/147456 A2 | 12/2008 |
| WO | WO 2009/038685 A1 | 3/2009 |
| WO | WO 2009/051837 A2 | 4/2009 |
| WO | WO 2009/076158 A1 | 6/2009 |
| WO | WO 2009/106999 A2 | 9/2009 |
| WO | WO 2009/109428 A2 | 9/2009 |
| WO | WO 2009/111588 A1 | 9/2009 |
| WO | WO 2010/003009 A2 | 1/2010 |
| WO | WO 2010/017330 A1 | 2/2010 |
| WO | WO 2010/018130 A1 | 2/2010 |
| WO | WO 2010/018131 A1 | 2/2010 |
| WO | WO 2010/018132 A1 | 2/2010 |
| WO | WO 2010/018133 A1 | 2/2010 |
| WO | WO 2010/025324 A2 | 3/2010 |
| WO | WO 2010/042863 A1 | 4/2010 |
| WO | WO 2010/042866 A1 | 4/2010 |
| WO | WO 2010/042870 A1 | 4/2010 |
| WO | WO 2010/042876 A1 | 4/2010 |
| WO | WO 2010/115046 A2 | 10/2010 |
| WO | WO 2010/123569 A2 | 10/2010 |
| WO | WO-2010/127228 A1 | 11/2010 |
| WO | WO 2010/138192 A2 | 12/2010 |
| WO | WO 2010/138193 A2 | 12/2010 |
| WO | WO 2010/138194 A2 | 12/2010 |
| WO | WO 2011/005850 A1 | 1/2011 |

OTHER PUBLICATIONS

International Preliminary Report on Patentability for PCT/US2010/001560 dated Dec. 8, 2011.
International Search Report and Written Opinion for PCT/US2010/001559 dated Apr. 14, 2011.
International Preliminary Report on Patentability for PCT/US2010/001559 dated Dec. 8, 2011.
International Search Report and Written Opinion for PCT/US2010/001561 dated Apr. 29, 2011.
International Preliminary Report on Patentability for PCT/US2010/001561 dated Dec. 8, 2011.
[No Author Listed] Nanoparticles As Drug Carriers. Ed, Vladimir Torchilin. Imperial College Press. 2006. 754 pages.
Aime et al., Lanthanide(III) chelates for NMR biomedical applications. Chemical Society Reviews. 1998;27:19-29.
Akaishi et al., Targeting chemotherapy using antibody-combined liposome against human pancreatic cancer cell-line. The Tohoku Journal of Experimental Medicine. 1994;175(1):29-42.
Alexis et al., Factors affecting the clearance and biodistribution of polymeric nanoparticles. Mol Pharm. Jul.-Aug. 2008;5(4):505-15. Epub Aug. 4, 2008.
Aliferis et al., Living polypeptides. Biomacromolecules. Sep.-Oct. 2004;5(5):1653-6.
Allen et al., Nano-engineering block copolymer aggregates for drug delivery. Colloids Surfaces B-Biointerfaces. 1999;16:3-27.
Allison, The mode of action of immunological adjuvants. Dev Biol Stand. 1998;92:3-11.
Amsberry et al., Amine prodrugs which utilize hydroxy amide lactonization. I. A potential redox-sensitive amide prodrug. Pharm Res. Mar. 1991;8(3):323-30.
Anderson et al., Delivery Systems for Immunomodulatory Proteins and Peptides. BioDrugs. Jan. 1997;7(1):51-65.

Anikeeva et al., Quantum dot/peptide-MHC biosensors reveal strong CD8-dependent cooperation between self and viral antigens that augment the T cell response. Proc Natl Acad Sci U S A. Nov. 7, 2006;103(45):16846-51. Epub Oct. 31, 2006.
Asano et al., Targeting activated lymphocytes with lipid microsphere containing a cytotoxic agent; efficacy of immunosuppression with a new drug delivery system. J Urology. 2001;165(5)384. Abstact 1571.
Astete et al., Synthesis and characterization of PLGA nanoparticles. J Biomat Sci. 2006;17:247-89.
Ataman-Onal et al., Surfactant-free anionic PLA nanoparticles coated with HIV-1 p24 protein induced enhanced cellular and humoral immune responses in various animal models. J Control Release. May 15, 2006;112(2):175-85. Epub Mar. 6, 2006.
Avgoustakis, Pegylated poly(lactide) and poly(lactide-co-glycolide) nanoparticles: preparation, properties and possible applications in drug delivery. Curr Drug Deliv. Oct. 2004;1(4):321-33.
Bae et al., Mixed polymeric micelles for combination cancer chemotherapy through the concurrent delivery of multiple chemotherapeutic agents. J Control Release. Oct. 8, 2007;122(3):324-30. Epub Jun. 13, 2007.
Bagalkot et al., An Aptamer-Doxorubicin Physical Conjugate as a Novel Targeted Drug-Delivery Platform. Angew Chem Int. 2006;45(48):8149-52.
Bala et al., PLGA nanoparticles in drug delivery: the state of the art. Crit Rev Ther Drug Carrier Syst. 2004;21(5):387-422.
Barichello et al., Encapsulation of hydrophilic and lipophilic drugs in PLGA nanoparticles by the nanoprecipitation method. Drug Dev Ind Pharm. Apr. 1999;25(4):471-6.
Beaurepaire et al., Functionalized Fluorescent Oxide Nanoparticles: Artificial Toxins for Sodium Channel Targeting and Imaging at the Single-Molecule Level. Nano Letters. 2004;4(11):2079-83.
Bharali, Micro-and Nanoparticles-Based Vaccines for Hepatitis B. Immune-Mediated Diseases. 2007:415-21.
Blanco-Prieto et al., Slow delivery of the selective cholecystokinin agonist pBC 264 into the rat nucleus accumbens using microspheres. J Neurochem. Dec. 1996;67(6):2417-24.
Borchardt et al., Stereopopulation control. 3. Facilitation of intramolecular conjugate addition of the carboxyl group. J Am Chem Soc. Dec. 27, 1972;94(26):9175-82.
Borges et al., Evaluation of the immune response following a short oral vaccination schedule with hepatitis B antigen encapsulated into alginate-coated chitosan nanoparticles. Eur J Pharm Sci. Dec. 2007;32(4-5):278-90. Epub Aug. 15, 2007.
Bourquin et al., Targeting CpG oligonucleotides to the lymph node by nanoparticles elicits efficient antitumoral immunity. J Immunol. Sep. 1, 2008;181(5):2990-8.
Boussif et al., A versatile vector for gene and oligonucleotide transfer into cells in culture and in vivo: polyethylenimine. Proc Natl Acad Sci. USA. 1995;92:7297-301.
Brito et al., Nanoparticulate carriers for the treatment of coronary restenosis. Int J Nanomedicine. 2007;2(2):143-61.
Bullis, Shape Matters for Nanoparticles. Technology Review. Aug. 7, 2008. 2 pages.
Bundy et al., *Escherichia coli*-based cell-free synthesis of virus-like particles. Biotechnol Bioeng. May 1, 2008;100(1):28-37.
Buter et al., Synthesis of Macrocyclic sulfides using cesium thiolates: 1,4,8,11-tetrathiacyclotetradecane. Organic Synthesis. 1993;8:592. 5 pages.
Cameron et al., Aliphatic polyester polymer stars: synthesis, properties and applications in biomedicine and nanotechnology. Chem Soc Rev. Mar. 2011;40(3):1761-76.
Carino et al., Nanosphere based oral insulin delivery. J Control Release. 2000;65(1-2):261-9.
Carpino et al., Reductive Lactonization of strategically methylated quinone propionic acid esters and amides. J Org Chem. 1989;54:3303-10.
Carrot et al., Two general methods for the synthesis of Thiol-Functional Polycaprolactones. Macromolecules. 1999;32:5264-9.
Cerritelli et al., PEG-SS-PPS: reduction-sensitive disulfide block copolymer vesicles for intracellular drug delivery. Biomacromolecules. Jun. 2007;8(6):1966-72. Epub May 12, 2007.

(56) References Cited

OTHER PUBLICATIONS

Chacón et al., Optimized preparation of poly D,L (lactic-glycolic) microspheres and nanoparticles for oral administration. Intl J Pharmaceutics. 1996;141:81-91.

Chan et al., Acid-cleavable polymeric core-shell particles for delivery of hydrophobic drugs. J Control Release. Oct. 10, 2006;115(2):197-207. Epub Jul. 29, 2006.

Chan et al., Preparation and characterization of immunogens for antibody production against metanephrine and normetanephrine. J Immunol Methods. Aug. 1, 2002;266(1-2):143-54.

Cheng et al., Formulation of functionalized PLGA-PEG nanoparticles for in vivo targeted drug delivery. Biomaterials. 2007;28(5):869-76.

Chinen et al., Basic and clinical immunology. J Allergy Clin Immunol. Aug. 2005;116(2):411-8.

Chu et al., Aptamer mediated siRNA delivery. Nuc Acid Res. 2006;34:e73.

Chu et al., Labeling tumor cells with fluorescent nanocrystal-aptamer bioconjugates. Biosens Bioelectron. 2006;21:1859-66.

Chukwu et al., Loading some psychopharmacologic agents onto poly(butylcynoacrylate) nanoparticles—a means for targeting agents to the brain and improving therapeutic efficiency. Proc Int'l Symp Control Rel Bioact Mat. 1999:1148-9.

Conti et al., Thymopentin loaded microsphere preparation by w/o/w emulsion technique: in vitro/ex vivo evaluation. J Microencapsul. May-Jun. 1997;14(3):303-10.

Croy et al., Polymeric micells for drug delivery. Curr Pharm Design. 2006;12:4669-84.

Cruz et al., The influence of PEG chain length and targeting moiety on antibody-mediated delivery of nanoparticle vaccines to human dendritic cells. Biomaterials. Oct. 2011;32(28):6791-803. Epub Jul. 2, 2011. E-pub version.

De Jaeghere et al., Freeze-drying and lyopreservation of diblock and triblock poly(lactic acid)-poly(ethylene oxide) (PLA-PEO) copolymer nanoparticles. Pharm Dev Technol. 2000;5(4):473-83.

De La Fuente et al., Novel hyaluronan-based nanocarriers for transmucosal delivery of macromolecules. Macromol Biosci. May 13, 2008;8(5):441-50.

Delemarre et al., Repopulation of macrophages in popliteal lymph nodes of mice after liposome-mediated depletion. J Leukoc Biol. 1990;47(3):251-7.

Demello et al., Microscale reactors: nanoscale products. Lab on a Chip. 2004;4(2):11N-15N.

Demello, Control and detection of chemical reactions in microfluidic systems. Nature. 2006;442(7100:394-402.

Deming, Facile synthesis of block copolypeptides of defined architecture. Nature. 1997;390(6658):386-9.

Derfus et al., Intracellular Delivery of Quantum Dots for Live Cell Labeling and Organelle Tracking. Adv Mat. 2004;16:961-6.

Diwan et al., Enhancement of immune responses by co-delivery of a CpG oligodeoxynucleotide and tetanus toxoid in biodegradable nanospheres. J Control Release. Dec. 13, 2002;85(1-3):247-62.

Donbrow, Ed., Microcapsules and Nanoparticles in Medicine and Pharmacy. CRC Press, Boca Raton, 1992.

Dou et al.,Development of a macrophage-based nanoparticle platform for antiretroviral drug delivery. Blood. Oct. 15, 2006;108(8):2827-35. Epub Jun. 29, 2006. Erratum in: Blood. Mar. 1, 2007;109(5):1816.

Elamanchili et al., "Pathogen-mimicking" nanoparticles for vaccine delivery to dendritic cells. J Immunother. May-Jun. 2007;30(4):378-95. Abstract only.

Eldridge et al., Biodegradable microspheres as a vaccine delivery system. Mol Immunol. 1991;28(3):287-94.

Farokhzad et al., Drug delivery systems in urology—getting "smarter". Urology. Sep. 2006;68(3):463-9.

Farokhzad et al., Impact of nanotechnology on drug delivery. ACS Nano. Jan. 27, 2009;3(1):16-20.

Farokhzad et al., Nanoparticle—aptamer bioconjugates for cancer targeting. Expert Opin Drug Deliv. 2006;3(3):311-24.

Farokhzad et al., Nanoparticle-Aptamer Bioconjugates: A New Approach for Targeting Prostate Cancer Cells. Cancer Research. 2004,64:7668-72.

Farokhzad et al., Targeted nanoparticle-aptamer bioconjugates for cancer chemotherapy in vivo. Proc Natl Acad Sci USA. 2006;103(16):6315-20.

Fife et al., Highly Efficient intramolecular nucleophilic reactions. The cyclization of p-nitrophenyl N-(2-mercaptophenyl)-N-methylcarbamate and phenyl N-(2-Aminophenyl)-N-methylcarbamate. JACS. 1975;97:5878-82.

Fonseca et al., Paclitaxel-loaded PLGA nanoparticles: preparation, physicochemical characterization and in vitro anti-tumoral activity. J Control Release. 2002;83(2):273-86.

Forslund et al., Nitric oxide-releasing particles inhibit phagocytosis in human neutrophils. Biochem Biophys Res Commun. Apr. 17, 1997;233(2):492-5.

Fukuyama et al., 2,4 Dinitrobenzenesulfonamides: A Simple and Practical Method for the Preparation of a Variety of Secondary Amines and Diamines. Tetrahedron Letters. 1997;38(33):5831-4.

Gant et al., Semiquinone anion radicals formed by the reaction of quinones with glutathione or amino acids. FEBS Lett. Jun. 9, 1986;201(2):296-300.

Gao et al., In vivo cancer targeting and imaging with semiconductor quantum dots. Nat Biotechnol. 2004;22(8):969-76.

Gao et al., In vivo molecular and cellular imaging with quantum dots. Curr Op Biotechnol. 2005;16:63-72.

Gelperina et al., The potential advantages of nanoparticle drug delivery systems in chemotherapy of tuberculosis. Am J Respir Crit Care Med. Dec. 15, 2005;172(12):1487-90. Epub Sep. 8, 2005.

Gerster et al., Synthesis and structure-activity-relationships of 1H-imidazo[4,5-c]quinolines that induce interferon production. J Med Chem. May 19, 2005;48(10):3481-91.

Goh et al., Cross-linked microparticles as carriers for the delivery of plasmid DNA for vaccine development. Bioconjug Chem. May-Jun. 2004;15(3):467-74.

Gomes et al., Cyclization-activated prodrugs. Molecules. Nov. 12, 2007;12(11):2484-506.

Goudas et al., Chapter 40: Prolonged Release of Hydromorphone from a Novel Poly(Lactic-co-Glycolic) Acid Depot System—Initial In Vitro and In Vivo Observations. Handbook of Pharmaceutical Controlled Release Technology. Ed. Wise. 2000;837-8.

Govender et al., PLGA nanoparticles prepared by nanoprecipitation: drug loading and release studies of a water soluble drug. J Control Release. Feb. 1, 1999;57(2):171-85.

Greenwald et al., Drug delivery systems based on trimethyl lock lactonization: poly(ethylene glycol) prodrugs of amino-containing compounds. J Med Chem. Feb. 10, 2000;43(3):475-87.

Gref et al., Biodegradable long-circulating polymeric nanospheres. Science. 1994;263(5153):1600-3.

Griset et al., Expansile nanoparticles: synthesis, characterization, and in vivo efficacy of an acidresponsive polymeric drug delivery system. J Am Chem Soc. Feb. 25, 2009;131(7):2469-71. Epub Jan. 30, 2009.

Griset, Dissertation entitled: Delivery of Paclitaxel via pH-Responsive Polymeric Nanoparticles for Prevention of Lung Cancer and Mesothelioma Recurrence, Ohio State University, 2003.

Gu et al., Precise engineering of targeted nanoparticles by using self-assembled biointegrated block copolymers. Proc Natl Acad Sci U S A. Feb. 19, 2008;105(7):2586-91. Epub Feb. 13, 2008.

Gvili et al., PLGA nanoparticles for DNA vaccination—waiving complexity and increasing efficiency. Molc Ther. 2006;13:S209.

Haddadi, Delivery of rapamycin by PLGA nanoparticles enhances its suppressive activity ondendritic cells. J Biomed Mat Res A. 2007;84A(4):885-98.

Haensler et al., Polyamidoamine cascade polymers mediate efficient transfection of cells in culture. Bioconjugate Chem. 1993;4(5):372-9.

Haining et al., pH-triggered microparticles for peptide vaccination. J Immunol. Aug. 15, 2004;173(4):2578-85.

Hamdy et al., Co-delivery of cancer-associated antigen and Toll-like receptor 4 ligand in PLGA nanoparticles induces potent CD8+ T cell-mediated anti-tumor immunity. Vaccine. Sep. 15, 2008;26(39):5046-57. Epub Aug. 3, 2008.

(56) References Cited

OTHER PUBLICATIONS

Hamdy et al., Pharmaceutical analysis of synthetic lipid A-based vaccine adjuvants in poly (D,L-lactic-co-glycolic acid) nanoparticle formulations. J Pharm Biomed Anal. Aug. 15, 2007;44(4):914-23. Epub Mar. 19, 2007.

Hammerbeck et al., Administration of a dual toll-like receptor 7 and toll-like receptor 8 agonist protects against influenza in rats. Antiviral Res. Jan. 2007;73(1):1-11. Epub Aug. 18, 2006.

Hanes et al., Polymer microspheres for vaccine delivery. Pharm Biotechnol. 1995;6:389-412.

Hangartner et al., Antiviral immune responses in gene-targeted mice expressing the immunoglobulin heavy chain of virus-neutralizing antibodies. Proc Natl Acad Sci USA. 2003;100:12883-88.

Harada et al., Supramolecular assemblies of block copolymers in aqueous media as nanocontainers relevant to biological applications. Progress Polymer Sci. 2006;31(11):949-82.

Harper et al., Efficacy of a bivalent Li virus-like particle vaccine in prevention of infection with human papillomavirus types 16 and 18 in young women: a randomised controlled trial. Lancet. 2004;364(9447):1757-65.

Hermanson, Bioconjugate Techniques 2nd Edition. Academic Press. 2008. 1233 pages.

Hood et al., Tumor regression by targeted gene delivery to the neovasculature. Science. Jun. 28, 2002;296(5577):2404-7.

Hruby et al., Poly (ethylene oxide)-coated polymide nanoparticles deradable by glutathione. Colloid Polym Sci. 2007;285:569-74.

Hutchins et al., Facile intramolecular nucleophilic attack by alkoxide ions on ethyl and p-nitrophenyl carbamates. J Am Chem Soc. May 30, 1973;95(11):3786-90.

Hutchins et al., Fast Intramolecular Nucleophilic attack by phenoxide ion on carbamate ester groups. JACS. 1973;95:2282-6.

Johnson et al., Mechanism for rapid self-assembly of block copolymer nanoparticles. Phys Rev Lett. 2003;91(11):118302.1-4.

Jones et al., Polymeric micelles—a new generation of colloidal drug carriers. Eur J Pharm Biopharm. Sep. 1999;48(2):101-11.

Jung et al., Tetanus Toxoid Loaded Nanoparticles from Sulfobutylated Poly(Vinyl Alcohol)-Graft-Poly(Lactide-co-Glycolide): Evaluation of Antibody Response After Oral and Nasal Application in Mice. Pharm Res. 2001;18(3):352-60.

Junt et al., Subcapsular sinus macrophages in lymph nodes clear lymph-borne viruses and present them to antiviral B cells. Nature. 2007;450:110-4. Supplemental material.

Kabanov et al., DNA Complexes with Polycations for the Delivery of Genetic Material into Cells. Bioconjugate Chem. 1995;6(1):7-20.

Kamber et al., Organocatalytic ring-opening polymerization. Chem Rev. Dec. 2007;107(12):5813-40. Epub Nov. 8, 2007.

Kamentsky, Laser scanning cytometry. Methods Cell Biol. 2001;63:51-87.

Kanchan et al., Interactions of antigen-loaded polylactide particles with macrophages and their correlation with the immune response. Biomaterials. Dec. 2007;28(35):5344-57. Epub Sep. 7, 2007.

Karrer et al., On the key role of secondary lymphoid organs in antiviral immune responses studied in alymphoplastic (aly/aly) and spleenless (Hox11(-)/-) mutant mice. J Exp Med. 1997;185(12):2157-70.

Kelly et al., The Optical Properties of Metal Nanoparticles: The Influence of Size, Shape, and Dielectric Environment. J Phys Chem B. 2003;107(3):668-77.

King et al., Stereopopulation Control. 7. Rate Enhancement in the Lactonization of 3-(o-Hydroxyphenyl) propionic Acids: Dependence on the Size of Aromatic Ring Substituents. J Am Chem Soc. 1983;105:2752-60.

Konan et al., Preparation and characterization of sterile sub-200 nm meso-tetra(4-hydroxylphenyl)porphyrin-loaded nanoparticles for photodynamic therapy. Eur J Pharm Biopharm. Jan. 2003;55(1):115-24.

Kukowska-Latallo et al., Efficient transfer of genetic material into mammalian cells using Starburst polyamidoarnine dendrimers. Proc Natl Acad Sci USA. 1996;93(10):4897-902.

Kwon et al., Enhanced antigen presentation and immunostimulation of dendritic cells using acid-degradable cationic nanoparticles. J Control Release. Jul. 20, 2005;105(3):199-212.

Kwon et al., In vivo targeting of dendritic cells for activation of cellular immunity using vaccine carriers based on pH-responsive microparticles. Proc Natl Acad Sci U S A. Dec. 20, 2005;102(51):18264-8. Epub Dec. 12, 2005.

Kwon et al., Pseudopoly(amino acids): A study of the synthesis and characterization of poly(acyl-hydroxyproline-esters). Macromolecules. 1989;22:3250-5.

Labhasetwar et al., Arterial uptake of biodegradable nanoparticles: Effect of surface modifications. J Pharm Sci. 1998;87(10):1229-34.

Lamalle-Bernard et al., Coadsorption of HIV-1 p24 and gp120 proteins to surfactant-freeanionic PLA nanoparticles preserves antigenicity and immunogenicity. J Control Release. Sep. 28, 2006;115(1):57-67. Epub Jul. 13, 2006.

Langer, Biomaterials in drug delivery and tissue engineering: one laboratory's experience. Acc Chem Res. 2000;33(2):94-101.

Langer, New methods of drug delivery. Science. 1990;249(4976):1527-33.

Langer, Selected advances in drug delivery and tissue engineering. J Control Release. 1999;62:7-11.

Le Pera et al., Highly specific N-monomethylation of primary aromatic amines. Tetrahedron. 2006;62:6100-6.

Lee et al., Adaptations of nanoscale viruses and other protein cages for medical applications. Nanomedicine. Sep. 2006;2(3):137-49.

Lee et al., Synthesis of 3-(2-aminoethylthio)propyl glycosides. Carbohydr Res. Oct. 1974;37(1):193-201.

Leopold et al., Fluorescent virions: dynamic tracking of the pathway of adenoviral gene transfer vectors in living cells. Hum Gene Ther. 1998;9(3):367-78.

Leucuta et al., Albumin microspheres as a drug delivery system for epirubicin: pharmaceutical, pharmacokinetic and biological aspects. Int J Phar. 1988;41:213-7.

Liang et al., Paclitaxel-Loaded Poly(γ-glutamic acid)-poly(lactide) Nanoparticles as a Targeted Drug Delivery System against Cultured HepG2 Cells. Bioconjug Chem. Mar.-Apr. 2006;17(2):291-9. E-pub ahead of print. E-pub version.

Lim et al., A Self-Destroying Polycationic Polymer: Biodegradable Poly(4-hydroxy-lproline ester). J Am Chem Soc. 1999;121(24):5633-9.

Lim et al., Cationic hyperbranched poly(amino ester): a novel class of DNA condensing molecule with cationic surface, biodegradable three-dimensional structure, and tertiary amine groups in the interior. J Am Chem Soc. Mar. 14, 2001;123(10):2460-1.

Lin et al., Well-Ordered Mesoporous Silica Nanoparticles as Cell Markers. Chem Mater. 2005;17:4570-3.

Lloyd, Disulphide reduction in lysosomes. The role of cysteine. Biochem J. Jul. 1, 1986;237(1):271-2.

Low et al., Folate receptor-targeted drugs for cancer and inflammatory diseases. Adv Drug Deliv Rev. 2004;56(8):1055-8.

Ludewig et al., Induction of optimal anti-viral neutralizing B cell responses by dendritic cells requires transport and release of virus particles in secondary lymphoid organs. Eur J Immunol. 2000;30(1):185-96.

Manolova et al., Nanoparticles target distinct dendritic cell populations according to their size. Eur J Immunol. 2008;38:1404-13.

Mathiowitz et al., Novel microcapsules for delivery systems. Reactive Polymers. 1987;6:275-83.

Mathiowitz et al., Polyanhydride Microspheres as Drug Carriers I. Hot Melt Encapsulation. J Control Release. 1987;5:13-22.

Mathiowitz et al., Polyanhydride Microspheres as Drug Carriers. II . . . Microencapsulation by Solvent Removal. J Appl Polymer Sci. 1988;35:755-74.

Mattheakis et al., Optical coding of mammalian cells using semiconductor quantum dots. Anal Biochem. 2004;327(2):200-8.

Maye et al., Comparison of the phagocytosis of two types of cyclosporin (SDZ OXL 400 and SDZ IMM 125) by alveolar macrophages from hamsters. Cell Biol Toxicol. Dec. 1998;14(6):411-8.

Meister et al., Mechanisms of gene silencing by double-stranded RNA. Nature. 2004;431(7006):343-9.

(56) References Cited

OTHER PUBLICATIONS

Meldal et al., Cu-catalyzed azide-alkyne cycloaddition. Chem Rev. Aug. 2008;108(8):2952-3015.
Milstien et al., Rate acceleration by stereopopulation control: models for enzyme action. Proc Natl Acad Sci U S A. Nov. 1970;67(3):1143-7.
Milstien et al., Stereopopulation control. I. Rate enhancement in the lactonizations of 0-hydroxyhydrocinnamic acids. J Am Chem Soc. Dec. 27, 1972;94(26):9158-65.
Moghimi et al., Long-circulating and target-specific nanoparticles: theory to practice. Pharmacol Rev. 2001;53(2):283-318.
Moghimi et al., Nanomedicine: current status and future prospects. FASEB J. Mar. 2005;19(3):311-30.
Mulligan, The basic science of gene therapy. Science. 1993;260(5110):926-32.
Murray et al., Synthesis and characterization of monodisperse nanocrystals and close-packed nanocrystal assemblies. Ann Rev Mat Sci. 2000;30:545-610.
Nakase et al., Biodegradable microspheres targeting mucosal immune-regulating cells: new approach for treatment of inflammatory bowel disease. J Gastroenterol. Mar. 2003;38 Suppl 15:59-62.
Nickerson et al., Studies on quinone-thioethers. I. Mechanism of formation and properties of thiodione. Biochemistry. May-Jun. 1963;2:537-43. Biochemistry. May-Jun. 1963;2:537-43.
Nielsen et al., Therapeutic efficacy of anti-ErbB2 immunoliposomes targeted by a phage antibody selected for cellular endocytosis. Biochim Biophys Acta. Aug. 19, 2002;1591(1-3):109-118.
Nikou et al., A HER-2/neu peptide admixed with PLA microspheres induces a Th1-biased immune response in mice. Biochim Biophys Acta. Sep. 15, 2005;1725(2):182-9.
Ochsenbein et al., Control of early viral and bacterial distribution and disease by natural antibodies. Science. 1999;286(5447):2156-9.
Ochsenbein et al., Protective T cell-independent antiviral antibody responses are dependent on complement. J Exp Med. 1999;190(8):1165-74.
Olivier et al., Synthesis of pegylated immunonanoparticles. Pharm Res. Aug. 2002;19(8):1137-43.
Ong et al., Redox-triggered contents release from liposomes. J Am Chem Soc. Nov. 5, 2008;130(44):14739-44. Epub Oct. 8, 2008.
Papot et al., Design of selectively activated anticancer prodrugs: elimination and cyclization strategies. Curr Med Chem Anticancer Agents. Mar. 2002;2(2):155-85.
Pasqualini et al., Aminopeptidase N is a receptor for tumor-homing peptides and a target for inhibiting angiogenesis. Cancer Res. 2000;60(3):722-7.
Patri et al., Synthesis and in Vitro Testing of J591 Antibody—Dendrimer Conjugates for Targeted Prostate Cancer Therapy. Bioconj Chem. 2004;15:1174-81.
Pellegrino et al., On the development of colloidal nanoparticles towards multifunctional structures and their possible use for biological applications. Small. 2005;1(1):48-63.
Phillips et al., Enhanced antibody response to liposome-associated protein antigens: preferential stimulation of IgG2a/b production. Vaccine. 1992;10(3):151-8.
Pimentel et al., Peptide nanoparticles as novel immunogens: design and analysis of a prototypic severe acute respiratory syndrome vaccine. Chem Biol Drug Des. Jan. 2009;73(1):53-61.
Pitaksuteepong, Nanoparticles: A vaccine adjuvant for subcutaneous administration. Naresuan University J. 2005;13(2):53-62.
Popielarski et al., A nanoparticle-based model delivery system to guide the rational design of gene delivery to the liver. 2. In vitro and in vivo uptake results. Bioconjug Chem. Sep.-Oct. 2005;16(5):1071-80.
Qiu et al., PLA-coated gold nanoparticles for the labeling of PLA biocarriers. Chem Mater. 2004;16:850-6.
Quintanar-Guerrero et al., Preparation Techniques and Mechanisms of Formation of Biodegradable Nanoparticles from Preformed Polymers. Drug Dev Industrial Pharmacy. 1998;24(12):1113-28.

Raman et al., Peptide Based Nanoparticles as a Platform for Vaccine Design. http://www.nsti.org/Nanotech2005/showabstract.html?absno=637. 2005. Abstract Only.
Reddy et al., Exploiting lymphatic transport and complement activation in nanoparticle vaccines. Nat Biotech. 2007;25(10):1159-64.
Reis et al., Nanoencapsulation I. Methods for preparation of drug-loaded polymeric nanoparticles. Nanomedicine. 2006;2:8-21.
Rissing et al., The Thiol-ene Reaction for the Synthesis of Multifunctional Branched. Organosilanes. Organometallics. 2008;27:5394-7. E-pub Sep. 11, 2008.
Robbins et al., Stable expression of shRNAs in human CD34+ progenitor cells can avoid induction of interferon responses to siRNAs in vitro. Nature Biotechnology. 2006;24(5):566-71.
Rostovtsev et al., A stepwise huisgen cycloaddition process: copper(I)-catalyzed regioselective "ligation" of azides and terminal alkynes. Angew Chem Int Ed Engl. Jul. 15, 2002;41(14):2596-9.
Saito et al., Drug delivery strategy utilizing conjugation via reversible disulfide linkages: role and site of cellular reducing activities. Adv Drug Deliv Rev. Feb. 10, 2003;55(2):199-215.
Salmeron et al., Encapsulation Study of 6-Methylprednisolone in Lipid Microspheres. Drug Develop Indust Pharm. 1997;23(2):133-6.
Samuel et al, Polymeric nanoparticles for targeted delivery of therapeutic vaccines to dendritic cells. Proc Intl Conf on MEMS, NANO and Smart Sys. Jul. 2003;20-23:242-6.
Schultz et al., Single-target molecule detection with nonbleaching multicolor optical immunolabels. Proc Natl Acad Sci USA. 2000;97(3):996-1001.
Schultz, Plasmon resonant particles for biological detection. Curr Op Biotechnol. 2003;14:13-22.
Shahiwala et al., Nanocarriers for systemic and mucosal vaccine delivery. Recent Pat Drug Deliv Formul. 2007;1(1):1-9.
Sharma et al., Pharmaceutical aspects of intranasal delivery of vaccines using particulate systems. J Pharm Sci. Mar. 2009;98(3):812-43.
Shen et al., Enhanced and prolonged cross-presentation following endosomal escape of exogenous antigens encapsulated in biodegradable nanoparticles. Immunol. 2006;117:78-88.
Shestopalov et al., Multi-step synthesis of nanoparticles performed on millisecond time scale in a microfluidic droplet-based system. Lab Chip. 2004;4(4):316-21.
Shu et al., Novel pH-sensitive citrate cross-linked chitosan film for drug controlled release. Int J Pharm. Jan. 5, 2001;212(1):19-28.
Singh et al., Anionic microparticles are a potent delivery system for recombinant antigens from Neisseria meningitidis serotype B. J Pharm Sci. Feb. 2004;93(2):273-82.
Singh et al., Cationic microparticles are an effective delivery system for immune stimulatory cpG DNA. Pharm Res. Oct. 2001;18(10):1476-9.
Singh et al., Nanoparticles and microparticles as vaccine-delivery systems. Expert Rev Vaccines. Oct. 2007;6(5):797-808.
Stivaktakis et al., Immune responses in mice of beta-galactosidase adsorbed or encapsulated in poly(lactic acid) and poly(lactic-co-glycolic acid) microspheres. J Biomed Mater Res A. Jun. 1, 2005;73(3):332-8.
Stivaktakis et al., PLA and PLGA microspheres of beta-galactosidase: Effect of formulation factors on protein antigenicity and immunogenicity. J Biomed Mater Res A. Jul. 1, 2004;70(1):139-48.
Storm et al., Surface Modification of Nanoparticles to Oppose Uptake by the Mononuclear Phagocyte System. Adv Drug Deliv Rev. 1995;17:31-48.
Suri et al., Nanotechnology-based drug delivery systems. J Occup Med Toxicol. Dec. 1, 2007;2:16.
Tabata et al., Macrophage activation through phagocytosis of poly (L-lactic acid) microspheres containing an immunomodulatory agent. 1989;7(2):79-86.
Tabata et al., Protein precoating of polylactide microspheres containing a lipophilic immunopotentiator for enhancement of macrophage phagocytosis and activation. Pharm Res. Apr. 1989;6(4):296-301.
Tang et al., In Vitro Gene Delivery by Degraded Polyamidoamine Dendrimers. Bioconjugate Chem. 1996;7:703-14.

(56) References Cited

OTHER PUBLICATIONS

Taylor et al., Macrophage receptors and immune recognition. Annu Rev Immunol. 2005;23:901-44.
Thorek et al., Comparative analysis of nanoparticle-antibody conjugations: carbodiimide versus click chemistry. Mol Imaging. Jul.-Aug. 2009;8(4):221-9.
Timmerman, Carrier protein conjugate vaccines: the "missing link" to improved antibody and CTL responses? Hum Vaccin. Mar. 2009;5(3):181-3. Epub Mar. 24, 2009.
Tong et al., Ring-opening polymerization-mediated controlled formulation of polylactide-drug nanoparticles. J Am Chem Soc. Apr. 8, 2009;131(13):4744-54. E-pub Mar. 12, 2009.
Trindade et al., Nanocrystalline Semiconductors: Synthesis, Properties, and Perspectives. Chem Mat. 2001;13(11):3843-58.
Uhrich et al., Polymeric Systems for Controlled Drug Release. Chem Rev. 1999;99(11):3181-98.
Uwatoku et al., Application of Nanoparticle Technology for the Prevention of Restenosis After Balloon Injury in Rats. Circ Res. 2003;92(7):e62-9.
Van Broekhoven et al., Targeting dendritic cells with antigen-containing liposomes: a highly effective procedure for induction of antitumor immunity and for tumor immunotherapy. Cancer Res. Jun. 15, 2004;64(12):4357-65.
Vauthier et al., Design aspects of poly(alkylcyanoacrylate) nanoparticles for drug delivery. J Drug Target. Dec. 2007;15(10):641-63.
Von Andrian et al., Homing and cellular traffic in lymph nodes. Nat Rev Immunol. 2003;3(11):867-78.
Waldvogel et al., Nucleotides. Part 55. Synthesis and applicatino of a novel linker for solid-phase synthesis of modified oligonucleotides. Helv Chim Acta. 1998;81:46-58.
Wang et al., Synthesis of a Novel Esterase-Sensitive Cyclic Prodrug System for Peptides That Utilizes a "Trimethyl Lock"-Facilitated Lactonization Reaction. J Org Chem. 1997;62:1363-7.
Whelan et al., Efficient recovery of infectious vesicular stomatitis virus entirely from cDNA clones. Proc Natl Acad Sci USA. 1995;92(18):8388-92.
Wong SS, Chemistry of Protein Conjugation and Cross-linking, CRC Press Publishers, Boca Raton, 1991.
Wriggers et al. Control of protein functional dynamics by peptide linkers. Biopolymers. 2005;80(6):736-46.
Wu et al., Synthesis of glycoconjugate vaccines for Candida albicans using novel linker methodology. J Org Chem. Sep. 2, 2005;70(18):7381-8.
Yang et al., Tumor necrosis factor alpha blocking peptide loaded PEG-PLGA nanoparticles: preparation and in vitro evaluation. Int J Pharm. Feb. 22, 2007;331(1):123-32.
Yang, Imaging of vascular gene therapy. Radiology. 2003;228:36-49.
Yoo et al., In vitro and in vivo anti-tumor activities of nanoparticles based on doxorubicin-PLGA conjugates. J Control Release. 2000;68(3):419-31.
Yuan et al., Intranasal immunization with chitosan/pCETP nanoparticles inhibits atherosclerosis in a rabbit model of atherosclerosis. Vaccine. Jul. 4, 2008;26(29-30):3727-34. Epub May 16, 2008.
Zauner et al., Polylysine-based transfection systems utilizing receptor-mediated delivery. Adv Drug Del Rev. 1998;30:97-113.
Zhang et al., A comparative study of the antigen-specific immune response induced by co-delivery of CpG ODN and antigen using fusion molecules or biodegradable microparticles. J Pharm Sci. Dec. 2007;96(12):3283-92.
Zhang et al., Advance in the Synthesis of Poly( Amino Acid) Copolymers. Polymer Mater Sci Eng. 2006;22(4):10-4.
Zhang et al., Nanoparticles of poly(lactide)/vitamin E TPGS copolymer for cancer chemotherapy: synthesis, formulation, characterization and in vitro drug release. Biomaterials. Jan. 2006;27(2):262-70.
Zheng et al., Highly fluorescent, water-soluble, size-tunable gold quantum dots. Phys Rev Lett. 2004;93(7):077402.1-4.
Zhou et al., Investigation on a novel core-coated micro spheres protein delivery system. J Control Release. Jul. 10, 2001;75(1-2):27-36.
Zhou et al., Preparation of poly(L-serine ester): a structural analog of conventional poly(L-serine). Macromolecules. 1990;23(14):3399-406.
Robbins et al., Fabricated Nanoparticles with Cross Validation Using a Humanized Mouse Model. Nanomed Nanotech Biol Med. 2015. Accepted manuscript. doi: 10.1016/j.nano.2014.11.010. 36 pages.
U.S. Appl. No. 12/788,260, filed May 26, 2010, Zepp et al.
U.S. Appl. No. 13/948,129, filed Jul. 22, 2013, Zepp et al.
U.S. Appl. No. 14/273,099, filed May 8, 2014, Zepp et al.
U.S. Appl. No. 12/788,261, filed May 26, 2010, Lipford et al.
U.S. Appl. No. 12/862,076, filed Aug. 24, 2010, Fraser et al.
U.S. Appl. No. 13/116,453, filed May 26, 2011, Bratzler et al.
U.S. Appl. No. 12/764,569, filed Apr. 21, 2010, Lipford et al.
U.S. Appl. No. 13/116,488, filed May 26, 2011, Bratzler et al.
U.S. Appl. No. 14/717,451, filed May 20, 2016, Ilyinskii et al.
U.S. Appl. No. 13/116,556, filed May 26, 2011, Bratzler et al.
U.S. Appl. No. 13/289,211, filed Nov. 4, 2011, Zepp et al.
U.S. Appl. No. 13/428,340, filed Mar. 23, 2012, Altreuter et al.
U.S. Appl. No. 15/050,397, filed Feb. 22, 2016, Fraser et al.
U.S. Appl. No. 14/810,418, filed Jul. 27, 2015, Fraser et al.
U.S. Appl. No. 14/802,260, filed Jul. 17, 2015, Altreuter et al.
U.S. Appl. No. 13/560,955, filed Jul. 27, 2012, Altreuter et al.
U.S. Appl. No. 14/810,427, filed Jul. 27, 2015, Fraser et al.
U.S. Appl. No. 15/061,096, filed Mar. 4, 2016, Fraser et al.
U.S. Appl. No. 13/457,994, filed Apr. 27, 2012, Fraser et al.
U.S. Appl. No. 14/810,442, filed Jul. 27, 2015, Fraser et al.
U.S. Appl. No. 14/810,450, filed Jul. 27, 2015, Fraser et al.
U.S. Appl. No. 14/810,457, filed Jul. 27, 2015, Kishimoto et al.
U.S. Appl. No. 15/061,204, filed Mar. 4, 2016, Kishimoto et al.
U.S. Appl. No. 13/457,936, filed Apr. 27, 2012, Kishimoto et al.
U.S. Appl. No. 14/810,466, filed Jul. 27, 2015, Kishimoto et al.
U.S. Appl. No. 13/458,220, filed Apr. 27, 2012, Fraser et al.
U.S. Appl. No. 14/810,472, filed Jul. 27, 2015, Fraser et al.
U.S. Appl. No. 14/161,660, filed Jan. 22, 2014, Maldonado.
U.S. Appl. No. 14/810,476, filed Jul. 27, 2015, Maldonado.
U.S. Appl. No. 14/269,047, filed May 2, 2014, Maldonado et al.
U.S. Appl. No. 14/296,204, filed Jun. 4, 2014, Maldonado et al.
U.S. Appl. No. 14/269,048, filed May 2, 2014, Maldonado.
U.S. Appl. No. 14/269,054, filed May 2, 2014, Maldonado.
U.S. Appl. No. 14/269,058, filed May 2, 2014, Kishimoto.
U.S. Appl. No. 14/269,056, filed May 2, 2014, Maldonado et al.
U.S. Appl. No. 14/269,042, filed May 2, 2014, Kishimoto et al.
U.S. Appl. No. 14/742,583, filed Jun. 17, 2015, Kishimoto.
U.S. Appl. No. 14/751,106, filed Jun. 25, 2015, Kishimoto et al.
U.S. Appl. No. 14/846,949, filed Sep. 7, 2015, Kishimoto.
U.S. Appl. No. 14/846,952, filed Sep. 7, 2015, Kishimoto.
U.S. Appl. No. 14/846,958, filed Sep. 7, 2015, Kishimoto.
U.S. Appl. No. 14/846,964, filed Sep. 7, 2015, Kishimoto.
U.S. Appl. No. 14/934,132, filed Nov. 5, 2014, Griset et al.
U.S. Appl. No. 14/934,135, filed Nov. 5, 2015, Griset et al.
U.S. Appl. No. 14/846,967, filed Sep. 7, 2015, Kishimoto.
Rogers et al., A 2-aminobenzimidazole that inhibits and disperses gram-positive biofilms through a zinc-dependent mechanism. J Am Chem Soc. Jul. 29, 2009;131(29):9868-9. doi: 10.1021/ja9024676.
Kurimoto et al., Synthesis and structure-activity relationships of 2-amino-8-hydroxyadenines as orally active interferon inducing agents. Bioorg Med Chem. Dec. 1, 2003;11(24):5501-8.

\* Release at pH 4.5 was higher for each of the above formulations.

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(20)
<223> OTHER INFORMATION: fully phosphorothioated backbone

<400> SEQUENCE: 1
```

```
tccatgacgt tcctgacgtt                                               20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
tccatgacgt tcctgacgtt                                               20
```

IMMUNOMODULATORY AGENT-POLYMERIC COMPOUNDS

RELATED APPLICATIONS

This application is a continuation of U.S. patent application Ser. No. 14/138,601, filed Dec. 23, 2013, now allowed, which is a continuation of U.S. patent application Ser. No. 12/788,266, filed May 26, 2010, now U.S. Pat. No. 8,629,151, which claims the benefit under 35 U.S.C. § 119 of U.S. Provisional Application Nos. 61/217,129, 61/217,117, 61/217,124, and 61/217,116, each filed May 27, 2009, the contents of each of which are incorporated herein by reference in their entirety.

FIELD OF THE INVENTION

This invention relates to compositions, and related compounds and methods, of conjugates of immunomodulatory agents and polymers or unit(s) thereof. The conjugates may be contained within synthetic nanocarriers, and the immunomodulatory agents may be released from the synthetic nanocarriers in a pH sensitive manner.

BACKGROUND

Immunomodulatory agents are used to produce immune responses in subjects. It is at times advantageous to attach such agents to delivery vehicles. Currently, known attachment chemistries often require certain reactive groups, utilize certain activation steps for attachment to occur, and/or result in conjugates that do not exhibit optimal properties. There is a need, therefore, for new methods for the attachment of immunomodulatory agents to delivery vehicles as well as a need for the resulting conjugates that exhibit desired properties.

SUMMARY OF THE INVENTION

In one aspect, the present invention provides a compound that comprises a structure as in formula (I):

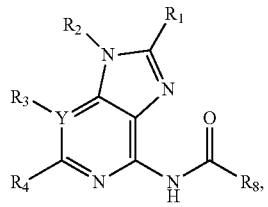

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; and $R_8$ is a biodegradable polymer or unit thereof. In one embodiment, for the compound of formula (I), the biodegradable polymer or unit thereof comprises a polyester, polycarbonate, or a polyamide, or unit thereof. In another embodiment, the biodegradable polymer or unit thereof comprises poly(lactic acid), poly(glycolic acid), poly(lactic-co-glycolic acid), or polycaprolactone, or unit thereof.

In another aspect, the present invention provides a compound that comprises a structure as in formula (II):

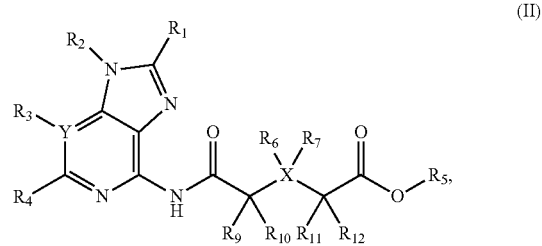

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; $R_5$ is a polymer or unit thereof; X=C, N, O, or S; $R_6$ and $R_7$ are each independently absent, H, or substituted; and $R_9$, $R_{10}$, $R_{11}$, and $R_{12}$ are each independently H, a halogen, OH, thio, $NH_2$, or substituted or unsubstituted alkyl, aryl, heterocyclic, alkoxy, aryloxy, alkylthio, arylthio, alkylamino, or arylamino. In a further embodiment, for the compound of formula (II), the polymer or unit thereof comprises a polyester, polycarbonate, polyamide, or a polyether, or unit thereof. In another embodiment, the polymer or unit thereof comprises poly(lactic acid), poly(glycolic acid), poly(lactic-co-glycolic acid), polycaprolactone, or poly(ethylene glycol), or unit thereof. In yet another embodiment, the polymer is biodegradable.

In one embodiment, for a compound of formula (I) or (II), $R_1$ is H, $R_2$ is isobutyl, Y is C, and $R_3$ and $R_4$ are combined to form a benzene ring with the carbon atoms of the pyridine ring to which they are connected. In another embodiment, $R_1$ is ethoxymethyl, $R_2$ is hydroxyisobutyl, Y=C, and $R_3$ and $R_4$ are combined to form a benzene ring with the carbon atoms of the pyridine ring to which they are connected. In yet another embodiment, $R_1$ is ethoxymethyl, $R_2$ is methanesulfonamidoisobutyl, Y=C, and $R_3$ and $R_4$ are combined to form a benzene ring with the carbon atoms of the pyridine ring to which they are connected. In one embodiment, $R_1$ is OH, $R_2$ is benzyl, Y=N, $R_3$ is absent, and $R_4$ is butoxy. In another embodiment, Y is N, $R_1$ is OH, $R_2$ is benzyl, $R_3$ is absent, and $R_4$ is butylamino. In yet another embodiment, Y is N, $R_1$ is OH, $R_2$ is benzyl, $R_3$ is absent, and $R_4$ is butoxy. In still yet another embodiment, Y is N, $R_1$ is OH, $R_2$ is benzyl, $R_3$ is absent, and $R_4$ is benzylamino. In one embodiment, Y is N, $R_1$ is OH, $R_2$ is benzyl, $R_3$ is absent, and $R_4$ is pentyl.

In one embodiment, for a compound of formula (I) or (II), the polymer is insoluble in water at pH=7.4 and at 25° C. In another embodiment, for a compound of formula (I) or (II), the polymer is insoluble in water at pH=7.4 and at 25° C. but soluble at pH=4.5 and at 25° C. In one embodiment, for a compound of formula (I) or (II), the polymer has a weight average molecular weight ranging from 800 Daltons to 10,000 Daltons, as determined using gel permeation chromatography. In another embodiment, for a compound of formula (I) or (II), the polymer or unit thereof does not comprise polyketal or unit thereof. In one embodiment, a composition is provided comprising a compound having a formula (I) or (II). In a further embodiment, the composition further comprises a pharmaceutically acceptable excipient.

In one embodiment, a synthetic nanocarrier is provided that comprises the compound having a formula (I) or (II). In a further embodiment, the synthetic nanocarrier further comprises a B cell antigen and/or a T cell antigen. In yet another embodiment, the synthetic nanocarrier further comprises an antigen presenting cell (APC) targeting feature. In a further embodiment, the synthetic nanocarrier is a dendrimer, buckyball, nanowire, peptide or protein-based nanoparticle, nanoparticle that comprises a combination of nanomaterials, spheroidal nanoparticle, cubic nanoparticle, pyramidal nanoparticle, oblong nanoparticle, cylindrical nanoparticle, or toroidal nanoparticle. In another embodiment, a composition is provided comprising a synthetic nanocarrier. In yet a further embodiment, the composition further comprises a pharmaceutically acceptable excipient.

In one embodiment, a composition comprising a vaccine comprising a compound of formula (I) or (II) is provided. In another embodiment, a composition comprising a vaccine comprising a composition comprising a compound of formula (I) or (II) is provided. In yet another embodiment, a composition comprising a vaccine comprising the synthetic nanocarrier comprising a compound of formula (I) or (II) is provided. In still yet another embodiment, a method comprises a administering to a subject any of the above described compounds, compositions, or synthetic nanocarrier is provided. In a further embodiment, an immune response is induced or enhanced in the subject following administering to a subject any of the above described compounds, compositions, or synthetic nanocarrier.

In one aspect, a method for making a conjugate that comprises a structure as in formula (I):

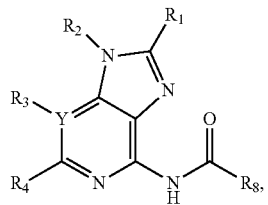

(I)

comprises: activating a biodegradable polymer or unit thereof, and exposing the activated biodegradable polymer or unit thereof and a compound comprising a structure as in formula (III) to a base and/or solvent:

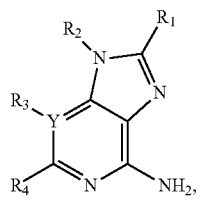

(III)

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; and $R_8$ is a biodegradable polymer or unit thereof. In one embodiment, the biodegradable polymer or unit thereof comprises a polyester, polycarbonate, or a polyamide, or unit thereof. In a further embodiment, the biodegradable polymer or unit thereof comprises poly(lactic acid), poly(glycolic acid), poly(lactic-co-glycolic acid), or polycaprolactone, or unit thereof.

In another aspect, a method for making a conjugate that comprises a structure as in formula (I):

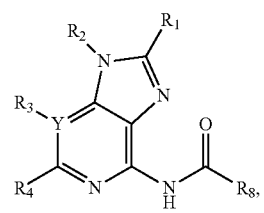

(I)

comprises exposing a composition comprising a polymer or unit thereof and a compound comprising a structure as in formula (III) to a coupling agent and base and/or solvent:

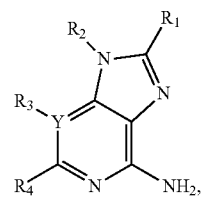

(III)

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; and $R_8$ is a polymer or unit thereof.

In another aspect, a method for making a conjugate that comprises a structure as in formula (II):

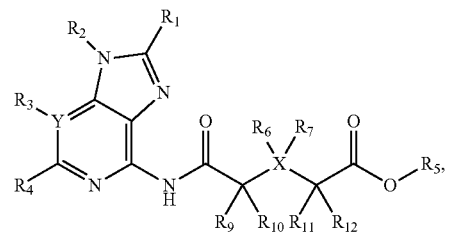

(II)

comprises combining an alcohol, a catalyst, and a compound comprising a structure as in formula (IV):

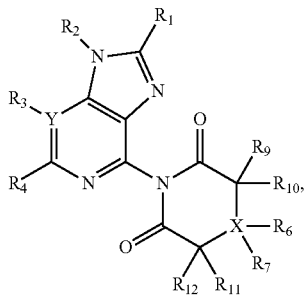
(IV)

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; $R_5$ is a polymer or unit thereof; X is C, N, O, or S; $R_6$ and $R_7$ are each independently H or substituted; and $R_9$, $R_{10}$, $R_{11}$, and $R_{12}$ are each independently H, a halogen, OH, thio, $NH_2$, or substituted or unsubstituted alkyl, aryl, heterocyclic, alkoxy, aryloxy, alkylthio, arylthio, alkylamino, or arylamino; and heating the alcohol, catalyst, and compound. In some embodiment, the alcohol, catalyst, and compound are heated in the presence of a solvent.

In yet another aspect, a method for making a conjugate that comprises a structure as in formula (II):

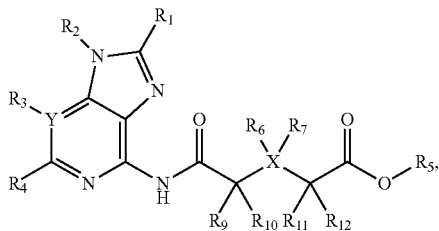
(II)

comprises combining an alcohol and a compound comprising a structure as in formula (IV):

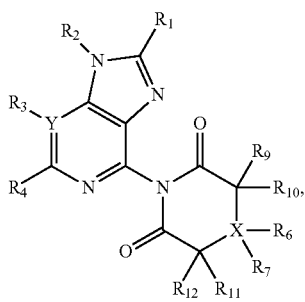
(IV)

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; $R_5$ is a polymer or unit thereof; X is C, N, O, or S; $R_6$ and $R_7$ are each independently H or substituted; and $R_9$, $R_{10}$, $R_{11}$, and $R_{12}$ are each independently H, a halogen, OH, thio, $NH_2$, or substituted or unsubstituted alkyl, aryl, heterocyclic, alkoxy, aryloxy, alkylthio, arylthio, alkylamino, or arylamino; heating the alcohol and compound; and adding a catalyst. In one embodiment, the alcohol, compound, and catalyst are heated while and/or after the catalyst is added.

In yet another aspect, a method for making a conjugate that comprises a structure as in formula (II):

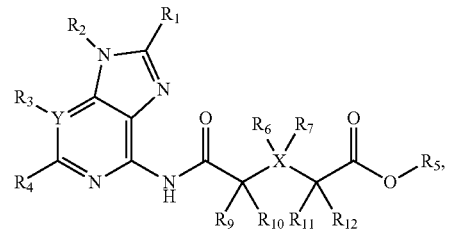
(II)

comprises combining an alcohol, a catalyst, and a compound comprising a structure as in formula (IV):

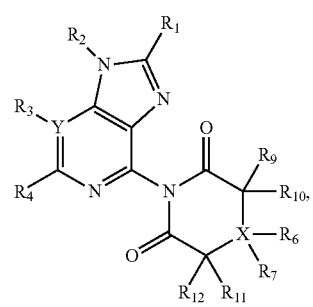
(IV)

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; $R_5$ is a polymer or unit thereof; X is C, N, O, or S; $R_6$ and $R_7$ are each independently H or substituted; and $R_9$, $R_{10}$, $R_{11}$, and $R_{12}$ are each independently H, a halogen, OH, thio, $NH_2$, or substituted or unsubstituted alkyl, aryl, heterocyclic, alkoxy, aryloxy, alkylthio, arylthio, alkylamino, or arylamino.

In one embodiment, for a method of making a compound of formula (II), the alcohol is a polymer or unit thereof with a terminal hydroxyl group. In a further embodiment, the polymer or unit thereof comprises a polyester, polycarbonate, polyamide, or a polyether, or unit thereof. In yet another embodiment, the polymer or unit thereof comprises, poly (lactic acid), poly(glycolic acid), poly(lactic-co-glycolic acid), polycaprolactone, or poly(ethylene glycol), or unit thereof.

In one embodiment, for a method of making a compound of formula (II), the catalyst is a phosphazine base, 1,8-diazabicycloundec-7-ene, 1,4,7-triazabicyclodecene, or N-methyl-1,4,7-triazabicyclodecene. In another embodiment, the polymer has a weight average molecular weight ranging from 800 Daltons to 10,000 Daltons, as determined using gel permeation chromatography. In yet another embodiment, the polymer is insoluble in water at pH=7.4 and at 25° C. In another embodiment, the polymer is insoluble in water at pH=7.4 and at 25° C. but soluble at pH=4.5 and at 25° C. In still yet another embodiment, the polymer or unit thereof does not comprise polyketal or unit thereof.

In one embodiment, for a method of making a compound of formula (II), $R_1$ is H, $R_2$ is isobutyl, Y is C, and $R_3$ and $R_4$ are combined to form a benzene ring with the carbon atoms of the pyridine ring to which they are connected. In another embodiment, $R_1$ is ethoxymethyl, $R_2$ is hydroxyisobutyl, Y=C, and $R_3$ and $R_4$ are combined to form a benzene ring with the carbon atoms of the pyridine ring to which they are connected. In yet another embodiment, $R_1$ is ethoxymethyl, $R_2$ is methanesulfonamidoisobutyl, Y=C, and $R_3$ and $R_4$ are combined to form a benzene ring with the carbon atoms of the pyridine ring to which they are connected. In still yet another embodiment, $R_1$ is OH, $R_2$ is benzyl, Y=N, $R_3$ is absent, and $R_4$ is butoxy. In another embodiment, Y is N, $R_1$ is OH, $R_2$ is benzyl, $R_3$ is absent, and $R_4$ is butylamino. In one embodiment, Y is N, $R_1$ is OH, $R_2$ is benzyl, $R_3$ is absent, and $R_4$ is butoxy. In another embodiment, Y is N, $R_1$ is OH, $R_2$ is benzyl, $R_3$ is absent, and $R_4$ is benzylamino. In yet another embodiment, Y is N, $R_1$ is OH, $R_2$ is benzyl, $R_3$ is absent, and $R_4$ is pentyl.

In one aspect, the present invention provides a compound that comprises a structure as in formula (IV):

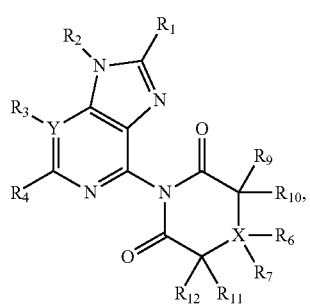

(IV)

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; X is C, N, O, or S; $R_6$ and $R_7$ are each independently H or substituted; and $R_9$, $R_{10}$, $R_{11}$, and $R_{12}$ are each independently H, a halogen, OH, thio, $NH_2$, or substituted or unsubstituted alkyl, aryl, heterocyclic, alkoxy, aryloxy, alkylthio, arylthio, alkylamino, or arylamino.

In one embodiment, for a compound of formula (IV), $R_1$ is H, $R_2$ is isobutyl, Y is C, and $R_3$ and $R_4$ are combined to form a benzene ring with the carbon atoms of the pyridine ring to which they are connected. In another embodiment, $R_1$ is ethoxymethyl, $R_2$ is hydroxyisobutyl, Y=C, and $R_3$ and $R_4$ are combined to form a benzene ring with the carbon atoms of the pyridine ring to which they are connected. In yet another embodiment, $R_1$ is ethoxymethyl, $R_2$ is methanesulfonamidoisobutyl, Y=C, and $R_3$ and $R_4$ are combined to form a benzene ring with the carbon atoms of the pyridine ring to which they are connected. In still yet another embodiment, $R_1$ is OH, $R_2$ is benzyl, Y=N, $R_3$ is absent, and $R_4$ is butoxy. In one embodiment, Y is N, $R_1$ is OH, $R_2$ is benzyl, $R_3$ is absent, and $R_4$ is butylamino. In another embodiment, Y is N, $R_1$ is OH, $R_2$ is benzyl, $R_3$ is absent, and $R_4$ is butoxy. In yet another embodiment, Y is N, $R_1$ is OH, $R_2$ is benzyl, $R_3$ is absent, and $R_4$ is benzylamino. In still yet another embodiment, Y is N, $R_1$ is OH, $R_2$ is benzyl, $R_3$ is absent, and $R_4$ is pentyl. In one embodiment, a composition is provided having a compound of formula (IV).

In one aspect, the present invention provides a method for making a compound that comprises a structure as in formula (IV):

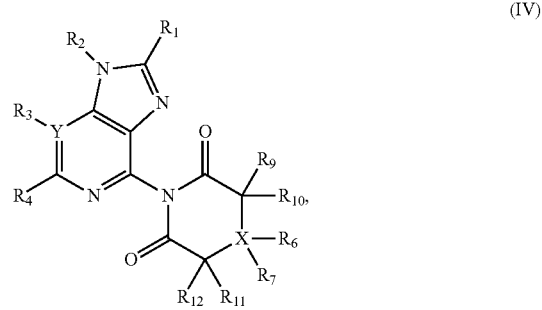

(IV)

comprising combining, in the presence of a solvent and/or heat, a compound that comprises a structure as in formula (III):

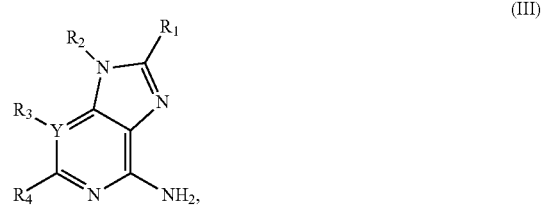

(III)

and a compound comprising a structure as in formula (V):

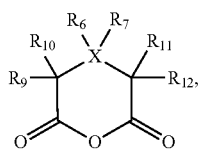

(V)

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; X is C, N, O, or S; $R_6$ and $R_7$ are each independently H or substituted; and $R_9$, $R_{10}$, $R_{11}$, and $R_{12}$ are each independently H, a halogen, OH, thio, $NH_2$, or substituted or unsubstituted alkyl, aryl, heterocyclic, alkoxy, aryloxy, alkylthio, arylthio, alkylamino, or arylamino.

In one embodiment, for a method comprising a compound of formula (IV), $R_1$ is H, $R_2$ is isobutyl, Y is C, and $R_3$ and $R_4$ are combined to form a benzene ring with the carbon atoms of the pyridine ring to which they are connected. In another embodiment, $R_1$ is ethoxymethyl, $R_2$ is hydroxyisobutyl, Y=C, and $R_3$ and $R_4$ are combined to form a benzene ring with the carbon atoms of the pyridine ring to which they are connected. In yet another embodiment, $R_1$ is ethoxymethyl, $R_2$ is methanesulfonamidoisobutyl, Y=C, and $R_3$ and $R_4$ are combined to form a benzene ring with the carbon atoms of the pyridine ring to which they are connected. In still yet another embodiment, $R_1$ is OH, $R_2$ is benzyl, Y=N, $R_3$ is absent, and $R_4$ is butoxy. In one embodiment, Y is N, $R_1$ is OH, $R_2$ is benzyl, $R_3$ is absent, and $R_4$ is butylamino. In another embodiment, Y is N, $R_1$ is OH, $R_2$ is benzyl, $R_3$ is absent, and $R_4$ is butoxy. In yet another embodiment, Y is N, $R_1$ is OH, $R_2$ is benzyl, $R_3$ is absent, and $R_4$ is benzylamino. In still yet another embodiment, Y is N, $R_1$ is OH, $R_2$ is benzyl, $R_3$ is absent, and $R_4$ is pentyl.

In one aspect, the present invention provides a method for making a conjugate that comprises a structure as in formula (VI):

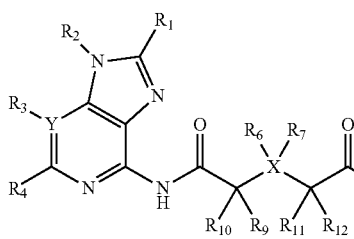

comprising combining a catalyst, a diol having the formula (VII):

HO-polymer-OH    (VII), and a compound comprising a structure as in formula (IV):

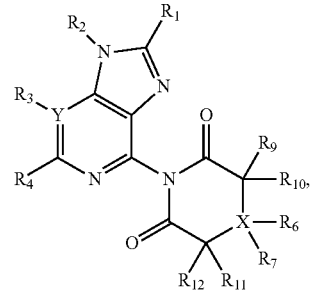

(IV)

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; X is C, N, O, or S; $R_6$ and $R_7$ are each independently H or substituted; and $R_9$, $R_{10}$, $R_{11}$, and $R_{12}$ are each independently H, a halogen, OH, thio, $NH_2$, or substituted or unsubstituted alkyl, aryl, heterocyclic, alkoxy, aryloxy, alkylthio, arylthio, alkylamino, or arylamino; and heating the alcohol, catalyst, and compound. In one embodiment, for a method comprising a compound of formula (VI), the alcohol, catalyst, and compound are heated in the presence of a solvent. In one embodiment of this aspect, the polymer is intended to include a unit of a polymer provided herein.

In another aspect, the present invention provides a method for making a conjugate that comprises a structure as in formula (VI):

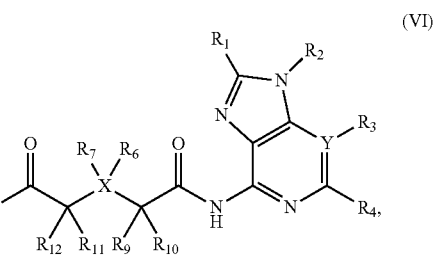

(VI)

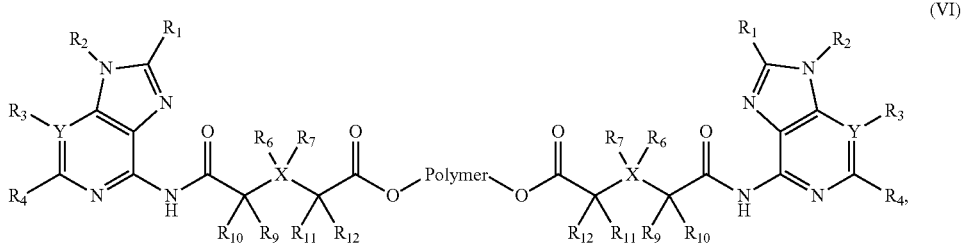

comprising combining a diol having the formula (VII):

HO-polymer-OH  (VII), and a compound comprising a structure as in formula (IV):

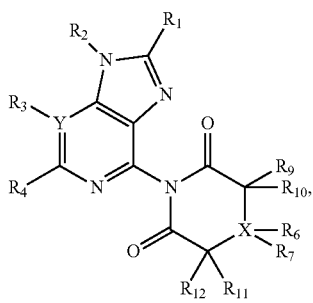

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; X is C, N, O, or S; $R_6$ and $R_7$ are each independently H or substituted; and $R_9$, $R_{10}$, $R_{11}$, and $R_{12}$ are each independently H, a halogen, OH, thio, $NH_2$, or substituted or unsubstituted alkyl, aryl, heterocyclic, alkoxy, aryloxy, alkylthio, arylthio, alkylamino, or arylamino; heating the alcohol and compound; and adding a catalyst. In a further embodiment, the alcohol, compound, and catalyst are heated while and/or after the catalyst is added. In one embodiment of this aspect, the polymer is intended to include comprising a unit of a polymer provided herein.

In one aspect, the present invention provides a method for making a conjugate that comprises a structure as in formula (VI):

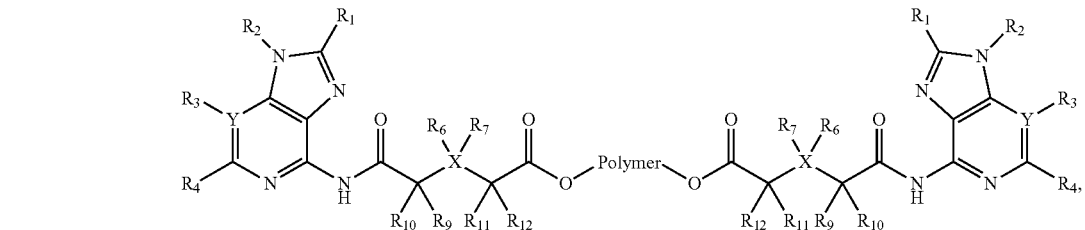

comprising combining, a catalyst, a diol having the formula (VII):

HO-polymer-OH  (VII), and a compound comprising a structure as in formula (IV):

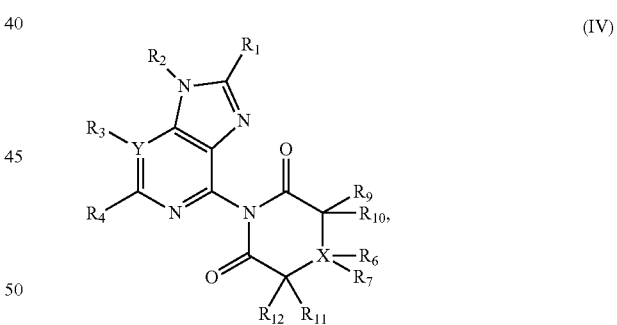

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; X is C, N, O, or S; $R_6$ and $R_7$ are each independently H or substituted; and $R_9$, $R_{10}$, $R_{11}$, and $R_{12}$ are each independently H, a halogen, OH, thio, NH$_2$, or substituted or unsubstituted alkyl, aryl, heterocyclic, alkoxy, aryloxy, alkylthio, arylthio, alkylamino, or arylamino.

In one embodiment, for a method of making a compound comprising the formula (VI), the compound of formula (VII) is selected from the group consisting polyketaldiols, poly(ethylene)glycol, polycaprolactone diol, diblock polylactide-co-poly(ethylene)glycol, diblock polylactide/polyglycolide-co-poly(ethylene)glycol, diblock polyglycolide-co-poly(ethylene)glycol, poly(propylene) glycol, and poly(hexamethylene carbonate)diol. In one embodiment, for a method of making a compound comprising the formula (VI), the catalyst is a phosphazine base, 1,8-diazabicycloundec-7-ene, 1,4,7-triazabicyclodecene, or N-methyl-1,4,7-triazabicyclodecene. In a further embodiment, the polymer has a weight average molecular weight ranging from 800 Daltons to 10,000 Daltons, as determined using gel permeation chromatography. In another embodiment, the polymer is insoluble in water at pH=7.4 and at 25° C. In another embodiment, the polymer is insoluble in water at pH=7.4 and at 25° C. but soluble at pH=4.5 and at 25° C. In yet another embodiment, the polymer does not comprise polyketal or unit thereof.

In one embodiment, for a method of making a compound having the formula (VI), $R_1$ is H, $R_2$ is isobutyl, Y is C, and $R_3$ and $R_4$ are combined to form a benzene ring with the carbon atoms of the pyridine ring to which they are connected. In another embodiment, $R_1$ is ethoxymethyl, $R_2$ is hydroxyisobutyl, Y=C, and $R_3$ and $R_4$ are combined to form a benzene ring with the carbon atoms of the pyridine ring to which they are connected. In yet another embodiment, $R_1$ is ethoxymethyl, $R_2$ is methanesulfonamidoisobutyl, Y=C, and $R_3$ and $R_4$ are combined to form a benzene ring with the carbon atoms of the pyridine ring to which they are connected. In still yet another embodiment, $R_1$ is OH, $R_2$ is benzyl, Y=N, $R_3$ is absent, and $R_4$ is butoxy. In one embodiment, Y is N, $R_1$ is OH, $R_2$ is benzyl, $R_3$ is absent, and $R_4$ is butylamino. In another embodiment, Y is N, $R_1$ is OH, $R_2$ is benzyl, $R_3$ is absent, and $R_4$ is butoxy. In yet another embodiment, Y is N, $R_1$ is OH, $R_2$ is benzyl, $R_3$ is absent, and $R_4$ is benzylamino. In still yet another embodiment, Y is N, $R_1$ is OH, $R_2$ is benzyl, $R_3$ is absent, and $R_4$ is pentyl.

In one aspect, a compound that comprises a structure as in formula (VI):

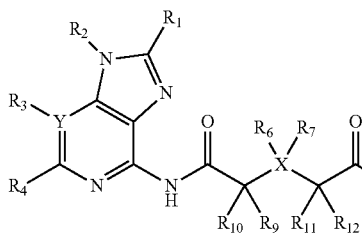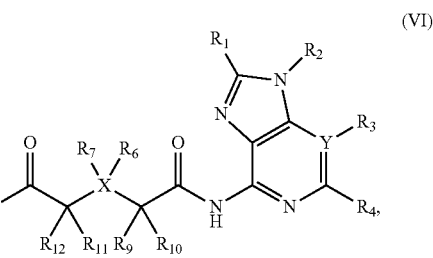

(VI)

wherein each $R_1$, independently, =H, OH, SH, NH$_2$, or substituted or unsubstituted alkyl, alkoxy, alkylthio, or alkylamino;

each $R_2$, independently, =H, alkyl, or substituted alkyl;

each Y, independently, =N or C;

each $R_3$, independently, is absent if Y=N; or is H, alkyl, substituted alkyl, or combined with $R_4$ to form a carbocycle or heterocycle with the carbon atoms of the pyridine ring to which they are connected if Y=C;

each $R_4$, independently, is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected;

each X, independently, is C, N, O, or S;

each $R_6$ and $R_7$, independently, are each independently H or substituted; and each $R_9$, $R_{10}$, $R_{11}$, and $R_{12}$, independently, are each independently H, a halogen, OH, thio, NH$_2$, or substituted or unsubstituted alkyl, aryl, heterocyclic, alkoxy, aryloxy, alkylthio, arylthio, alkylamino, or arylamino, is provided.

In one embodiment, the polymer is selected from the group consisting of polyketaldiols, poly(ethylene)glycol, polycaprolactone diol, diblock polylactide-co-poly(ethylene)glycol, diblock polylactide/polyglycolide-co-poly(ethylene)glycol, diblock polyglycolide-co-poly(ethylene)glycol, poly(propylene) glycol, poly(hexamethylene carbonate) diol, and poly(tetrahydrofuran). In another embodiment of this aspect, the polymer includes a unit of a polymer. In another embodiment, the polymer has a weight average molecular weight ranging from 800 Daltons to 10,000 Daltons, as determined using gel permeation chromatography. In a further embodiment, the polymer is insoluble in water at pH=7.4 and at 25° C. In yet another embodiment, the polymer does not comprise polyketal or unit thereof.

In one embodiment, $R_1$ is H, $R_2$ is isobutyl, Y is C, and $R_3$ and $R_4$ are combined to form a benzene ring with the carbon atoms of the pyridine ring to which they are connected. In another embodiment, $R_1$ is ethoxymethyl, $R_2$ is hydroxyisobutyl, Y=C, and $R_3$ and $R_4$ are combined to form a benzene ring with the carbon atoms of the pyridine ring to which they are connected. In yet another embodiment, $R_1$ is ethoxymethyl, $R_2$ is methanesulfonamidoisobutyl, Y=C, and $R_3$ and $R_4$ are combined to form a benzene ring with the carbon atoms of the pyridine ring to which they are connected. In still another embodiment, $R_1$ is OH, $R_2$ is benzyl, Y=N, $R_3$ is absent, and $R_4$ is butoxy. In a further embodiment, Y is N, $R_1$ is OH, $R_2$ is benzyl, $R_3$ is absent, and $R_4$ is butylamino. In still another embodiment, Y is N, $R_1$ is OH, $R_2$ is benzyl, $R_3$ is absent, and $R_4$ is butoxy. In a further embodiment, Y is N, $R_1$ is OH, $R_2$ is benzyl, $R_3$ is absent, and $R_4$ is benzylamino. In yet a further embodiment, Y is N, $R_1$ is OH, $R_2$ is benzyl, $R_3$ is absent, and $R_4$ is pentyl.

In one embodiment, a composition comprising the above compounds is provided. In another embodiment, the composition further comprises a pharmaceutically acceptable excipient.

In another embodiment, a synthetic nanocarrier that comprises any of the foregoing compounds is provided. In one embodiment, the synthetic nanocarrier further comprises a B cell antigen and/or a T cell antigen. In another embodiment, the synthetic nanocarrier further comprises an antigen presenting cell (APC) targeting feature. In still another embodiment, the synthetic nanocarrier is a dendrimer, buckyball, nanowire, peptide or protein-based nanoparticle, nanoparticle that comprises a combination of nanomaterials, spheroidal nanoparticle, cubic nanoparticle, pyramidal nanoparticle, oblong nanoparticle, cylindrical nanoparticle, or toroidal nanoparticle.

In one embodiment, a composition comprising any of the foregoing synthetic nanocarriers is provided. In one embodiment, the composition further comprises a pharmaceutically acceptable excipient.

In another embodiment, a composition comprising a vaccine comprising any of the foregoing compounds is provided. In yet another embodiment, a composition comprising a vaccine comprising any of the foregoing compositions is provided. In another embodiment, a composition comprising a vaccine comprising any of the foregoing synthetic nanocarriers is provided.

In another embodiment, a method comprising administering any of the foregoing compounds, compositions or synthetic nanocarriers to a subject is provided. In one embodiment, the method is one where an immune response is induced or enhanced in the subject.

In another aspect, a compound having a structure of any of the compounds provided herein is provided. Compositions, synthetic nanocarriers, and vaccines comprising any of the compounds provided are also provided.

In a further aspect, any of the methods of making a compound provided herein are also provided.

DETAILED DESCRIPTION

Figure 1:
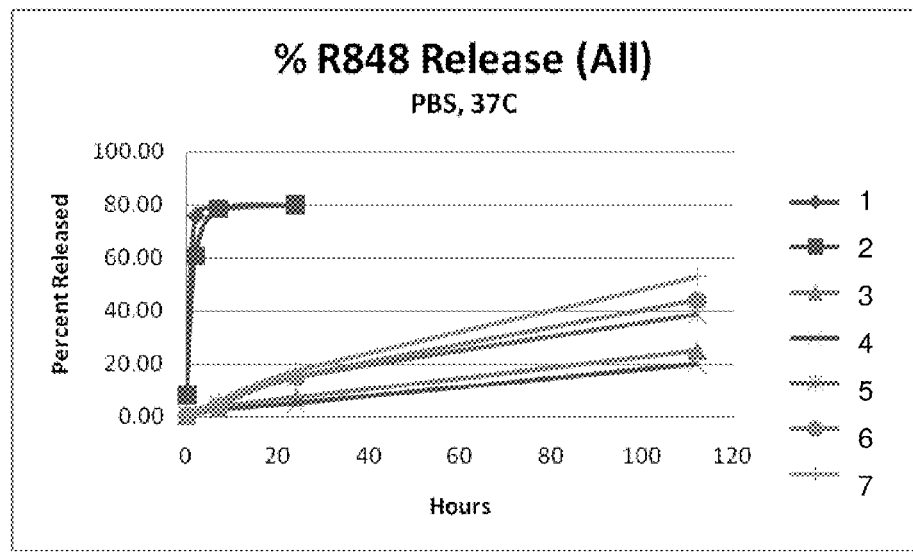
FIG. 1 shows the release of resiquimod (R848) from synthetic nanocarrier formulations at pH 7.4, 37° C.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules, reference to "a solvent" includes a mixture of two or more such solvents, reference to "an adhesive" includes mixtures of two or more such materials, and the like.

INTRODUCTION

The inventors have unexpectedly and surprisingly discovered that the problems and limitations noted above can be overcome by practicing the invention disclosed herein. In particular, the inventors have unexpectedly discovered that it is possible to provide compounds, together with related compositions and methods, that comprise:

a structure as in formula (I):

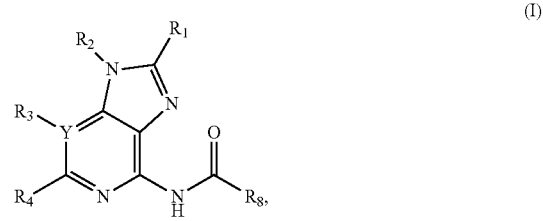

wherein $R_1$=H, OH, SH, $NH_2$, or substituted or unsubstituted alkyl, alkoxy, alkylthio, or alkylamino;

$R_2$=H, alkyl, or substituted alkyl;

Y=N or C;

$R_3$ is absent if Y=N; or is H, alkyl, substituted alkyl, or combined with $R_4$ to form a carbocycle or heterocycle with the carbon atoms of the pyridine ring to which they are connected if Y=C;

$R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; and $R_8$ is a biodegradable polymer or unit thereof.

When using synthetic nanocarriers to produce an immune response in a subject, it is advantageous to include with the synthetic nanocarriers an immunomodulatory agent. Such an agent includes agents that are immunomodulatory when uncoupled from the synthetic nanocarrier but may not exhibit immunomodulatory properties when coupled to the synthetic nanocarrier. It is particularly advantageous to include the immunomodulatory agent as part of the synthetic nanocarriers itself. To achieve this, the immunomodulatory agent may be covalently attached to an appropriate polymer or unit thereof. It follows that the compounds and conjugates provided herein, in some embodiments, comprise an immunomodulatory agent, which also is intended to include an agent that is immunomodulatory when uncoupled from the polymer or unit thereof but that may not exhibit immunomodulatory properties when coupled to the polymer or unit thereof. The compounds provided herein can be incorporated into one or more synthetic nanocarriers. The compounds are incorporated into synthetic nanocarriers by methods known in the art or described elsewhere herein.

In some embodiments, the polymer or unit thereof of the compounds or conjugates provided is a biodegradable polymer or unit thereof. The polymer or unit thereof, therefore, may comprise a polyester, polycarbonate, or polyamide, or unit thereof. It follows that the polymer or unit thereof may comprise poly(lactic acid), poly(glycolic acid), poly(lactic-co-glycolic acid), or polycaprolactone, or unit thereof. Generally, it is preferred that if the polymer comprises a polyether, such as poly(ethylene glycol) (PEG) or unit thereof, the polymer is a block-co-polymer of a polyether and a biodegradable polymer such that the polymer is biodegradable. In some embodiments, the polymer or unit thereof does not comprise a polyether, such as poly(ethylene glycol), or unit thereof. In other embodiments, the polymer does not solely comprise a polyether or unit thereof, such as poly(ethylene glycol), or unit thereof. Generally, for use as part of a synthetic nanocarrier the polymer of the compounds or conjugates provided herein is insoluble in water at pH=7.4 and at 25° C., is biodegradable, or both. In other embodiments, the polymer is insoluble in water at pH=7.4 and at 25° C. but soluble at pH=4.5 and at 25° C. In still other embodiments, the polymer is insoluble in water at pH=7.4 and at 25° C. but soluble at pH=4.5 and at 25° C. and biodegradable. The compounds, conjugates, and synthetic nanocarriers provided herein are unique in composition and are useful for the preparation of vaccines and associated materials.

Methods for making the aforementioned compounds are also provided. In embodiments, a method for making a conjugate that comprises a structure as in formula (I):

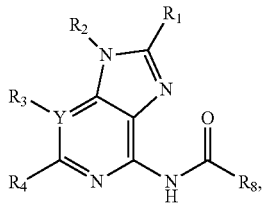

(I)

comprises:
activating a biodegradable polymer or unit thereof, and
exposing the activated biodegradable polymer or unit thereof and a compound comprising a structure as in formula (III) to a base and/or solvent:

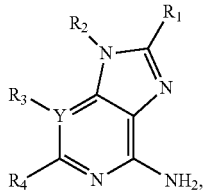

(III)

wherein $R_1$=H, OH, SH, $NH_2$, or substituted or unsubstituted alkyl, alkoxy, alkylthio, or alkylamino;
$R_2$=H, alkyl, or substituted alkyl;
Y=N or C;
$R_3$ is absent if Y=N; or is H, alkyl, substituted alkyl, or combined with $R_4$ to form a carbocycle or heterocycle with the carbon atoms of the pyridine ring to which they are connected if Y=C;
$R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; and
$R_8$ is a biodegradable polymer or unit thereof.

In other embodiments, a method for making a conjugate that comprises a structure as in formula (I):

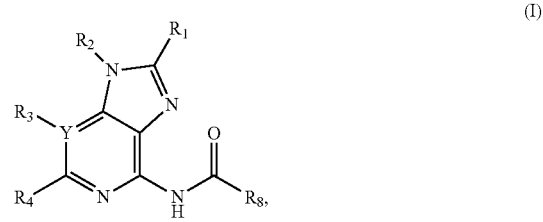

(I)

comprises:
exposing a composition comprising a polymer or unit thereof and a compound comprising a structure as in formula (III) to a coupling agent and base and/or solvent:

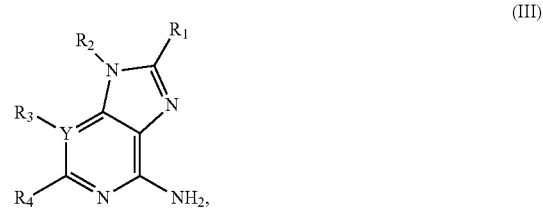

(III)

wherein $R_1$=H, OH, SH, $NH_2$, or substituted or unsubstituted alkyl, alkoxy, alkylthio, or alkylamino;
$R_2$=H, alkyl, or substituted alkyl;
Y=N or C;
$R_3$ is absent if Y=N; or is H, alkyl, substituted alkyl, or combined with $R_4$ to form a carbocycle or heterocycle with the carbon atoms of the pyridine ring to which they are connected if Y=C;
$R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; and
$R_8$ is a polymer or unit thereof.

The inventors have also unexpectedly discovered that it is possible to provide compounds, together with related compositions and methods, that comprise:
a structure as in formula (II):

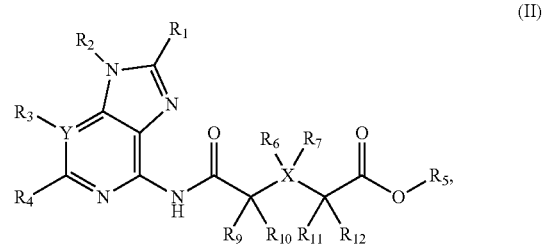

(II)

wherein $R_1$=H, OH, SH, $NH_2$, or substituted or unsubstituted alkyl, alkoxy, alkylthio, or alkylamino;

R$_2$=H, alkyl, or substituted alkyl;

Y=N or C;

R$_3$ is absent if Y=N; or is H, alkyl, substituted alkyl, or combined with R$_4$ to form a carbocycle or heterocycle with the carbon atoms of the pyridine ring to which they are connected if Y=C;

R$_4$ is H, or substituted or unsubstituted alkyl, alkoxy, alkylthio, or alkylamino when not combined with R$_3$ to form a carbocycle or heterocycle with the carbon atoms of the pyridine ring to which they are connected; or is combined with R$_3$ to form a carbocycle or heterocycle with the carbon atoms of the pyridine ring to which they are connected;

R$_5$ is a polymer or unit thereof;

X=C, N, O, or S;

R$_6$ and R$_7$ are each independently absent, H, or substituted; and

R$_9$, R$_{10}$, R$_{11}$, and R$_{12}$ are each independently H, a halogen, OH, thio, NH$_2$, or substituted or unsubstituted alkyl, aryl, heterocyclic, alkoxy, aryloxy, alkylthio, arylthio, alkylamino, or arylamino.

It has been discovered that it is possible to attach agents, such as immunomodulatory agents, comprising a structure as in formula (III), to a polymer or unit thereof with a terminal alcohol. Generally, terminal alcohols are less reactive, making attachment chemistry problematic. It has been found that imides, such as those comprising a structure as in formula (IV), will react with a terminal alcohol using catalysts commonly used in ring opening polymerizations. The resulting reaction product links the imide to the alcohol via an ester bond.

Accordingly, methods for making conjugates via the aforementioned chemistry are also provided. In some embodiments, a method for making a conjugate that comprises a structure as in formula (II):

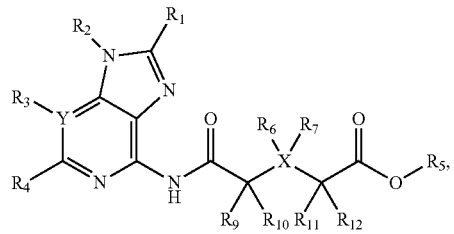

(II)

comprises:

combining an alcohol, a catalyst, and a compound comprising a structure as in formula (IV):

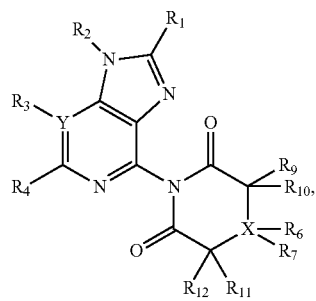

(IV)

wherein R$_1$=H, OH, SH, NH$_2$, or substituted or unsubstituted alkyl, alkoxy, alkylthio, or alkylamino;

R$_2$=H, alkyl, or substituted alkyl;

Y=N or C;

R$_3$ is absent if Y=N; or is H, alkyl, substituted alkyl, or combined with R$_4$ to form a carbocycle or heterocycle with the carbon atoms of the pyridine ring to which they are connected if Y=C;

R$_4$ is H, or substituted or unsubstituted alkyl, alkoxy, alkylthio, or alkylamino when not combined with R$_3$ to form a carbocycle or heterocycle with the carbon atoms of the pyridine ring to which they are connected; or is combined with R$_3$ to form a carbocycle or heterocycle with the carbon atoms of the pyridine ring to which they are connected;

R$_5$ is a polymer or unit thereof;

X is C, N, O, or S;

R$_6$ and R$_7$ are each independently H or substituted; and

R$_9$, R$_{10}$, R$_{11}$, and R$_{12}$ are each independently H, a halogen, OH, thio, NH$_2$, or substituted or unsubstituted alkyl, aryl, heterocyclic, alkoxy, aryloxy, alkylthio, arylthio, alkylamino, or arylamino; and heating the alcohol, catalyst, and compound.

In other embodiments, a method for making a conjugate that comprises a structure as in formula (II):

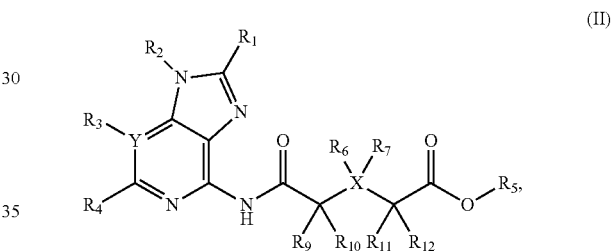

(II)

comprises:

combining an alcohol and a compound comprising a structure as in formula (IV):

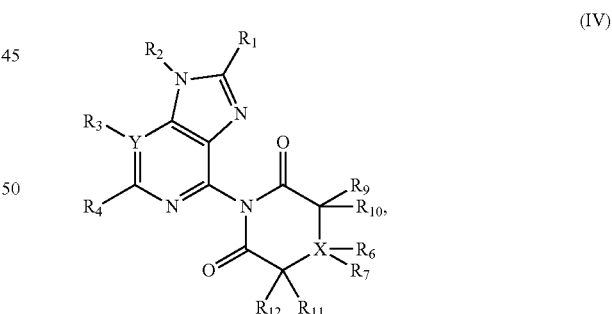

(IV)

wherein R$_1$=H, OH, SH, NH$_2$, or substituted or unsubstituted alkyl, alkoxy, alkylthio, or alkylamino;

R$_2$=H, alkyl, or substituted alkyl;

Y=N or C;

R$_3$ is absent if Y=N; or is H, alkyl, substituted alkyl, or combined with R$_4$ to form a carbocycle or heterocycle with the carbon atoms of the pyridine ring to which they are connected if Y=C;

R$_4$ is H, or substituted or unsubstituted alkyl, alkoxy, alkylthio, or alkylamino when not combined with R$_3$ to form a carbocycle or heterocycle with the carbon atoms of the pyridine ring to which they are connected; or is combined with R$_3$ to form a carbocycle or heterocycle with the carbon atoms of the pyridine ring to which they are connected;

R$_5$ is a polymer or unit thereof;

X is C, N, O, or S;

R$_6$ and R$_7$ are each independently H or substituted; and

R$_9$, R$_{10}$, R$_{11}$, and R$_{12}$ are each independently H, a halogen, OH, thio, NH$_2$, or substituted or unsubstituted alkyl, aryl, heterocyclic, alkoxy, aryloxy, alkylthio, arylthio, alkylamino, or arylamino;

heating the alcohol and compound; and adding a catalyst.

In yet other embodiments, a method for making a conjugate that comprises a structure as in formula (II):

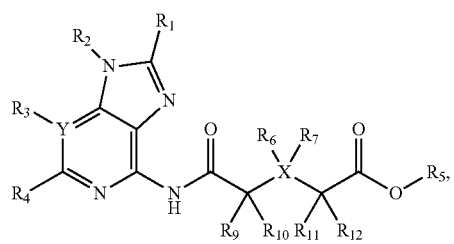

(II)

comprises:

combining an alcohol, a catalyst, and a compound comprising a structure as in formula (IV):

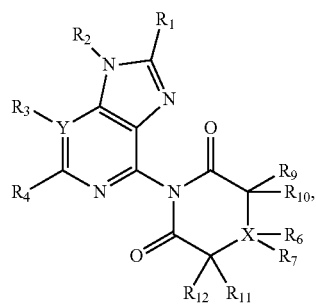

(IV)

wherein R$_1$=H, OH, SH, NH$_2$, or substituted or unsubstituted alkyl, alkoxy, alkylthio, or alkylamino;

R$_2$=H, alkyl, or substituted alkyl;

Y=N or C;

R$_3$ is absent if Y=N; or is H, alkyl, substituted alkyl, or combined with R$_4$ to form a carbocycle or heterocycle with the carbon atoms of the pyridine ring to which they are connected if Y=C;

R$_4$ is H, or substituted or unsubstituted alkyl, alkoxy, alkylthio, or alkylamino when not combined with R$_3$ to form a carbocycle or heterocycle with the carbon atoms of the pyridine ring to which they are connected; or is combined with R$_3$ to form a carbocycle or heterocycle with the carbon atoms of the pyridine ring to which they are connected;

R$_5$ is a polymer or unit thereof;

X is C, N, O, or S;

R$_6$ and R$_7$ are each independently H or substituted; and

R$_9$, R$_{10}$, R$_{11}$, and R$_{12}$ are each independently H, a halogen, OH, thio, NH$_2$, or substituted or unsubstituted alkyl, aryl, heterocyclic, alkoxy, aryloxy, alkylthio, arylthio, alkylamino, or arylamino.

Imides that may be used in the aforementioned reactions are also provided herein. In one embodiment, the imide compound comprises a structure as in formula (IV):

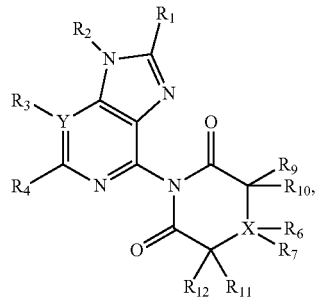

(IV)

wherein R$_1$=H, OH, SH, NH$_2$, or substituted or unsubstituted alkyl, alkoxy, alkylthio, or alkylamino;

R$_2$=H, alkyl, or substituted alkyl;

Y=N or C;

R$_3$ is absent if Y=N; or is H, alkyl, substituted alkyl, or combined with R$_4$ to form a carbocycle or heterocycle with the carbon atoms of the pyridine ring to which they are connected if Y=C;

R$_4$ is H, or substituted or unsubstituted alkyl, alkoxy, alkylthio, or alkylamino when not combined with R$_3$ to form a carbocycle or heterocycle with the carbon atoms of the pyridine ring to which they are connected; or is combined with R$_3$ to form a carbocycle or heterocycle with the carbon atoms of the pyridine ring to which they are connected;

X is C, N, O, or S;

R$_6$ and R$_7$ are each independently H or substituted; and

R$_9$, R$_{10}$, R$_{11}$, and R$_{12}$ are each independently H, a halogen, OH, thio, NH$_2$, or substituted or unsubstituted alkyl, aryl, heterocyclic, alkoxy, aryloxy, alkylthio, arylthio, alkylamino, or arylamino.

Such a compound can be made by methods that comprise combining, in the presence of a solvent and/or heat, with or without a dehydrating agent, such as a carboxylic acid anhydride or acetic anhydride, and a base, such as pyridine compound, a compound that comprises a structure as in formula (III):

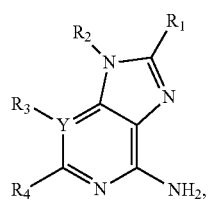

(III)

and a compound comprising a structure as in formula (V):

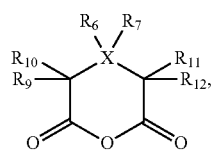

(V)

wherein $R_1$=H, OH, SH, $NH_2$, or substituted or unsubstituted alkyl, alkoxy, alkylthio, or alkylamino;

$R_2$=H, alkyl, or substituted alkyl;

Y=N or C;

$R_3$ is absent if Y=N; or is H, alkyl, substituted alkyl, or combined with $R_4$ to form a carbocycle or heterocycle with the carbon atoms of the pyridine ring to which they are connected if Y=C;

$R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected;

X is C, N, O, or S;

$R_6$ and $R_7$ are each independently H or substituted; and $R_9$, $R_{10}$, $R_{11}$, and $R_{12}$ are each independently H, a halogen, OH, thio, $NH_2$, or substituted or unsubstituted alkyl, aryl, heterocyclic, alkoxy, aryloxy, alkylthio, arylthio, alkylamino, or arylamino.

The inventors have also unexpectedly and surprisingly discovered that it is possible to make polymeric synthetic nanocarriers using polymers that have a weight average molecular weight ranging from about 800 Daltons to about 10,000 Daltons, as determined using gel permeation chromatography. In the formulation of polymeric synthetic nanocarriers, it has been generally believed that the molecular weight of polymers should be or exceed 10,000 Daltons. At times, it is advantageous to append to the polymers an immunomodulatory compound that can be released from the synthetic nanocarrier by a nonspecific degradation step within the body. If the synthetic nanocarriers are to be used to target the endosomal/lysosomal compartment, then it is particularly advantageous to have this degradation step occur preferentially at an acidic pH. One drawback to appending the immunomodulatory agent to the polymer is that the loading is diminished as the molecular weight of the polymer increases. In addition, as the molecular weight of the polymer increases so does the hydrophobicity of the polymer with the results that the degradation rate at a given pH can decrease. This leads to an undesirably decreased release rate of the immunomodulatory agent. Surprisingly, it has been found that low molecular weight polymers with a weight average molecular weight ranging from about 800 Daltons to about 10,000 Daltons form stable synthetic nanocarriers and that the rate of release of immunomodulatory agent from the synthetic nanocarrier is increased as the molecular weight decreases. The polymer of the compounds provided herein, therefore, in embodiments, have a weight average molecular weight ranging from about 800 Daltons to about 10,000 Daltons, and such compounds may be used to produce synthetic nanocarriers.

The compounds provided herein or the synthetic nanocarriers that comprise the compounds may also be pH sensitive (i.e., exhibit increased release of the immunomodulatory agent at or about a pH of 4.5 as compared to the release of the immunomodulatory agent at or about physiological pH (i.e., pH or 7.4). The property of having relatively low release of immunomodulatory agents at or about physiological pH but increased release at or about a pH of 4.5 is desirable for it targets the immunomodulatory agents to the endosomal/lysosomal compartment of, for example, antigen presenting cells (APCs) which tend to possess a pH that is at or about 4.5. This low pH level is found primarily in the upper gastrointestinal tract and endosome/lysosomes. Accordingly, unless the inventive compounds and compositions are administered via an oral route of administration, accelerated release at pH at or about 4.5 provides for an enhanced concentration of the immunomodulatory agent in the target compartment. Under these conditions, the immunomodulatory agent exhibits a pH sensitive dissociation and is then free to interact with receptors within the endosome/lysosome and stimulate a desired immune response. Additionally, because the coupling of the polymer may occur at a position on the immunomodulatory agent or compound of interest that, generally, substantially reduces or eliminates the biological activity of the immunomodulatory agent or compound of interest, the coupling can effectively produce a "pro-drug" like effect. This effect, in combination with accelerated release in conditions present in the endosome/lysosome, means that off-target effects (e.g., adverse events) are reduced and safety margins increased for compositions and vaccines that comprise the inventive compounds and compositions.

The present invention will now be described in more detail.

Definitions

"Administering" or "administration" means providing a compound, conjugate, synthetic nanocarrier, or composition provided herein to a patient in a manner that is pharmacologically useful.

"APC targeting feature" means one or more portions of which the inventive synthetic nanocarriers are comprised that target the synthetic nanocarriers to professional antigen presenting cells ("APCs"), such as but not limited to dendritic cells, SCS macrophages, follicular dendritic cells, and B cells. In embodiments, APC targeting features may comprise immunofeature surface(s) and/or targeting moieties that bind known targets on APCs. In embodiments, APC targeting features may comprise one or more B cell antigens present on a surface of synthetic nanocarriers. In embodiments, APC targeting features may also comprise one or more dimensions of the synthetic nanoparticles that is selected to promote uptake by APCs.

In embodiments, targeting moieties for known targets on macrophages ("Mphs") comprise any targeting moiety that specifically binds to any entity (e.g., protein, lipid, carbohydrate, small molecule, etc.) that is prominently expressed and/or present on macrophages (i.e., subcapsular sinus-Mph markers). Exemplary SCS-Mph markers include, but are not limited to, CD4 (L3T4, W3/25, T4); CD9 (p24, DRAP-1, MRP-1); CD11a (LFA-1α, α L Integrin chain); CD11b (αM Integrin chain, CR3, Mo1, C3niR, Mac-1); CD11c (αX Integrin, p150, 95, AXb2); CDw12 (p90-120); CD13 (APN, gp150, EC 3.4.11.2); CD14 (LPS-R); CD15 (X-Hapten, Lewis, X, SSEA-1, 3-FAL); CD15s (Sialyl Lewis X); CD15u (3' sulpho Lewis X); CD15su (6 sulpho-sialyl Lewis X); CD16a (FCRIIIA); CD16b (FcgRIIIb); CDw17 (Lactosylceramide, LacCer); CD18 (Integrin β2, CD11a,b,c β-subunit); CD26 (DPP IV ectoeneyme, ADA binding protein); CD29 (Platelet GPIIa, β-1 integrin, GP); CD31 (PECAM-1, Endocam); CD32 (FCγRII); CD33 (gp67); CD35 (CR1, C3b/C4b receptor); CD36 (GpIIIb, GPIV, PASIV); CD37 (gp52-40); CD38 (ADP-ribosyl cyclase, T10); CD39 (ATP-dehydrogenase, NTPdehydrogenase-1); CD40 (Bp50); CD43 (Sialophorin, Leukosialin); CD44 (EMCRII, H-CAM, Pgp-1); CD45 (LCA, T200, B220, Ly5); CD45RA; CD45RB; CD45RC; CD45RO (UCHL-1); CD46 (MCP); CD47 (gp42, IAP, OA3, Neurophillin); CD47R (MEM-133); CD48 (Blast-1, Hulym3, BCM-1, OX-45); CD49a (VLA-1α, α1 Integrin); CD49b (VLA-2α, gpla, α2 Integrin); CD49c (VLA-3α, α3 Integrin); CD49e (VLA-5α, α5

Integrin); CD49f (VLA-6α, α6 Integrin, gplc); LD50 (ICAM-3); CD51 (Integrin α, VNR-α, Vitronectin-Rα); CD52 (CAMPATH-1, HE5); CD53 (OX-44); CD54 (ICAM-1); CD55 (DAF); CD58 (LFA-3); CD59 (1F5Ag, H19, Protectin, MACIF, MIRL, P-18); CD60a (GD3); CD60b (9-O-acetyl GD3); CD61 (GP IIIa, β3 Integrin); CD62L (L-selectin, LAM-1, LECAM-1, MEL-14, Leu8, TQ1); CD63 (LIMP, MLA1, gp55, NGA, LAMP-3, ME491); CD64 (FcγRI); CD65 (Ceramide, VIM-2); CD65s (Sialylated-CD65, VIM2); CD72 (Ly-19.2, Ly-32.2, Lyb-2); CD74 (Ii, invariant chain); CD75 (sialo-masked Lactosamine); CD75S (α2,6 sialylated Lactosamine); CD80 (B7, B7-1, BB1); CD81 (TAPA-1); CD82 (4F9, C33, IA4, KAI1, R2); CD84 (p75, GR6); CD85a (ILT5, LIR2, HL9); CD85d (ILT4, LIR2, MIR10); CD85j (ILT2, LIR1, MIR7); CD85k (ILT3, LIR5, HM18); CD86 (B7-2/B70); CD87 (uPAR); CD88 (C5aR); CD89 (IgA Fc receptor, FcαR); CD91 (α2M-R, LRP); CDw92 (p70); CDw93 (GR11); CD95 (APO-1, FAS, TNFRSF6); CD97 (BL-KDD/F12); CD98 (4F2, FRP-1, RL-388); CD99 (MIC2, E2); CD99R (CD99 Mab restricted); CD100 (SEMA4D); CD101 (IGSF2, P126, V7); CD102 (ICAM-2); CD111 (PVRL1, HveC, PRR1, Nectin 1, HIgR); CD112 (HveB, PRR2, PVRL2, Nectin2); CD114 (CSF3R, G-CSRF, HG-CSFR); CD115 (c-fms, CSF-1R, M-CSFR); CD116 (GMCSFRα); CDw119 (IFNγR, IFNγRA); CD120a (TNFRI, p55); CD120b (TNFRII, p75, TNFR p80); CD121b (Type 2 IL-1R); CD122 (IL2Rβ); CD123 (IL-3Rα); CD124 (IL-4Rα); CD127 (p90, IL-7R, IL-7Rα); CD128a (IL-8Ra, CXCR1, (Tentatively renamed as CD181)); CD128b (IL-8Rb, CSCR2, (Tentatively renamed as CD182)); CD130 (gp130); CD131 (Common β subunit); CD132 (Common γ chain, IL-2Rγ); CDw136 (MSP-R, RON, p158-ron); CDw137 (4-1BB, ILA); CD139; CD141 (Thrombomodulin, Fetomodulin); CD147 (Basigin, EMMPRIN, M6, OX47); CD148 (HPTP-η, p260, DEP-1); CD155 (PVR); CD156a (CD156, ADAM8, MS2); CD156b (TACE, ADAM17, cSVP); CDw156C (ADAM10); CD157 (Mo5, BST-1); CD162 (PSGL-1); CD164 (MGC-24, MUC-24); CD165 (AD2, gp37); CD168 (RHAMM, IHABP, HMMR); CD169 (Sialoadhesin, Siglec-1); CD170 (Siglec 5); CD171 (L1CAM, NILE); CD172 (SIRP-1α, MyD-1); CD172b (SIRPβ); CD180 (RP105, Bgp95, Ly64); CD181 (CXCR1, (Formerly known as CD128a)); CD182 (CXCR2, (Formerly known as CD128b)); CD184 (CXCR4, NPY3R); CD191 (CCR1); CD192 (CCR2); CD195 (CCR5); CDw197 (CCR7 (was CDw197)); CDw198 (CCR8); CD204 (MSR); CD205 (DEC-25); CD206 (MMR); CD207 (Langerin); CDw210 (CK); CD213a (CK); CDw217 (CK); CD220 (Insulin R); CD221 (IGF1R); CD222 (M6P-R, IGFII-R); CD224 (GGT); CD226 (DNAM-1, PTA1); CD230 (Prion Protein (PrP)); CD232 (VESP-R); CD244 (2B4, P38, NAIL); CD245 (p220/240); CD256 (APRIL, TALL2, TNF (ligand) superfamily, member 13); CD257 (BLYS, TALL1, TNF (ligand) superfamily, member 13b); CD261 (TRAIL-R1, TNF-R superfamily, member 10a); CD262 (TRAIL-R2, TNF-R superfamily, member 10b); CD263 (TRAIL-R3, TNBF-R superfamily, member 10c); CD264 (TRAIL-R4, TNF-R superfamily, member 10d); CD265 (TRANCE-R, TNF-R superfamily, member 11a); CD277 (BT3.1, B7 family: Butyrophilin 3); CD280 (TEM22, ENDO180); CD281 (TLR1, TOLL-like receptor 1); CD282 (TLR2, TOLL-like receptor 2); CD284 (TLR4, TOLL-like receptor 4); CD295 (LEPR); CD298 (ATP1B3, Na K ATPase, β3 subunit); CD300a (CMRF-35H); CD300c (CMRF-35A); CD300e (CMRF-35L1); CD302 (DCL1); CD305 (LAIR1); CD312 (EMR2); CD315 (CD9P1); CD317 (BST2); CD321 (JAM1); CD322 (JAM2); CDw328 (Siglec7); CDw329 (Siglec9); CD68 (gp 110, Macrosialin); and/or mannose receptor; wherein the names listed in parentheses represent alternative names.

In embodiments, targeting moieties for known targets on dendritic cells ("DCs") comprise any targeting moiety that specifically binds to any entity (e.g., protein, lipid, carbohydrate, small molecule, etc.) that is prominently expressed and/or present on DCs (i.e., a DC marker). Exemplary DC markers include, but are not limited to, CD1a (R4, T6, HTA-1); CD1b (R1); CD1c (M241, R7); CD1d (R3); CD1e (R2); CD11b (αM Integrin chain, CR3, Mo1, C3niR, Mac-1); CD11c (αX Integrin, p150, 95, AXb2); CDw117 (Lactosylceramide, LacCer); CD19 (B4); CD33 (gp67); CD 35 (CR1, C3b/C4b receptor); CD 36 (GpIIIb, GPIV, PASIV); CD39 (ATPdehydrogenase, NTPdehydrogenase-1); CD40 (Bp50); CD45 (LCA, T200, B220, Ly5); CD45RA; CD45RB; CD45RC; CD45RO (UCHL-1); CD49d (VLA-4α, α4 Integrin); CD49e (VLA-5α, α5 Integrin); CD58 (LFA-3); CD64 (FcγRI); CD72 (Ly-19.2, Ly-32.2, Lyb-2); CD73 (Ecto-5'nucloticlease); CD74 (Ii, invariant chain); CD80 (B7, B7-1, BB1); CD81 (TAPA-1); CD83 (HB15); CD85a (ILT5, LIR3, HL9); CD85d (ILT4, LIR2, MIR10); CD85j (ILT2, LIR1, MIR7); CD85k (ILT3, LIR5, HM18); CD86 (B7-2/B70); CD88 (C5aR); CD97 (BL-KDD/F12); CD101 (IGSF2, P126, V7); CD116 (GM-CSFRα); CD120a (TMFRI, p55); CD120b (TNFRII, p75, TNFR p80); CD123 (IL-3Ra); CD139; CD148 (HPTP-η, DEP-1); CD150 (SLAM, IPO-3); CD156b (TACE, ADAM17, cSVP); CD157 (Mo5, BST-1); CD167a (DDR1, trkE, cak); CD168 (RHAMM, IHABP, HMMR); CD169 (Sialoadhesin, Siglec-1); CD170 (Siglec-5); CD171 (L1CAM, NILE); CD172 (SIRP-1α, MyD-1); CD172b (SIRPβ); CD180 (RP105, Bgp95, Ly64); CD184 (CXCR4, NPY3R); CD193 (CCR3); CD196 (CCR6); CD197 (CCR7 (ws CDw197)); CDw197 (CCR7, EBI1, BLR2); CD200 (OX2); CD205 (DEC-205); CD206 (MMR); CD207 (Langerin); CD208 (DC-LAMP); CD209 (DCSIGN); CDw218a (IL18Rα); CDw218b (IL8Rβ); CD227 (MUC1, PUM, PEM, EMA); CD230 (Prion Protein (PrP)); CD252 (OX40L, TNF (ligand) superfamily, member 4); CD258 (LIGHT, TNF (ligand) superfamily, member 14); CD265 (TRANCE-R, TNF-R superfamily, member 11a); CD271 (NGFR, p75, TNFR superfamily, member 16); CD273 (B7DC, PDL2); CD274 (B7H1, PDL1); CD275 (B7H2, ICOSL); CD276 (B7H3); CD277 (BT3.1, B7 family: Butyrophilin 3); CD283 (TLR3, TOLL-like receptor 3); CD289 (TLR9, TOLL-like receptor 9); CD295 (LEPR); CD298 (ATP1B3, Na K ATPase β3 submit); CD300a (CMRF-35H); CD300c (CMRF-35A); CD301 (MGL1, CLECSF14); CD302 (DCL1); CD303 (BDCA2); CD304 (BDCA4); CD312 (EMR2); CD317 (BST2); CD319 (CRACC, SLAMF7); CD320 (8D6); and CD68 (gp110, Macrosialin); class II MHC; BDCA-1; Siglec-H; wherein the names listed in parentheses represent alternative names.

In embodiments, targeting can be accomplished by any targeting moiety that specifically binds to any entity (e.g., protein, lipid, carbohydrate, small molecule, etc.) that is prominently expressed and/or present on B cells (i.e., B cell marker). Exemplary B cell markers include, but are not limited to, CD1c (M241, R7); CD1d (R3); CD2 (E-rosette R, T11, LFA-2); CD5 (T1, Tp67, Leu-1, Ly-1); CD6 (T12); CD9 (p24, DRAP-1, MRP-1); CD11a (LFA-1α, αL Integrin chain); CD11b (αM Integrin chain, CR3, Mo1, C3niR, Mac-1); CD11c (αX Integrin, P150, 95, AXb2); CDw17 (Lactosylceramide, LacCer); CD18 (Integrin β2, CD11a, b, c β-subunit); CD19 (B4); CD20 (B1, Bp35); CD21 (CR2, EBV-R, C3dR); CD22 (BL-CAM, Lyb8, Siglec-2); CD23

(FceRII, B6, BLAST-2, Leu-20); CD24 (BBA-1, HSA); CD25 (Tac antigen, IL-2Ra, p55); CD26 (DPP IV ectoeneyme, ADA binding protein); CD27 (T14, S152); CD29 (Platelet GPIIa, β-1 integrin, GP); CD31 (PECAM-1, Endocam); CD32 (FCγRII); CD35 (CR1, C3b/C4b receptor); CD37 (gp52-40); CD38 (ADPribosyl cyclase, T10); CD39 (ATPdehydrogenase, NTPdehydrogenase-1); CD40 (Bp50); CD44 (ECMRII, H-CAM, Pgp-1); CD45 (LCA, T200, B220, Ly5); CD45RA; CD45RB; CD45RC; CD45RO (UCHL-1); CD46 (MCP); CD47 (gp42, IAP, OA3, Neurophilin); CD47R (MEM-133); CD48 (Blast-1, Hulym3, BCM-1, OX-45); CD49b (VLA-2α, gpla, α2 Integrin); CD49c (VLA-3α, α3 Integrin); CD49d (VLA-4α, α4 Integrin); LD50 (ICAM-3); CD52 (CAMPATH-1, HES); CD53 (OX-44); CD54 (ICAM-1); CD55 (DAF); CD58 (LFA-3); CD60a (GD3); CD62L (L-selectin, LAM-1, LECAM-1, MEL-14, Leu8, TQ1); CD72 (Ly-19.2, Ly-32.2, Lyb-2); CD73 (Ecto-5'-nuciotidase); CD74 (Ii, invariant chain); CD75 (sialo-masked Lactosamine); CD75S (α2, 6 sialytated Lactosamine); CD77 (Pk antigen, BLA, CTH/Gb3); CD79a (Igα, MB1); CD79b (Igβ, B29); CD80; CD81 (TAPA-1); CD82 (4F9, C33, IA4, KAI1, R2); CD83 (HB15); CD84 (P75, GR6); CD85j (ILT2, LIR1, MIR7); CDw92 (p70); CD95 (APO-1, FAS, TNFRSF6); CD98 (4F2, FRP-1, RL-388); CD99 (MIC2, E2); CD100 (SEMA4D); CD102 (ICAM-2); CD108 (SEMA7A, JMH blood group antigen); CDw119 (IFNγR, IFNγRa); CD120a (TNFRI, p55); CD120b (TNFRII, p75, TNFR p80); CD121b (Type 2 IL-1R); CD122 (IL2Rβ); CD124 (IL-4Rα); CD130 (gp130); CD132 (Common γ chain, IL-2Rγ); CDw137 (4-1BB, ILA); CD139; CD147 (Basigin, EMMPRIN, M6, OX47); CD150 (SLAM, IPO-3); CD162 (PSGL-1); CD164 (MGC-24, MUC-24); CD166 (ALCAM, KG-CAM, SC-1, BEN, DM-GRASP); CD167a (DDR1, trkE, cak); CD171 (L1CMA, NILE); CD175s (Sialyl-Tn (S-Tn)); CD180 (RP105, Bgp95, Ly64); CD184 (CXCR4, NPY3R); CD185 (CXCR5); CD192 (CCR2); CD196 (CCR6); CD197 (CCR7 (was CDw197)); CDw197 (CCR7, EBI1, BLR2); CD200 (OX2); CD205 (DEC-205); CDw210 (CK); CD213a (CK); CDw217 (CK); CDw218a (IL18Rα); CDw218b (IL18Rβ); CD220 (Insulin R); CD221 (IGF1R); CD222 (M6P-R, IGFII-R); CD224 (GGT); CD225 (Leu13); CD226 (DNAM-1, PTA1); CD227 (MUC1, PUM, PEM, EMA); CD229 (Ly9); CD230 (Prion Protein (Prp)); CD232 (VESP-R); CD245 (p220/240); CD24? (CD3 Zeta Chain); CD261 (TRAIL-R1, TNF-R superfamily, member 10a); CD262 (TRAIL-R2, TNF-R superfamily, member 10b); CD263 (TRAIL-R3, TNF-R superfamily, member 10c); CD264 (TRAIL-R4, TNF-R superfamily, member 10d); CD265 (TRANCE-R, TNF-R superfamily, member 11a); CD267 (TACI, TNF-R superfamily, member 13B); CD268 (BAFFR, TNF-R superfamily, member 13C); CD269 (BCMA, TNF-R superfamily, member 16); CD275 (B7H2, ICOSL); CD277 (BT3.1.B7 family: Butyrophilin 3); CD295 (LEPR); CD298 (ATP1B3 Na K ATPase β3 subunit); CD300a (CMRF-35H); CD300c (CMRF-35A); CD305 (LAIR1); CD307 (IRTA2); CD315 (CD9P1); CD316 (EW12); CD317 (BST2); CD319 (CRACC, SLAMF7); CD321 (JAM1); CD322 (JAM2); CDw327 (Siglec6, CD33L); CD68 (gp 100, Macrosialin); CXCR5; VLA-4; class II MHC; surface IgM; surface IgD; APRL; and/or BAFF-R; wherein the names listed in parentheses represent alternative names. Examples of markers include those provided elsewhere herein.

In some embodiments, B cell targeting can be accomplished by any targeting moiety that specifically binds to any entity (e.g., protein, lipid, carbohydrate, small molecule, etc.) that is prominently expressed and/or present on B cells upon activation (i.e., activated B cell marker). Exemplary activated B cell markers include, but are not limited to, CD1a (R4, T6, HTA-1); CD1b (R1); CD15s (Sialyl Lewis X); CD15u (3' sulpho Lewis X); CD15su (6 sulpho-sialyl Lewis X); CD30 (Ber-H2, Ki-1); CD69 (AIM, EA 1, MLR3, gp34/28, VEA); CD70 (Ki-24, CD27 ligand); CD80 (B7, B7-1, BB1); CD86 (B7-2/B70); CD97 (BLKDD/F12); CD125 (IL-5Rα); CD126 (IL-6Rα); CD138 (Syndecan-1, Heparan sulfate proteoglycan); CD152 (CTLA-4); CD252 (OX40L, TNF(ligand) superfamily, member 4); CD253 (TRAIL, TNF(ligand) superfamily, member 10); CD279 (PD1); CD289 (TLR9, TOLL-like receptor 9); and CD312 (EMR2); wherein the names listed in parentheses represent alternative names. Examples of markers include those provided elsewhere herein.

"B cell antigen" means any antigen that naturally is or could be engineered to be recognized by a B cell, and triggers (naturally or being engineered as known in the art) an immune response in a B cell (e.g., an antigen that is specifically recognized by a B cell receptor on a B cell). In some embodiments, an antigen that is a T cell antigen is also a B cell antigen. In other embodiments, the T cell antigen is not also a B cell antigen. B cell antigens include, but are not limited to proteins, peptides, small molecules, and carbohydrates. In some embodiments, the B cell antigen is a non-protein antigen (i.e., not a protein or peptide antigen). In some embodiments, the B cell antigen is a carbohydrate associated with an infectious agent. In some embodiments, the B cell antigen is a glycoprotein or glycopeptide associated with an infectious agent. The infectious agent can be a bacterium, virus, fungus, protozoan, parasite or prion. In some embodiments, the B cell antigen is a poorly immunogenic antigen. In some embodiments, the B cell antigen is an abused substance or a portion thereof. In some embodiments, the B cell antigen is an addictive substance or a portion thereof. Addictive substances include, but are not limited to, nicotine, a narcotic, a cough suppressant, a tranquilizer, and a sedative. In some embodiments, the B cell antigen is a toxin, such as a toxin from a chemical weapon or natural sources, or a pollutant. The B cell antigen may also be a hazardous environmental agent. In other embodiments, the B cell antigen is an alloantigen, an allergen, a contact sensitizer, a degenerative disease antigen, a hapten, an infectious disease antigen, a cancer antigen, an atopic disease antigen, an addictive substance, a xenoantigen, or a metabolic disease enzyme or enzymatic product thereof.

"Biodegradable polymer" means a polymer that degrades over time when introduced into the body of a subject. Biodegradable polymers, include but are not limited to, polyesters, polycarbonates, polyketals, or polyamides. Such polymers may comprise poly(lactic acid), poly(glycolic acid), poly(lactic-co-glycolic acid), or polycaprolactone. In some embodiments, the biodegradable polymer comprises a block-co-polymer of a polyether, such as poly(ethylene glycol), and a polyester, polycarbonate, or polyamide, or other biodegradable polymer. In embodiments, the biodegradable polymer comprises a block-co-polymer of poly (ethylene glycol) and poly(lactic acid), poly(glycolic acid), poly(lactic-co-glycolic acid), or polycaprolactone. In some embodiments, however, the biodegradable polymer does not comprise a polyether, such as poly(ethylene glycol), or consist solely of the polyether. Generally, for use as part of a synthetic nanocarrier the biodegradable polymer is insoluble in water at pH=7.4 and at 25° C. The biodegradable polymer, in embodiments, have a weight average molecular weight ranging from about 800 to about 50,000

Daltons, as determined using gel permeation chromatography. In some embodiments, the weight average molecular weight is from about 800 Daltons to about 10,000 Daltons, preferably from 800 Daltons to 10,000 Daltons, as determined using gel permeation chromatography. In other embodiments, the weight average molecular weight is from 1000 Daltons to 10,000 Daltons, as determined by gel permeation chromatography. In an embodiment, the biodegradable polymer does not comprise polyketal or a unit thereof.

"Couple" or "Coupled" or "Couples" (and the like) means attached to a polymer or unit thereof or attached to or contained within the synthetic nanocarrier. In some embodiments, the covalent coupling is mediated by one or more linkers. In some embodiments, the coupling is non-covalent. In some embodiments, the non-covalent coupling is mediated by charge interactions, affinity interactions, metal coordination, physical adsorption, hostguest interactions, hydrophobic interactions, TT stacking interactions, hydrogen bonding interactions, van der Waals interactions, magnetic interactions, electrostatic interactions, dipole-dipole interactions, and/or combinations thereof. In embodiments, the coupling may arise in the context of encapsulation within the synthetic nanocarriers, using conventional techniques. Any of the aforementioned couplings may be arranged to be on a surface or within an inventive synthetic nanocarrier.

"Dosage form" means a compound, conjugate, synthetic nanocarrier, or composition provided herein in a medium, carrier, vehicle, or device suitable for administration to a subject.

"Encapsulate" means to enclose within a synthetic nanocarrier, preferably enclose completely within a synthetic nanocarrier. Most or all of a substance that is encapsulated is not exposed to the local environment external to the synthetic nanocarrier. Encapsulation is distinct from absorbtion, which places most or all of a substance on a surface of a synthetic nanocarrier, and leaves the substance exposed to the local environment external to the synthetic nanocarrier. In embodiments, the immunomodulatory agent or B cell and/or T cell antigen is encapsulated within the synthetic nanocarrier.

"Immunomodulatory agent" means an agent that modulates an immune response. "Modulate", as used herein, refers to inducing, enhancing, stimulating, or directing an immune response. Such agents include immunostimulatory agents that stimulate (or boost) an immune response to an antigen but is not an antigen or derived from an antigen. In some embodiments, the immunomodulatory agent is on the surface of the synthetic nanocarrier and/or is incorporated within the synthetic nanocarrier. In embodiments, the immunomodulatory agent is coupled to the synthetic nanocarrier via the polymer or unit thereof of the compounds or conjugates provided.

In some embodiments, all of the immunomodulatory agents of a synthetic nanocarrier are identical to one another. In some embodiments, a synthetic nanocarrier comprises a number of different types of immunomodulatory agents. In some embodiments, a synthetic nanocarrier comprises multiple individual immunomodulatory agents, all of which are identical to one another. In some embodiments, a synthetic nanocarrier comprises exactly one type of immunomodulatory agent. In some embodiments, a synthetic nanocarrier comprises exactly two distinct types of immunomodulatory agents. In some embodiments, a synthetic nanocarrier comprises greater than two distinct types of immunomodulatory agents.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheroidal synthetic nanocarrier, the maximum and minimum dimension of a synthetic nanocarrier would be substantially identical, and would be the size of its diameter. Similarly, for a cubic synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably at least 80%, more preferably at least 90%, of the synthetic nanocarriers in a sample, based on the total number of synthetic nanocarriers in the sample, is greater than 100 nm. In an embodiment, a maximum dimension of at least 75%, preferably at least 80%, more preferably at least 90%, of the synthetic nanocarriers in a sample, based on the total number of synthetic nanocarriers in the sample, is equal to or less than 5 µm. Preferably, a minimum dimension of at least 75%, preferably at least 80%, more preferably at least 90%, of the synthetic nanocarriers in a sample, based on the total number of synthetic nanocarriers in the sample, is equal to or greater than 110 nm, more preferably equal to or greater than 120 nm, more preferably equal to or greater than 130 nm, and more preferably still equal to or greater than 150 nm. Preferably, a maximum dimension of at least 75%, preferably at least 80%, more preferably at least 90%, of the synthetic nanocarriers in a sample, based on the total number of synthetic nanocarriers in the sample is equal to or less than 3 µm, more preferably equal to or less than 2 µm, more preferably equal to or less than 1 µm, more preferably equal to or less than 800 nm, more preferably equal to or less than 600 nm, and more preferably still equal to or less than 500 nm. In preferred embodiments, a maximum dimension of at least 75%, preferably at least 80%, more preferably at least 90%, of the synthetic nanocarriers in a sample, based on the total number of synthetic nanocarriers in the sample, is equal to or greater than 100 nm, more preferably equal to or greater than 120 nm, more preferably equal to or greater than 130 nm, more preferably equal to or greater than 140 nm, and more preferably still equal to or greater than 150 nm. Measurement of synthetic nanocarrier sizes is obtained by suspending the synthetic nanocarriers in a liquid (usually aqueous) media and using dynamic light scattering (e.g. using a Brookhaven ZetaPALS instrument).

"Pharmaceutically acceptable excipient" means a pharmacologically inactive substance added to an inventive compound, conjugate, synthetic nanocarrier or composition to further facilitate its administration. Examples, without limitation, of pharmaceutically acceptable excipients include calcium carbonate, calcium phosphate, various diluents, various sugars and types of starch, cellulose derivatives, gelatin, vegetable oils, and polyethylene glycols.

"Release Rate" means the rate that an entrapped immunomodulatory agent flows from a composition, such as a synthetic nanocarrier, into a surrounding media in an in vitro release test. First, the synthetic nanocarrier is prepared for the release testing by placing into the appropriate in vitro release media. This is generally done by exchanging the buffer after centrifugation to pellet the synthetic nanocarrier and reconstitution of the synthetic nanocarriers using a mild condition. The assay is started by placing the sample at 37° C. in an appropriate temperature-controlled apparatus. A sample is removed at various time points.

The synthetic nanocarriers are separated from the release media by centrifugation to pellet the synthetic nanocarriers. The release media is assayed for the immunomodulatory agent that has dispersed from the synthetic nanocarriers. The immunomodulatory agent is measured using HPLC to determine the content and quality of the immunomodulatory agent. The pellet containing the remaining entrapped immunomodulatory agent is dissolved in solvents or hydrolyzed by base to free the entrapped immunomodulatory agent from the synthetic nanocarriers. The pellet-containing immunomodulatory agent is then also measured by HPLC to determine the content and quality of the immunomodulatory agent that has not been released at a given time point.

The mass balance is closed between immunomodulatory agent that has been released into the release media and what remains in the synthetic nanocarriers. Data are presented as the fraction released or as the net release presented as micrograms released over time.

"Subject" means an animal, including mammals such as humans and primates; avians; domestic household or farm animals such as cats, dogs, sheep, goats, cattle, horses and pigs; laboratory animals such as mice, rats and guinea pigs; fish; and the like.

"Synthetic nanocarrier(s)" means a discrete object that is not found in nature, and that possesses at least one dimension that is less than or equal to 5 microns in size. Albumin nanoparticles are expressly included as synthetic nanocarriers.

Synthetic nanocarriers include the compounds and compositions provided herein and, therefore, can be polymeric nanoparticles. In some embodiments, synthetic nanocarriers can comprise one or more polymeric matrices. The synthetic nanocarriers, however, can also include other nanomaterials and may be, for example, lipid-polymer nanoparticles. In some embodiments, a polymeric matrix can be surrounded by a coating layer (e.g., liposome, lipid monolayer, micelle, etc.). In some embodiments, the synthetic nanocarrier is not a micelle. In some embodiments, a synthetic nanocarrier may comprise a core comprising a polymeric matrix surrounded by a lipid layer (e.g., lipid bilayer, lipid monolayer, etc.). In some embodiments, the various elements of the synthetic nanocarriers can be coupled with the polymeric matrix.

The synthetic nanocarriers may comprise one or more lipids. In some embodiments, a synthetic nanocarrier may comprise a liposome. In some embodiments, a synthetic nanocarrier may comprise a lipid bilayer. In some embodiments, a synthetic nanocarrier may comprise a lipid monolayer. In some embodiments, a synthetic nanocarrier may comprise a micelle. In some embodiments, a synthetic nanocarrier may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

The synthetic nanocarriers may comprise lipid-based nanoparticles, metallic nanoparticles, surfactant-based emulsions, dendrimers, buckyballs, nanowires, virus-like particles, peptide or protein-based particles (such as albumin nanoparticles). Synthetic nanocarriers may be a variety of different shapes, including but not limited to spheroidal, cubic, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published U.S. Patent Application 20060002852 to Saltzman et al., (3) the lithographically constructed nanoparticles of Published U.S. Patent Application 20090028910 to DeSimone et al., (4) the disclosure of WO 2009/051837 to von Andrian et al., or (5) the nanoparticles disclosed in Published U.S. Patent Application 2008/0145441 to Penades et al.

Synthetic nanocarriers according to the invention that have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In a preferred embodiment, synthetic nanocarriers according to the invention that have a minimum dimension of equal to or less than about 100 nm, preferably equal to or less than 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers may possess an aspect ratio greater than 1:1, 1:1.2, 1:1.5, 1:2, 1:3, 1:5, 1:7, or greater than 1:10.

In some embodiments, synthetic nanocarriers are spheres or spheroids. In some embodiments, synthetic nanocarriers are flat or plate-shaped. In some embodiments, synthetic nanocarriers are cubes or cubic. In some embodiments, synthetic nanocarriers are ovals or ellipses. In some embodiments, synthetic nanocarriers are cylinders, cones, or pyramids.

It is often desirable to use a population of synthetic nanocarriers that is relatively uniform in terms of size, shape, and/or composition so that each synthetic nanocarrier has similar properties. For example, at least 80%, at least 90%, or at least 95% of the synthetic nanocarriers may have a minimum dimension or maximum dimension that falls within 5%, 10%, or 20% of the average diameter or average dimension. In some embodiments, a population of synthetic nanocarriers may be heterogeneous with respect to size, shape, and/or composition.

Synthetic nanocarriers can be solid or hollow and can comprise one or more layers. In some embodiments, each layer has a unique composition and unique properties relative to the other layer(s). To give but one example, synthetic nanocarriers may have a core/shell structure, wherein the core is one layer (e.g., a polymeric core) and the shell is a second layer (e.g., a lipid bilayer or monolayer). Synthetic nanocarriers may comprise a plurality of different layers.

"T cell antigen" means any antigen that is recognized by and triggers an immune response in a T cell (e.g., an antigen that is specifically recognized by a T cell receptor on a T cell or an NKT cell via presentation of the antigen or portion thereof bound to a Class I or Class II major histocompatability complex molecule (MHC), or bound to a CD1 complex). In some embodiments, an antigen that is a T cell antigen is also a B cell antigen. In other embodiments, the T cell antigen is not also a B cell antigen. T cell antigens generally are proteins or peptides. T cell antigens may be an antigen that stimulates a CD8+ T cell response, a CD4+ T cell response, or both. The T cell antigens, therefore, in some embodiments can effectively stimulate both types of responses.

In some embodiments the T cell antigen is a T-helper antigen, which is a T cell antigen that can generate an augmented response to an unrelated B cell antigen through stimulation of T cell help. In embodiments, a T-helper antigen may comprise one or more peptides derived from tetanus toxoid, Epstein-Barr virus, influenza virus, respiratory syncytial virus, measles virus, mumps virus, rubella virus, cytomegalovirus, adenovirus, diphtheria toxoid, or a PADRE peptide. In other embodiments, a T-helper antigen may comprise one or more lipids, or glycolipids, including but not limited to: α-galactosylceramide (α-GalCer), α-linked glycosphingolipids (from *Sphingomonas* spp.), galactosyl diacylglycerols (from *Borrelia burgdorferi*), lypophosphoglycan (from *Leishmania donovani*), and phosphatidylinositol tetramannoside (PIM4) (from *Mycobacterium leprae*). For additional lipids and/or glycolipids useful as T-helper antigens, see V. Cerundolo et al., "Harnessing invariant NKT cells in vaccination strategies." Nature Rev Immun, 9:28-38 (2009). In embodiments, CD4+ T-cell antigens may be derivatives of a CD4+ T-cell antigen that is obtained from a source, such as a natural source. In such embodiments, CD4+ T-cell antigen sequences, such as those peptides that bind to MHC II, may have at least 70%, 80%, 90%, or 95% identity to the antigen obtained from the source. In embodiments, the T cell antigen, preferably a T-helper antigen, may be coupled to, or uncoupled from, a synthetic nanocarrier.

"Unit thereof" refers to a monomeric unit of a polymer, the polymer generally being made up of a series of linked monomers.

"Vaccine" means a composition of matter that improves the immune response to a particular pathogen or disease. A vaccine typically contains factors that stimulate a subject's immune system to recognize a specific antigen as foreign and eliminate it from the subject's body. A vaccine also establishes an immunologic 'memory' so the antigen will be quickly recognized and responded to if a person is re-challenged. Vaccines can be prophylactic (for example to prevent future infection by any pathogen), or therapeutic (for example a vaccine against a tumor specific antigen for the treatment of cancer). Vaccines according to the invention may comprise one or more of the compounds, conjugates, synthetic nanocarriers, or compositions provided herein.

Methods of Making the Inventive Compounds, Conjugates, or Synthetic Nanocarriers The immunomodulatory agent and polymers or unit thereof are coupled covalently via an amide or ester bond. In some embodiments, these conjugates form part of a synthetic nanocarrier. In general, a polymer, such as polylactide (PLA) or polylactide-co-glycolide (PLGA), can be conjugated with an immunostimulatory agent, such as resiquimod (also known as R848), in several ways. Methods for coupling are provided below and in the EXAMPLES.

The following methods or any step of the methods provided are exemplary and may be carried out under any suitable conditions. In some cases, the reaction or any step of the methods provided may be carried out in the presence of a solvent or a mixture of solvents. Non-limiting examples of solvents that may be suitable for use in the invention include, but are not limited to, p-cresol, toluene, xylene, mesitylene, diethyl ether, glycol, petroleum ether, hexane, cyclohexane, pentane, dichloromethane (or methylene chloride), chloroform, dioxane, tetrahydrofuran (THF), dimethyl sulfoxide (DMSO), dimethylformamide (DMF), ethyl acetate (EtOAc), triethylamine, acetonitrile, methyl-t-butyl ether (MTBE), N-methylpyrrolidone (NMP), dimethylacetamide (DMAC), isopropanol (IPA), mixtures thereof, or the like. In some cases, the solvent is selected from the group consisting of ethyl acetate, methylene chloride, THF, DMF, NMP, DMAC, DMSO, and toluene, or a mixture thereof.

A reaction or any step of the methods provided may be carried out at any suitable temperature. In some cases, a reaction or any step of the methods provided is carried out at about room temperature (e.g., about 25° C., about 20° C., between about 20° C. and about 25° C., or the like). In some cases, however, the reaction or any step of the methods provided may be carried out at a temperature below or above room temperature, for example, at about −20° C., at about −10° C., at about 0° C., at about 10° C., at about 30° C., about 40° C., about 50° C., about 60° C., about 70° C., about 80° C., about 90° C., about 100° C., about 120° C., about 140° C., about 150° C. or greater. In particular embodiments, the reaction or any step of the methods provided is conducted at temperatures between 0° C. and 120° C. In some embodiments, the reaction or any step of the methods provided may be carried out at more than one temperature (e.g., reactants added at a first temperature and the reaction mixture agitated at a second wherein the transition from a first temperature to a second temperature may be gradual or rapid).

The reaction or any step of the methods provided may be allowed to proceed for any suitable period of time. In some cases, the reaction or any step of the methods provided is allowed to proceed for about 10 minutes, about 20 minutes, about 30 minutes, about 40 minutes, about 50 minutes, about 1 hour, about 2 hours, about 4 hours, about 8 hours, about 12 hours, about 16 hours, about 24 hours, about 2 days, about 3 days, about 4 days, or more. In some cases, aliquots of the reaction mixture may be removed and analyzed at an intermediate time to determine the progress of the reaction or any step of the methods provided. In some embodiments, a reaction or any step of the methods provided may be carried out under an inert atmosphere in anhydrous conditions (e.g., under an atmosphere of nitrogen or argon, anhydrous solvents, etc.)

The reaction products and/or intermediates may be isolated (e.g., via distillation, column chromatography, extraction, precipitation, etc.) and/or analyzed (e.g., gas liquid chromatography, high performance liquid chromatography, nuclear magnetic resonance spectroscopy, etc.) using commonly known techniques. In some cases, a conjugate or synthetic nanocarrier that includes the conjugated may be analyzed to determine the loading of immunomodulatory agent, for example, using reverse phase HPLC.

The polymers may have any suitable molecular weight. For example, the polymers may have a low or high molecular weight. Non-limiting molecular weight values include 100 Da, 200 Da, 300 Da, 500 Da, 750 Da, 1000 Da, 2000 Da, 3000 Da, 4000 Da, 5000 Da, 6000 Da, 7000 Da, 8000 Da, 9000 Da, 10,000 Da, or greater. In some embodiments, the polymers have a weight average molecular weight of about 800 Da to about 10,000 Da. The molecular weight of a polymer may be determined using gel permeation chromatography.

Provided below are exemplary conjugation reactions that are not intended to be limiting.

Method 1

A polymer (e.g., PLA, PLGA) or unit thereof with at least one acid end groups is converted to a reactive acylating agent such as an acyl halide, acylimidazole, active ester, etc. using an activating reagent commonly used in amide synthesis.

In this two-step method, the resulting activated polymer or unit thereof (e.g., PLA, PLGA) is isolated and then reacted with an immunomodulatory agent (e.g., R848) in the presence of a base to give the desired conjugate (e.g., PLA-R848), for example, as shown in the following scheme:

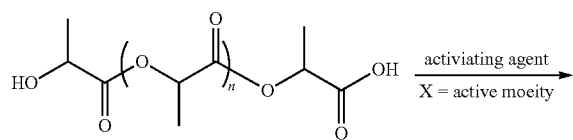

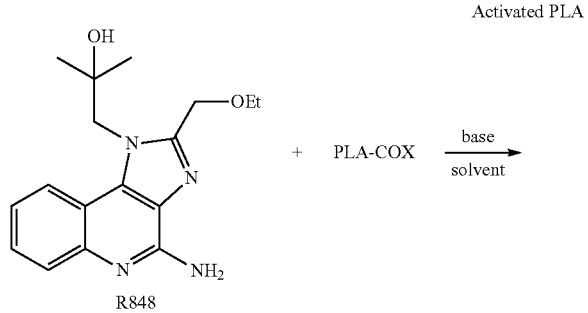

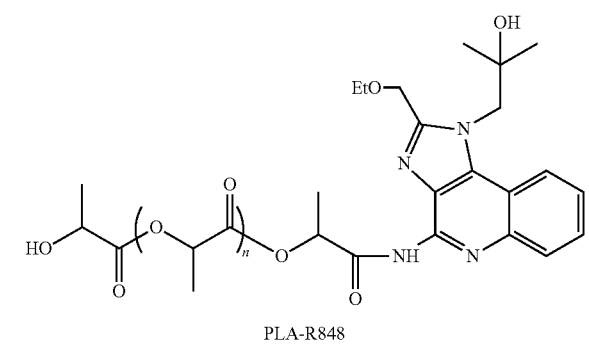

Activating reagents that can be used to convert polymers or units thereof, such as PLA or PLGA, to an activated acylating form include, but are not limited to cyanuric fluoride, N,N-tetramethylfluoroformamidinium hexafluorophosphate (TFFH); Acylimidazoles, such as carbonyl diimidazole (CDI), N,N'-carbonylbis(3-methylimidazolium) triflate (CBMIT); and Active esters, such as N-hydroxysuccinimide (NHS or HOSu) in the presence of a carbodiimide such as N,N'-dicyclohexylcarbodiimide (DCC), N-ethyl-N'-(3-(dimethylamino)propyl)carbodiimide hydrochloride (EDC) or N, N'-diisopropylcarbodiimide (DIC); N,N'-disuccinimidyl carbonate (DSC); pentafluorophenol in the presence of DCC or EDC or DIC; pentafluorophenyl trifluoroacetate.

The activated polymer or unit thereof may be isolated (e.g., via precipitation, extraction, etc.) and/or stored under suitable conditions (e.g., at low temperature, under argon) following activation, or may be used immediately. The activated polymer or unit thereof may be reacted with an immunostimulatory agent under any suitable conditions. In some cases, the reaction is carried out in the presence of a base and/or catalyst. Non-limiting examples of bases/catalysts include diisopropylethylamine (DIPEA) and 4-dimethylaminopyridine (DMAP).

Method 2

A polymer or unit thereof (e.g., PLA, PLGA having any suitable molecular weight) with an acid end group reacts with an immunomodulatory agent (e.g., R848) in the presence of an activating or coupling reagent, which converts the polymer or unit thereof (e.g., PLA, PLGA) to a reactive acylating agent in situ, to give the desired conjugate (e.g., PLA-R848, PLGA-R848).

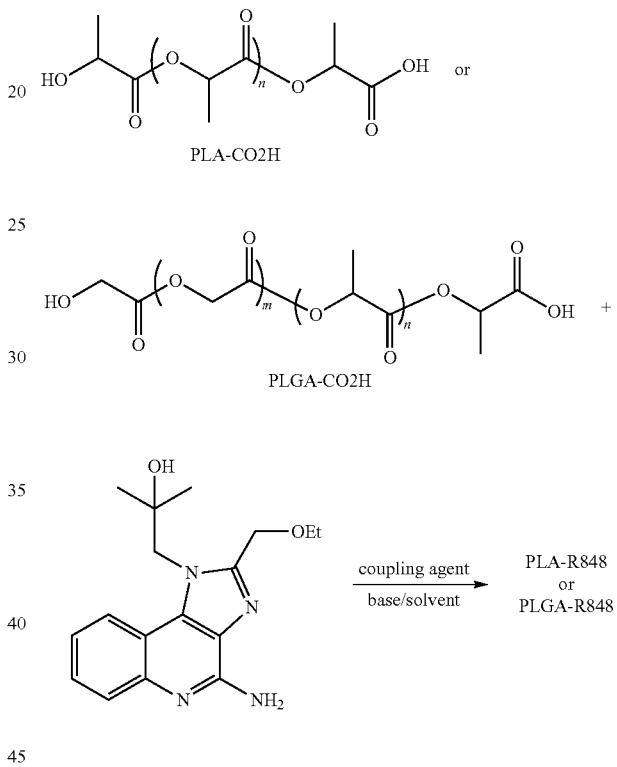

Coupling or activating agents include but are not limited to: activating agents used in the presence of an carbodiimide such as EDC or DCC or DIC, such as 1-Hydroxybenzotriazole (HOBt), 1-Hydroxy-7-azabenzotriazole (HOAt), 3,4-Dihydro-3-hydroxy-4-oxo-1,2,3-benzotriazine (HO-Dhbt), N-Hydroxysuccinimide (NHS or HOSu), Pentafluorophenol (PFP); Activating agents without carbodiimide: Phosphonium salts, such as O-Benzotriazol-1-yloxytris(dimethylamino) phosphonium hexafluorophosphate (BOP), O-Benzotriazol-1-yloxytris(pyrrolidino)phosphonium hexafluorophosphate (PyBOP), 7-Azabenzotriazol-1-yloxytris(pyrrolidino)phosphonium hexafluorophosphate (PyAOP); uronium salts such as O-Benzotriazol-1-yloxytris-1,1,3,3-tetramethyluronium tetrafluoroborate (TBTU) and hexafluorophosphate (HBTU), O-(7-Azabenzotriazol-1-yl)-1,1,3,3-tetramethyluronium hexafluorophosphate (HATU), O-(1,2-dihydro-2-oxo-1-pyridyl)-1,1,3,3-tetramethyl-uronium tetrafluoroborate (TPTU); Halouronium and halophosphonium salts such as bis(tetramethylene)fluoroformamidinium hexafluorophosphate (BTFFH), bromotris (dimethylamino) phosphonium hexafluorophosphate (BroP), bromotripyrrolidino phosphonium hexafluorophosphate (PyBroP) and chlorotripyrrolidino phosphonium hexafluorophosphate (PyClop); Benzotriazine derivatives such as O-(3,4-Dihydro-4-oxo-1,2,3-benzotriazine-3-yl)-N,N,N',N'-tetramethyluronium tetrafluoroborate (TDBTU) and 3-(diethyloxyphosphoryloxy)-1,2,3-benzotriazin-4 (3H)-one (DEPBT). Non-limiting examples of suitable solvents include DMF, DCM, toluene, ethyl acetate, etc., as described herein.

Method 3

Immunomodulatory agents, such as R848, can also be coupled to polymers or units thereof that are terminated in a hydroxyl group. Such polymers or units thereof include polyethylene glycol, polylactide, polylactide-co-glycolide, polycaprolactone, and other like polyesters, or units thereof. In general, the reaction proceeds as follows where an imide of the general structure (IV) will react with the terminal hydroxyl of the aforementioned polymers or units thereof using a catalyst used in lactone ring opening polymerizations. The resulting reaction product (II) links the amide of the agent to the polymer or unit thereof via an ester bond. The compounds of formula (IV) and (II) are as follows:

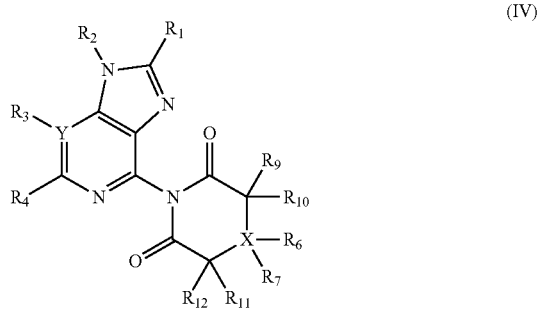

(IV)

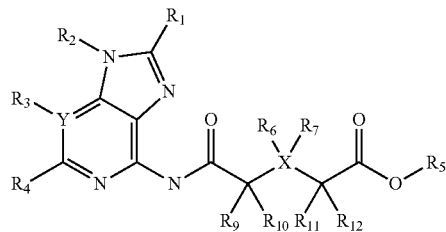

(II)

wherein $R_1$=H, OH, SH, $NH_2$, or substituted or unsubstituted alkyl, alkoxy, alkylthio, or alkylamino; $R_2$=H, alkyl, or substituted alkyl; Y=N or C; $R_3$ is absent if Y=N; or is H, alkyl, substituted alkyl, or combined with $R_4$ to form a carbocycle or heterocycle with the carbon atoms of the pyridine ring to which they are connected if Y=C; $R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected; $R_5$ is a polymer or unit thereof; X is C, N, O, or S; $R_6$ and $R_7$ are each independently H or substituted; and $R_9$, $R_{10}$, $R_{11}$, and $R_{12}$ are each independently H, a halogen, OH, thio, $NH_2$, or substituted or unsubstituted alkyl, aryl, heterocyclic, alkoxy, aryloxy, alkylthio, arylthio, alkylamino, or arylamino.

Catalysts include, but are not limited to, phosphazine bases, 1,8-diazabicycloundec-7-ene (DBU), 1,4,7-triazabicyclodecene (TBD), and N-methyl-1,4,7-triazabicyclodecene (MTDB). Other catalysts are known in the art and provided, for example, in Kamber et al., Organocatalytic Ring-Opening Polymerization, *Chem. Rev.* 2007, 107, 58-13-5840. Non-limiting examples of suitable solvents include methylene chloride, chloroform, and THF.

A specific example of a reaction completed by such a method is shown here:

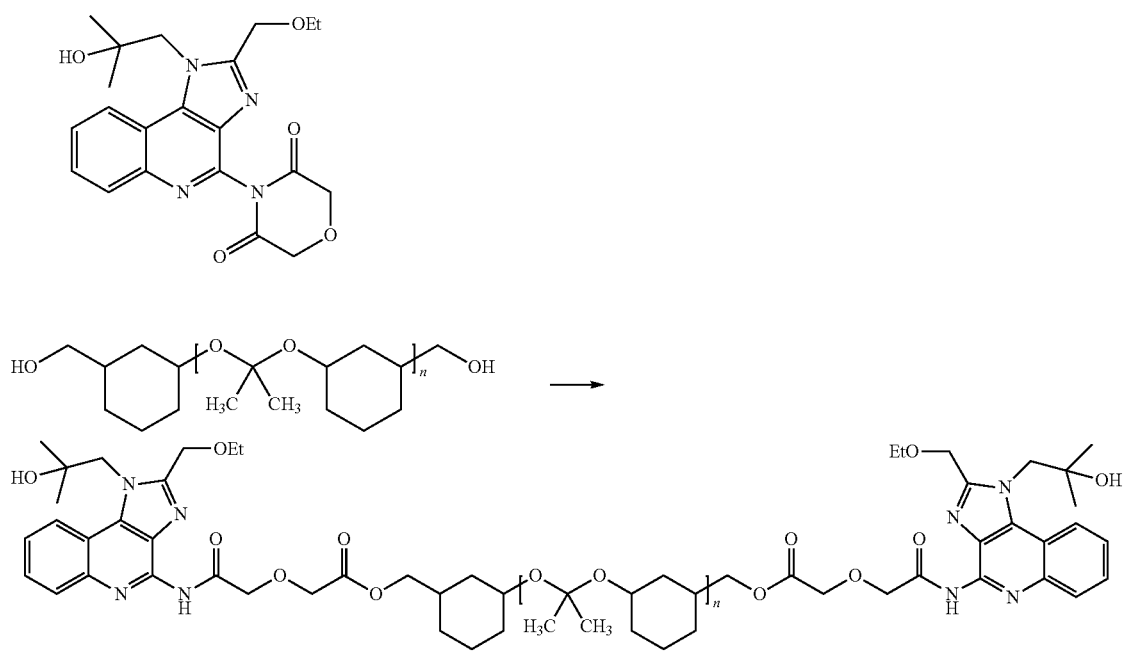

wherein R₅—OH contains two hydroxyl groups (e.g., a diol, HO—R₅—OH), each of which are functionalized by reaction with an imide associated with R848. In some cases, HO—R₅—OH is a poly-diol such as poly(hexamethyl carbonate) diol or polycaprolactone diol. For example, the reaction may be carried out as follows:

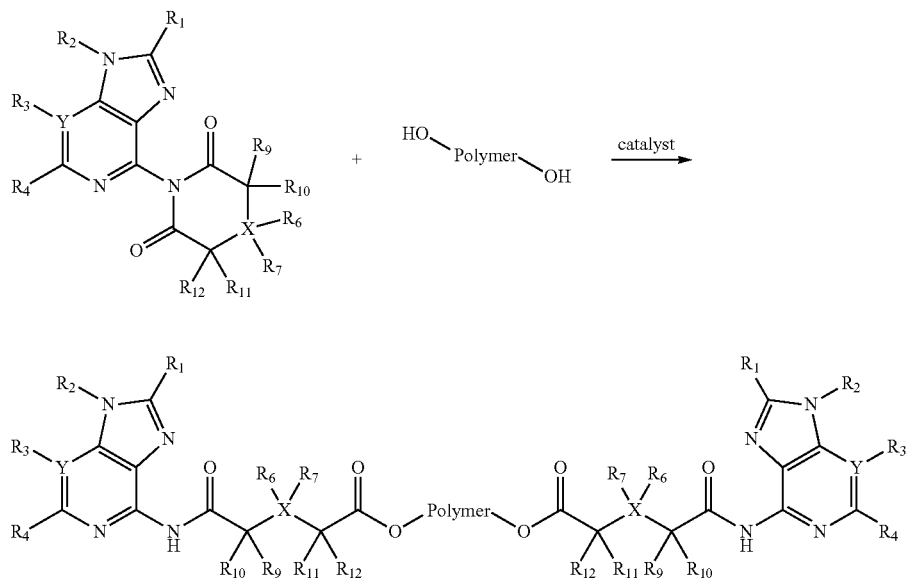

wherein the R groups are as described herein. Non-limiting examples of suitable polymers include polyketaldiols, poly(ethylene)glycol, polycaprolactone diol, diblock polylactide-co-poly(ethylene)glycol, diblock polylactide/ polyglycolide-co-poly(ethylene)glycol, diblock polyglycolide-co-poly(ethylene)glycol, poly(propylene) glycol, poly(hexamethylene carbonate)diol, and poly(tetrahydrofuran).

In embodiments where a poly-diol is employed, one of the diol groups may be protected with a protecting group (e.g., t-butyloxycarbonyl), thus the poly-diol would be a compound of formula HO—R₅—OP, wherein P is a protecting group. Following reaction with an immunomodulatory agent to form a immunomodulatory agent-R₅—OP conjugate, the protecting group may be removed and the second diol group may be reacted with any suitable reagent (e.g., PLGA, PLA).

Method 4

A conjugate (e.g., R848-PLA) can be formed via a one-pot ring-opening polymerization of an immunomodulatory agent (e.g., R848) with a polymer or unit thereof (e.g., D/L-lactide) in the presence of a catalyst, for example, as shown in the following scheme:

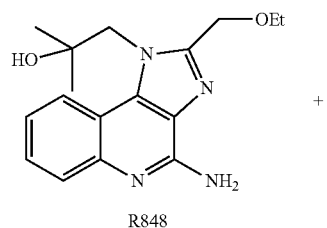

R848

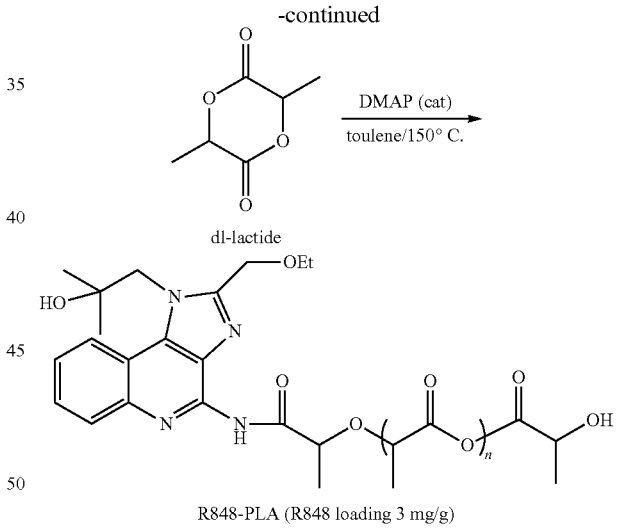

R848-PLA (R848 loading 3 mg/g)

In a one-step procedure, the immunomodulatory agent and the polymer or unit thereof may be combined into a single reaction mixture comprising a catalyst. The reaction may proceed at a suitable temperature (e.g., at about 150° C.) and the resulting conjugate may be isolated using commonly known techniques. Non-limiting examples of suitable catalysts include DMAP and tin ethylhexanoate.

Method 5

A conjugate can be formed via two-step ring opening polymerization of an immunomodulatory agent (e.g., R848) with one or more polymers or units thereof (e.g., D/L-lactide and glycolide) in the presence of a catalyst, for example, as shown in the following scheme:

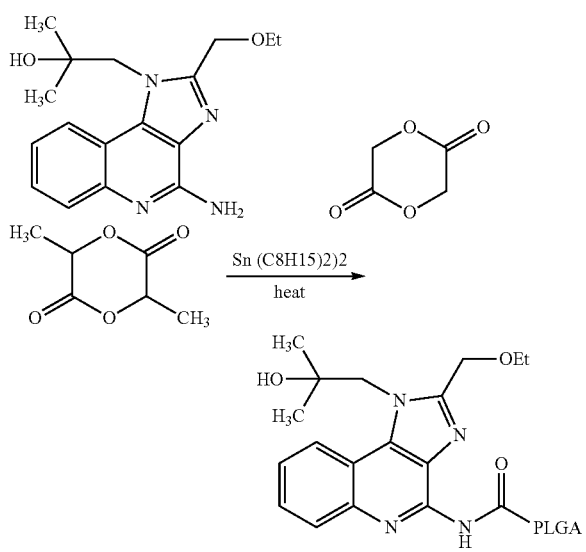

The polymers or units thereof may be first combined, and in some cases, heated (e.g., to 135° C.) to form a solution. The immunomodulatory agent may be added to a solution comprising the polymers or units thereof, followed by addition of a catalyst (e.g., tin ethylhexanoate). The resulting conjugate may be isolated using commonly known techniques. Non-limiting examples of suitable catalysts include DMAP and tin ethylhexanoate.

In some embodiments, a compound or conjugate provided herein, another immunomodulatory agent, antigen, and/or targeting moiety can be covalently associated with a polymeric matrix. In some embodiments, covalent association is mediated by a linker. In some embodiments, a compound or conjugate provided herein, another immunomodulatory agent, antigen, and/or targeting moiety can be noncovalently associated with a polymeric matrix. For example, in some embodiments, a compound or conjugate provided herein, another immunomodulatory agent, antigen, and/or targeting moiety can be encapsulated within, surrounded by, and/or dispersed throughout a polymeric matrix. Alternatively or additionally, a compound or conjugate provided herein, another immunomodulatory agent, antigen, and/or targeting moiety can be associated with a polymeric matrix by hydrophobic interactions, charge interactions, van der Waals forces, etc.

A wide variety of polymers and methods for forming polymeric matrices therefrom are known conventionally. In general, a polymeric matrix comprises one or more polymers. Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

Examples of polymers suitable for use in the present invention include, but are not limited to polyethylenes, polycarbonates (e.g., poly(1,3-dioxan-2one)), polyanhydrides (e.g., poly(sebacic anhydride)), polyhydroxyacids (e.g., poly(β-hydroxyalkanoate)), polypropylfumerates, polycaprolactones, polyamides (e.g., polycaprolactam), polyacetals, polyethers, polyesters (e.g., polylactide, polyglycolide), poly(orthoesters), polycyanoacrylates, polyvinyl alcohols, polyurethanes, polyphosphazenes, polyacrylates, polymethacrylates, polyureas, polystyrenes, polyamines, and polysaccharides (e.g., chitosan).

In some embodiments, polymers in accordance with the present invention include polymers which have been approved for use in humans by the U.S. Food and Drug Administration (FDA) under 21 C.F.R. §177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly (sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a synthetic nanocarrier comprising a hydrophilic polymeric matrix generates a hydrophilic environment within the synthetic nanocarrier. In some embodiments, polymers can be hydrophobic. In some embodiments, a synthetic nanocarrier comprising a hydrophobic polymeric matrix generates a hydrophobic environment within the synthetic nanocarrier. Selection of the hydrophilicity or hydrophobicity of the polymer may have an impact on the nature of materials that are incorporated (e.g., coupled) within the synthetic nanocarrier.

In some embodiments, polymers may be modified with one or more moieties and/or functional groups. A variety of moieties or functional groups can be used in accordance with the present invention. In some embodiments, polymers may be modified with PEG, with a carbohydrate, and/or with acyclic polyacetals derived from polysaccharides (Papisov, 2001, ACS Symposium Series, 786:301).

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, polyanhydrides, poly(ortho ester), poly(ortho ester)-PEG copolymers, poly(caprolactone), poly(caprolactone)-PEG copolymers, polylysine, polylysine-PEG copolymers, poly(ethyleneimine), poly(ethylene imine)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g., DNA, RNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that inventive compounds and synthetic nanocarriers may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In some embodiments, synthetic nanocarriers may comprise metal particles, quantum dots, ceramic particles, etc.

In some embodiments, synthetic nanocarriers may optionally comprise one or more amphiphilic entities. In some embodiments, an amphiphilic entity can promote the production of synthetic nanocarriers with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making synthetic nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of synthetic nanocarriers to be used in accordance with the present invention.

In some embodiments, synthetic nanocarriers may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan. In certain embodiments, the carbohydrate is a sugar alcohol, including but not limited to mannitol, sorbitol, xylitol, erythritol, maltitol, and lactitol.

Synthetic nanocarriers may be prepared using a wide variety of methods known in the art. For example, synthetic nanocarriers can be formed by methods as nanoprecipitation, flow focusing using fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755, and also U.S. Pat. Nos. 5,578,325 and 6,007,845).

In certain embodiments, synthetic nanocarriers are prepared by a nanoprecipitation process or spray drying. Conditions used in preparing synthetic nanocarriers may be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used may depend on the materials to be coupled to the synthetic nanocarriers and/or the composition of the polymer matrix.

If particles prepared by any of the above methods have a size range outside of the desired range, particles can be sized, for example, using a sieve.

Coupling can be achieved in a variety of different ways, and can be covalent or non-covalent. Such couplings may be arranged to be on a surface or within an inventive synthetic nanocarrier. Elements of the inventive synthetic nanocarriers (such as moieties of which an immunofeature surface is comprised, targeting moieties, polymeric matrices, and the like) may be directly coupled with one another, e.g., by one or more covalent bonds, or may be coupled by means of one or more linkers. Additional methods of functionalizing synthetic nanocarriers may be adapted from Published US Patent Application 2006/0002852 to Saltzman et al., Published US Patent Application 2009/0028910 to DeSimone et al., or Published International Patent Application WO/2008/127532 A1 to Murthy et al.

Any suitable linker can be used in accordance with the present invention. Linkers may be used to form amide linkages, ester linkages, disulfide linkages, etc. Linkers may contain carbon atoms or heteroatoms (e.g., nitrogen, oxygen, sulfur, etc.). In some embodiments, a linker is an aliphatic or heteroaliphatic linker. In some embodiments, the linker is a polyalkyl linker. In certain embodiments, the linker is a polyether linker. In certain embodiments, the linker is a polyethylene linker. In certain specific embodiments, the linker is a polyethylene glycol (PEG) linker.

In some embodiments, the linker is a cleavable linker. To give but a few examples, cleavable linkers include protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers (e.g., esterase cleavable linker), ultrasound-sensitive linkers, x-ray cleavable linkers, etc. In some embodiments, the linker is not a cleavable linker.

A variety of methods can be used to couple a linker or other element of a synthetic nanocarrier with the synthetic nanocarrier. General strategies include passive adsorption (e.g., via electrostatic interactions), multivalent chelation, high affinity non-covalent binding between members of a specific binding pair, covalent bond formation, etc. (Gao et al., 2005, Curr. Op. Biotechnol., 16:63). In some embodiments, click chemistry can be used to associate a material with a synthetic nanocarrier.

Non-covalent specific binding interactions can be employed. For example, either a particle or a biomolecule can be functionalized with biotin with the other being functionalized with streptavidin. These two moieties specifically bind to each other noncovalently and with a high affinity, thereby associating the particle and the biomolecule. Other specific binding pairs could be similarly used. Alternately, histidine-tagged biomolecules can be associated with particles conjugated to nickel-nitrolotriaceteic acid (Ni-NTA).

For additional general information on coupling, see the journal Bioconjugate Chemistry, published by the American Chemical Society, Columbus Ohio, PO Box 3337, Columbus, Ohio, 43210; "Cross-Linking," Pierce Chemical Technical Library, available at the Pierce web site and originally published in the 1994-95 Pierce Catalog, and references cited therein; Wong S S, Chemistry of Protein Conjugation and Cross-linking, CRC Press Publishers, Boca Raton, 1991; and Hermanson, G. T., Bioconjugate Techniques, Academic Press, Inc., San Diego, 1996.

It is to be understood that the compositions of the invention can be made in any suitable manner, and the invention is in no way limited to compositions that can be produced using the methods described herein. Selection of an appropriate method may require attention to the properties of the particular moieties being associated.

Pharmaceutical Compositions and Methods of Use

Compositions according to the invention comprise inventive compounds, conjugates, or synthetic nanocarriers, optionally, in combination with pharmaceutically acceptable excipients. The compositions may be made using conventional pharmaceutical manufacturing and compounding techniques to arrive at useful dosage forms. In an embodiment, inventive compounds, conjugates, synthetic nanocarriers, or compositions are suspended in sterile saline solution for injection together with a preservative.

In some embodiments, inventive compounds, conjugates, synthetic nanocarriers, or compositions are manufactured under sterile conditions or are terminally sterilized. This can ensure that resulting compositions are sterile and non-infectious, thus improving safety when compared to non-sterile compositions. This provides a valuable safety measure, especially when subjects receiving inventive compounds, conjugates, synthetic nanocarriers, or compositions have immune defects, are suffering from infection, and/or are susceptible to infection. In some embodiments, inventive compounds, conjugates, synthetic nanocarriers, or compositions may be lyophilized and stored in suspension or as lyophilized powder depending on the formulation strategy for extended periods without losing activity.

The inventive compounds, conjugates, synthetic nanocarriers, or compositions may be administered by a variety of routes of administration, including but not limited to parenteral, subcutaneous, intramuscular, intradermal, oral, intranasal, transmucosal, rectal; ophthalmic, transdermal, transcutaneous or by a combination of these routes.

The inventive compounds, conjugates, synthetic nanocarriers, or compositions and methods described herein can be used to induce, enhance, stimulate, modulate, or direct an immune response. The inventive compounds, conjugates, synthetic nanocarriers, or compositions and methods described herein can be used in the diagnosis, prophylaxis and/or treatment of conditions such as cancers, infectious diseases, metabolic diseases, degenerative diseases, inflammatory diseases, immunological diseases, or other disorders and/or conditions. The inventive compounds, conjugates, synthetic nanocarriers, or compositions and methods described herein can also be used for the prophylaxis or treatment of an addiction, such as an addiction to nicotine or a narcotic. The inventive compounds, conjugates, synthetic nanocarriers, or compositions and methods described herein can also be used for the prophylaxis and/or treatment of a condition resulting from the exposure to a toxin, hazardous substance, environmental toxin, or other harmful agent.

EXAMPLES

Example 1: One-Pot Ring-Opening Polymerization of R848 with D/L-Lactide in the Presence of a Catalyst

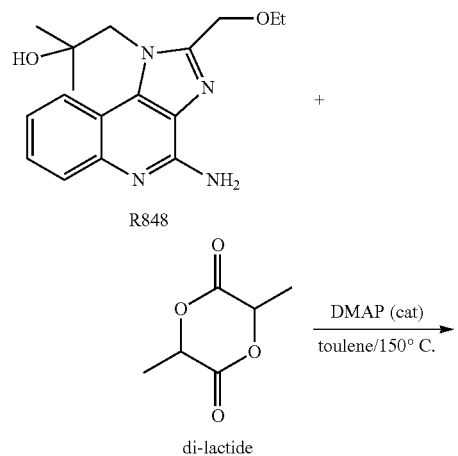

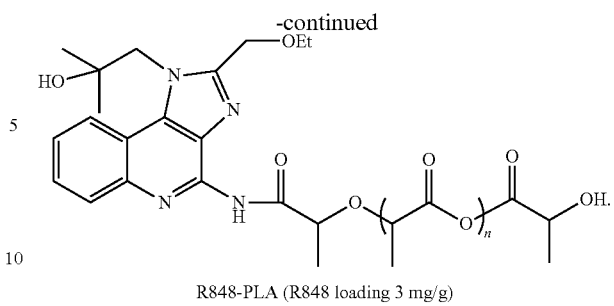

R848-PLA (R848 loading 3 mg/g)

A mixture of R848 (0.2 mmol, 63 mg), D/L-lactide (40 mmol, 5.8 g), and 4-dimethylaminopyridine (DMAP) (50 mg, 0.4 mmol) in 2 mL of anhydrous toluene was heated slowly to 150° C. (oil bath temperature) and maintained at this temperature for 18 h (after 3 hr, no R848 was left). The mixture was cooled to ambient temperature and the resulting mixture was quenched with water (50 mL) to precipitate out the resulting polymer, R848-PLA. The polymer was then washed sequentially with 45 mL each of MeOH, iPrOH, and ethyl ether. The polymer was dried under vacuum at 30° C. to give an off-white puffy solid (5.0 g). Polymeric structure was confirmed by $^1$H NMR in CDCl$_3$. A small sample of the polymer was treated with 2 N NaOH aq in THF/MeOH to determine the loading of R848 on the polymer by reverse phase HPLC. The loading of R848 is 3 mg per gram of polymer (0.3% loading-27.5% of theory).

Example 2: Two Step Ring Opening Polymerization of R848 with D/L-Lactide and Glycolide

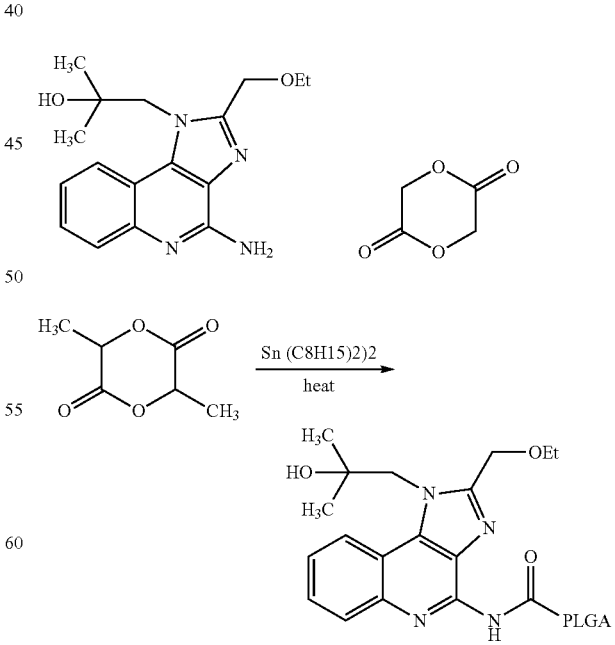

A mixture of D/L-lactide (10.8 g, 0.075 moles) and glycolide (2.9 g, 0.025 moles) was heated to 135° C. under argon. Once all of the materials had melted and a clear solution had resulted, R848 (1.08 g, 3.43×10⁻³ moles) was added. This solution was stirred at 135° C. under a slow stream of argon for one hour. Tin ethylhexanoate (150 μL) was added and heating was continued for 4 hours. After cooling, the solid pale brown mass was dissolved in methylene chloride (250 mL) and the solution was washed with 5% tartaric acid solution (2×200 mL). The methylene chloride solution was dried over magnesium sulfate, filtered, and then concentrated under vacuum. The residue was dissolved in methylene chloride (20 mL) and 2-propanol (250 mL) was added with stirring. The polymer that separated was isolated by decantation of the 2-propanol and was dried under high vacuum. NMR showed that the polymer was 71.4% lactide and 28.6% glycolide with a molecular weight of 4000. The loading of R848 was close to theoretical by NMR.

50-55° C. overnight (about 16 h). After cooling, the mixture was diluted with EtOAc (200 mL) and washed with saturated NH$_4$Cl solution (2×40 mL), water (40 mL) and brine solution (40 mL). The solution was dried over Na$_2$SO$_4$ (20 g) and concentrated to a gel-like residue. Isopropyl alcohol (IPA) (300 mL) was then added and the polymer conjugate precipitated out of solution. The polymer was then washed with IPA (4×50 mL) to remove residual reagents and dried under vacuum at 35-40° C. for 3 days as a white powder (10.26 g, MW by GPC is 5200, R848 loading is 12% by HPLC).

Example 4: Preparation of PLGA-854a Conjugate

Example 3: Preparation of PLGA-R848 Conjugate

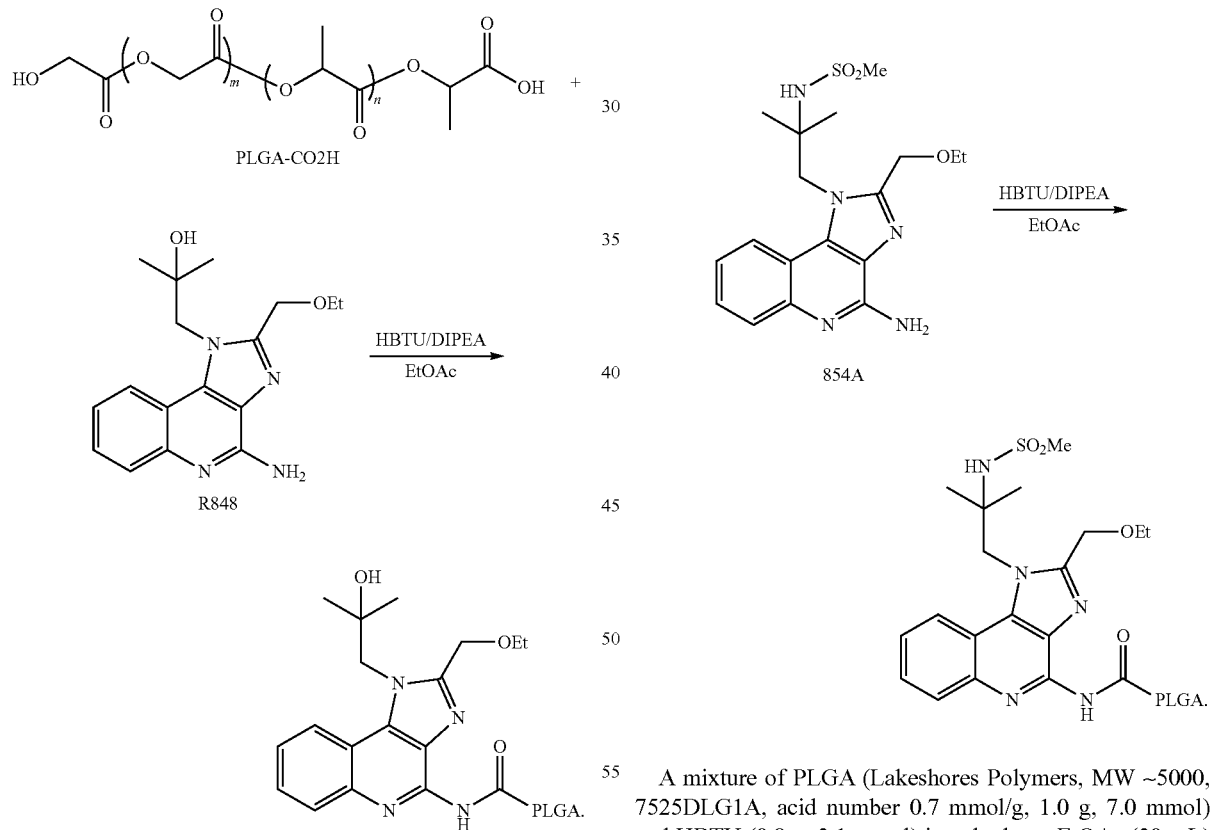

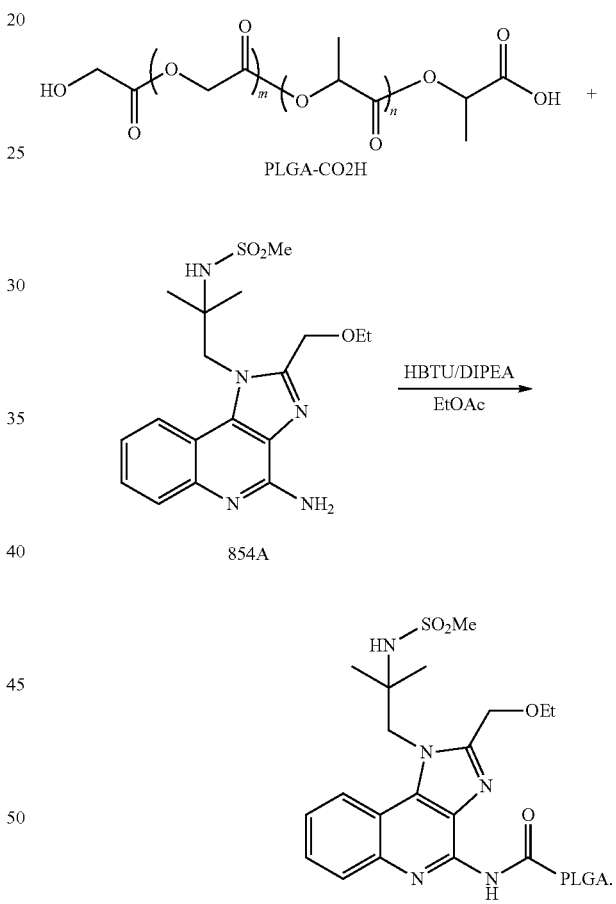

A mixture of PLGA (Lakeshores Polymers, MW ~5000, 7525DLG1A, acid number 0.7 mmol/g, 10 g, 7.0 mmol) and HBTU (5.3 g, 14 mmol) in anhydrous EtOAc (160 mL) was stirred at room temperature under argon for 50 minutes. Compound R848 (2.2 g, 7 mmol) was added, followed by diisopropylethylamine (DIPEA) (5 mL, 28 mmol). The mixture was stirred at room temperature for 6 h and then at A mixture of PLGA (Lakeshores Polymers, MW ~5000, 7525DLG1A, acid number 0.7 mmol/g, 1.0 g, 7.0 mmol) and HBTU (0.8 g, 2.1 mmol) in anhydrous EtOAc (20 mL) was stirred at room temperature under argon for 45 minutes. Compound 845A (0.29 g, 0.7 mmol) was added, followed by diisopropylethylamine (DIPEA) (0.73 mL, 4.2 mmol). The mixture was stirred at room temperature for 6 h and then at 50-55° C. overnight (about 15 h). After cooling, the mixture was diluted with EtOAc (100 mL) and washed with saturated NH4Cl solution (2×20 mL), water (20 mL) and brine solution (20 mL). The solution was dried over Na$_2$SO$_4$ (10 g) and concentrated to a gel-like residue. Isopropyl alcohol (IPA) (40 mL) was then added and the polymer conjugate precipitated out of solution. The polymer was then washed with IPA (4×25 mL) to remove residual reagents and dried under vacuum at 35-40° C. for 2 days as a white powder (1.21 g, MW by GPC is 4900, 854A loading is 14% by HPLC).

Example 5: Preparation of PLGA-BBHA Conjugate

Example 6: Preparation of Low MW PLA-R848 Conjugate

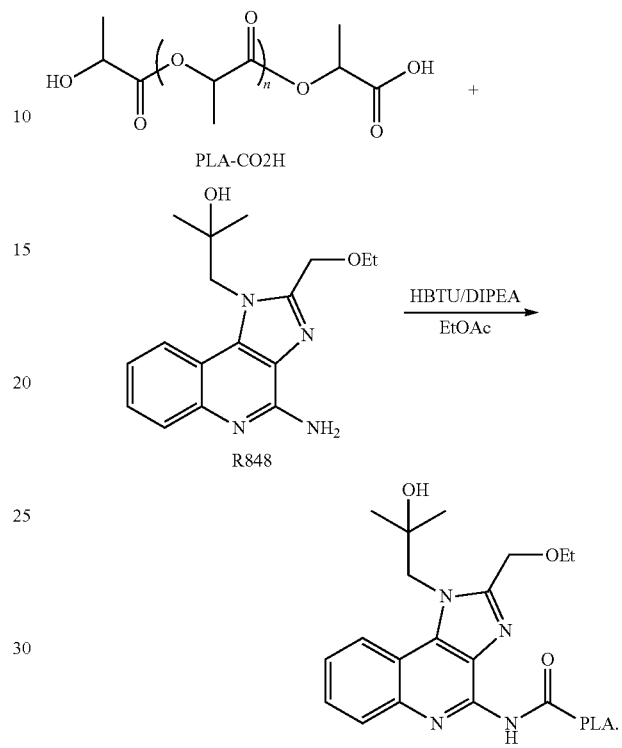

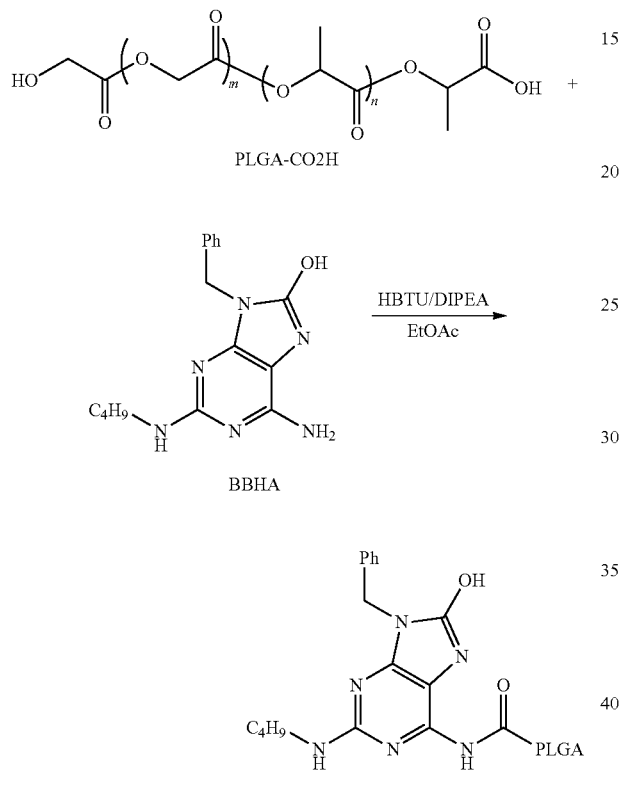

A solution of PLA-CO2H (average MW: 950, DPI: 1.32; 5.0 g, 5.26 mmol) and HBTU (4.0 g, 10.5 mmol) in EtOAc (120 mL) was stirred at room temperature under argon for 45 min. Compound R848 (1.65 g, 5.26 mmol) was added, followed by DIPEA (5.5 mL, 31.6 mmol). The mixture was stirred at room temperature for 6 h and then at 50-55° C. for 15 h. After cooling, the mixture was diluted with EtOAc (150 mL) and washed with 1% citric acid solution (2×40 mL), water (40 mL) and brine solution (40 mL). The solution was dried over $Na_2SO_4$ (10 g) and concentrated to a gel-like residue. Methyl t-butyl ether (MTBE) (150 mL) was then added and the polymer conjugate precipitated out of solution. The polymer was then washed with MTBE (50 mL) and dried under vacuum at room temperature for 2 days as a white foam (5.3 g, average MW by GPC is 1200, PDI: 1.29; R848 loading is 20% by HPLC).

A mixture of PLGA (Lakeshores Polymers, MW ~5000, 7525DLG1A, acid number 0.7 mmol/g, 1.0 g, 7.0 mmol) and HBTU (0.8 g, 2.1 mmol) in anhydrous EtOAc (30 mL) was stirred at room temperature under argon for 30 minutes. Compound BBHA (0.22 g, 0.7 mmol) in 2 mL of dry DMSO was added, followed by diisopropylethylamine (DIPEA) (0.73 mL, 4.2 mmol). The mixture was stirred at room temperature for 20 h. Additional amounts of HBTU (0.53 g, 1.4 mmol) and DIPEA (0.5 mL, 2.8 mmol) were added and the mixture was heated at 50-55° C. for 4 h. After cooling, the mixture was diluted with EtOAc (100 mL) and washed with saturated NH4Cl solution 20 mL), water (2×20 mL) and brine solution (20 mL). The solution was dried over $Na_2SO_4$ (10 g) and concentrated to a gel-like residue. Isopropyl alcohol (IPA) (35 mL) was then added and the brownish polymer conjugate precipitated out of solution. The polymer was then washed with IPA (2×20 mL) to remove residual reagents and dried under vacuum at 35-40° C. for 2 days as a brownish powder (1.1 g).

Example 7: Preparation of Low MW PLA-R848 Conjugate

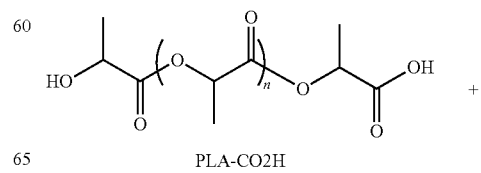

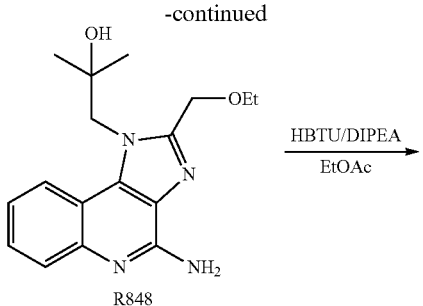

A solution of PLA-CO2H (average MW: 1800, DPI: 1.44; 9.5 g, 5.26 mmol) and HBTU (4.0 g, 10.5 mmol) in EtOAc (120 mL) was stirred at room temperature under argon for 45 min. Compound R848 (1.65 g, 5.26 mmol) was added, followed by DIPEA (5.5 mL, 31.6 mmol). The mixture was stirred at room temperature for 6 h and then at 50-55° C. for 15 h. After cooling, the mixture was diluted with EtOAc (150 mL) and washed with 1% citric acid solution (2×40 mL), water (40 mL) and brine solution (40 mL). The solution was dried over $Na_2SO_4$ (10 g) and concentrated to a gel-like residue. Methyl t-butyl ether (MTBE) (150 mL) was then added and the polymer conjugate precipitated out of solution. The polymer was then washed with MTBE (50 mL) and dried under vacuum at room temperature for 2 days as a white foam (9.5 g, average MW by GPC is 1900, PDI: 1.53; R848 loading is 17% by HPLC).

Example 8: Conjugation of R848 to PCADK Via Imide Ring Opening

The following examples describes the synthesis of a polyketal, PCADK, according to a method provided in Pulendran et al, WO 2008/127532, illustrated in step 1 below.

PCADK is synthesized in a 50 mL two-necked flask, connected to a short-path distilling head. First, 5.5 mg of re-crystallized p-toluenesulfonic acid (0.029 mmol, Aldrich, St. Louis, Mo.), is dissolved in 6.82 mL of ethyl acetate, and added to a 30 mL benzene solution (kept at 100° C.), which contains 1,4-cyclohexanedimethanol (12.98 g, 90.0 mmol, Aldrich). The ethyl acetate is allowed to boil off, and distilled 2,2-dimethoxypropane (10.94 mL, 90.0 mmol, Aldrich) is added to the benzene solution, initiating the polymerization reaction. Additional doses of 2,2-dimethoxypropane (5 mL) and benzene (25 mL) are subsequently added to the reaction every hour for 6 hours via a metering funnel to compensate for 2,2-dimethoxypropane and benzene that is distilled off. After 8 hours, the reaction is stopped by addition of 500 μL of triethylamine. The polymer is isolated by precipitation in cold hexane (stored at −20° C.) followed by vacuum filtration. The molecular weight of PCADK is determined by gel permeation chromatography (GPC) (Shimadzu, Kyoto, Japan) equipped with a UV detector. THF is used as the mobile phase at a flow rate of 1 ml/min. Polystyrene standards from Polymer Laboratories (Amherst, Mass.) are used to establish a molecular weight calibration curve. This compound is used to generate the PCADK particles in all subsequent experiments.

R848 may be conjugated to the terminal alcohol groups of the PCADK having molecular weight 6000 via imide ring opening, according to the step 2 shown below.

Step 1: Preparation of PCADK

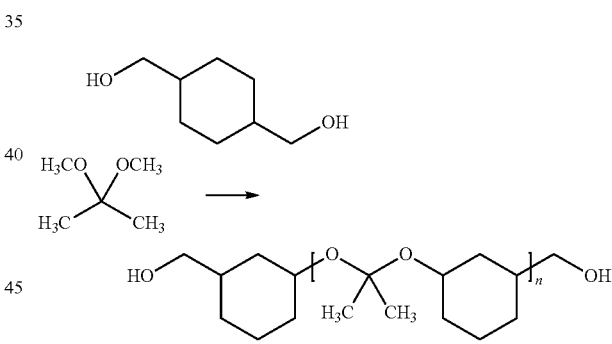

Step 2: Conjugation of PCADK to R848

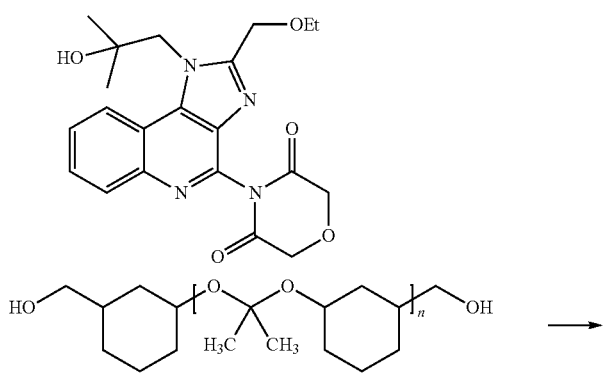

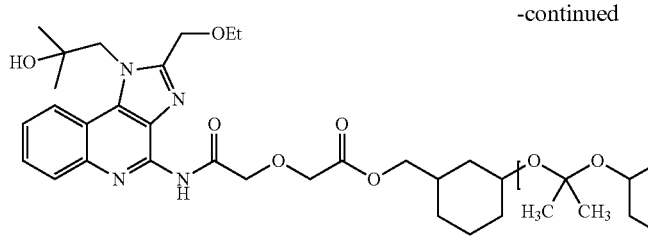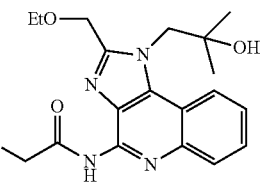

In step 2, the polymer from step 1 (12 g, $2.0 \times 10^{-3}$ moles) is dissolved in methylene chloride 100 mL, and the lactam of R848 (3.3 g, $8.0 \times 10^{-3}$ moles) is added. This slurry is stirred as 1,5,7-triazabicyclo-[4,4,0]dec-5-ene (TBD, 0.835 g, $6 \times 10^{-3}$ moles) is added in a single portion. After stirring at room temperature overnight, a clear solution forms. The solution is diluted with methylene chloride (100 mL) and the solution is washed with 5% citric acid. This solution is dried over sodium sulfate after which it is filtered and evaporated under vacuum. After drying under high vacuum there is obtained 11.3 grams (81%) of polymer. A portion is hydrolyzed in acid and the R848 content is determined to be 9% by weight.

Example 9: Conjugation of R848 to Poly-Caprolactonediol Via Imide Ring Opening Imide ring opening is used to attach R854 to the terminal alcohol groups of poly-caprolactonediol of molecular weight 2000. The polycaprolactone diol is purchased from Aldrich Chemical Company, Cat. #189421, and has the following structure:

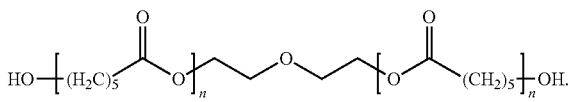

The polycaprolactone diol-R854 conjugate has the following structure:

The polymer (5 g, $2.5 \times 10^{-3}$ moles) is dissolved in methylene chloride 25 mL and the lactam of R854 (2.4 g, $5.0 \times 10^{-3}$ moles) is added. This slurry is stirred as 1,5,7-triazabicyclo-[4,4,0]dec-5-ene (TBD, 0.557 g, $4 \times 10^{-3}$ moles) is added in a single portion. After stirring at room temperature for 15 minutes, a clear pale yellow solution forms. The solution is diluted with methylene chloride (100 mL) and the solution is washed with 5% citric acid. This solution is dried over sodium sulfate after which it is filtered and evaporated under vacuum. After drying under high vacuum there is obtained 5.2 grams (70%) of polymer. A portion is hydrolyzed in acid and the R848 content is determined to be 18.5% by weight.

Example 10: Conjugation of R848 to Poly-(Hexamethylene Carbonate)Diol Via Imide Ring Opening Imide ring opening is used to attach R848 to the terminal alcohol groups of poly-(hexamethylene carbonate)diol of molecular weight 2000. The poly(hexamethylene carbonate) diol is purchased from Aldrich Chemical Company, Cat #461164, and has the following structure:

HO—[CH$_2$(CH$_2$)$_4$CH$_2$OCO$_2$]$_n$CH$_2$(CH$_2$)$_4$CH$_2$—OH.

The poly(hexamethylene carbonate) diol-R848 conjugate has the following structure:

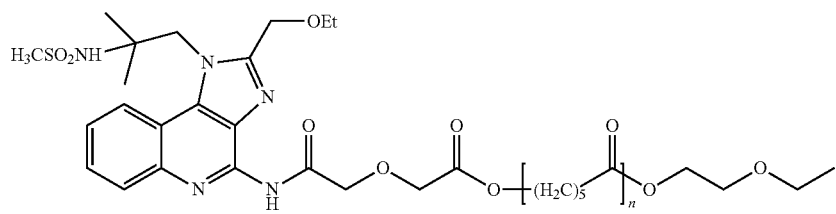

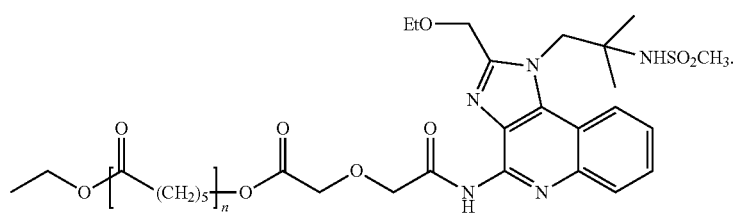

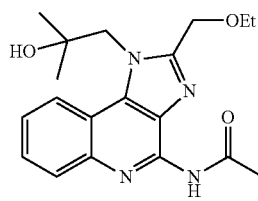 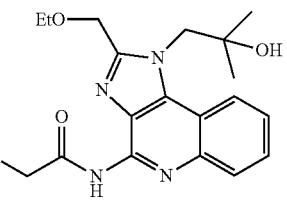

The polymer (5 g, 2.5×10⁻³ moles) is dissolved in methylene chloride 25 mL and the lactam of R848 (2.06 g, 5.0×10⁻³ moles) is added. This slurry is stirred as 1,5,7-triazabicyclo-[4,4,0]dec-5-ene (TBD, 0.557 g, 4×10⁻³ moles) is added in a single portion. After stirring at room temperature overnight a clear pale yellow solution forms. The solution is diluted with methylene chloride (100 mL) and the solution is washed with 5% citric acid. This solution is dried over sodium sulfate after which it is filtered and evaporated under vacuum. After drying under high vacuum there is obtained 5.9 grams (84%) of polymer. NMR is used to determine the R848 content which is determined to be 21%.

Example 11: Polylactic Acid Conjugates of an Imidazoquinoline Using a Tin Ethylhexanoate Catalyst

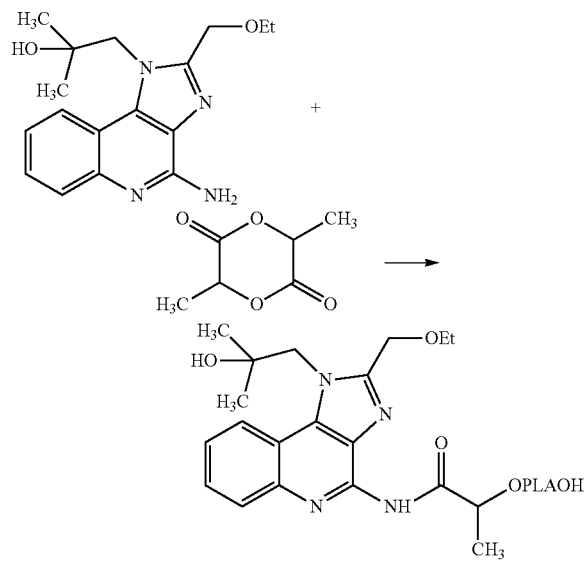

To a two necked round bottom flask equipped with a stir bar and condenser was added the imidazoquinoline resiquimod (R-848, 100 mg, 3.18×10⁻⁴ moles), D/L lactide (5.6 g, 3.89×10⁻² moles) and anhydrous sodium sulfate (4.0 g). The flask and contents were dried under vacuum at 50° C. for 8 hours. The flask was then flushed with argon and toluene (100 mL) was added. The reaction was stirred in an oil bath set at 120° C. until all of the lactide had dissolved and then tin ethylhexanoate (75 mg, 60 µL) was added via pipette. Heating was continued under argon for 16 hours. After cooling, water (20 mL) was added and stirring was continued for 30 minutes. The reaction was diluted with additional toluene (200 mL) and was then washed with water (200 mL). The toluene solution was then washed in turn with 10% sodium chloride solution containing 5% conc. Hydrochloric acid (200 mL) followed by saturated sodium bicarbonate (200 mL). TLC (silica, 10% methanol in methylene chloride) showed that the solution contained no free R-848. The solution was dried over magnesium sulfate, filtered and evaporated under vacuum to give 3.59 grams of polylactic acid-R-848 conjugate. A portion of the polymer was hydrolyzed in base and examined by HPLC for R-848 content. By comparison to a standard curve of R-848 concentration vs. HPLC response, it was determined that the polymer contained 4.51 mg of R-848 per gram of polymer. The molecular weight of the polymer was determined by GPC to be about 19,000.

Example 12: Low Molecular Weight Polylactic Acid Conjugates of an Imidazoquinoline

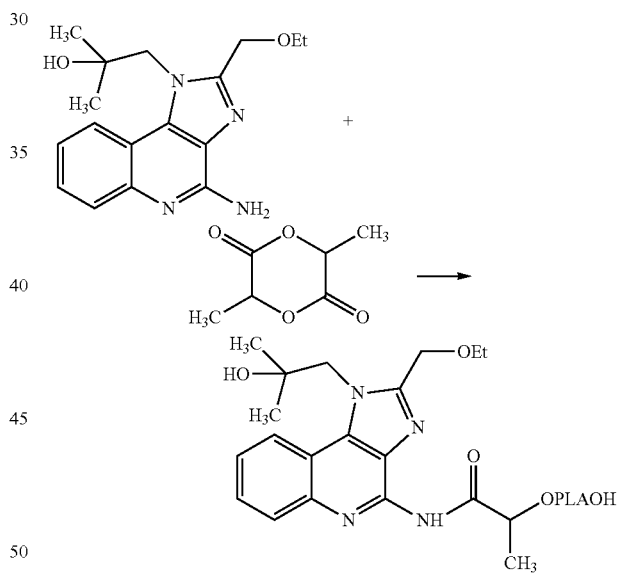

To a round bottom flask equipped with a stir bar and condenser was added the imidazoquinoline, resiquimod (R-848, 218 mg, 6.93×10⁻⁴ moles), D/L lactide (1.0 g, 6.93×10⁻³ moles) and anhydrous sodium sulfate (800 mg). The flask and contents were dried under vacuum at 55° C. for 8 hours. After cooling, the flask was then flushed with argon and toluene (50 mL) was added. The reaction was stirred in an oil bath set at 120° C. until all of the lactide had dissolved and then tin ethylhexanoate (19 mg, 15 µL) was added via pipette. Heating was continued under argon for 16 hours. After cooling, the reaction was diluted with ether (200 mL) and the solution was washed with water (200 mL). The solution was dried over magnesium sulfate, filtered and evaporated under vacuum to give 880 mg. of crude polylactic acid-R-848 conjugate. The crude polymer was chromatographed on silica using 10% methanol in methylene chloride as eluent. The fractions containing the conjugate were pooled and evaporated to give the purified conjugate. This was dried under high vacuum to provide the conjugate as a solid foam in a yield of 702 mg (57.6%). By integrating the NMR signals for the aromatic protons of the quinoline and comparing this to the integrated intensity of the lactic acid CH proton it was determined that the molecular weight of the conjugate was approximately 2 KD. GPC showed that the conjugate contained less than 5% of free R848.

Example 13: Low Molecular Weight Polylactic Acid Co-Glycolic Acid Conjugates of an Imidazoquinoline

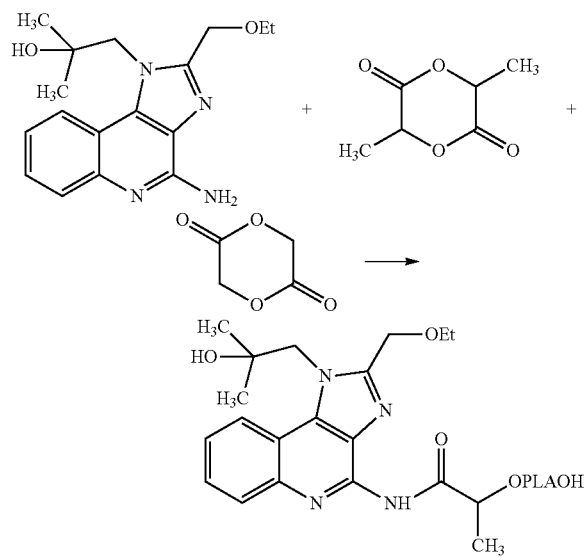

To a round bottom flask equipped with a stir bar and condenser was added the imidazoquinoline, resiquimod (R-848, 436 mg, $1.39 \times 10^{-3}$ moles), glycolide (402 mg, $3.46 \times 10^{-3}$ moles), D/L lactide (2.0 g, $1.39 \times 10^{-2}$ moles) and anhydrous sodium sulfate (1.6 g). The flask and contents were dried under vacuum at 55° C. for 8 hours. After cooling, the flask was then flushed with argon and toluene (60 mL) was added. The reaction was stirred in an oil bath set at 120° C. until all of the R848, glycolide and lactide had dissolved and then tin ethylhexanoate (50 mg, 39 µL) was added via pipette. Heating was continued under argon for 16 hours. After cooling, the reaction was diluted with ethyl acetate (200 mL) and the solution was washed with water (200 mL). The solution was dried over magnesium sulfate, filtered and evaporated under vacuum to give crude PLGA-R-848 conjugate. The crude polymer was chromatographed on silica using 10% methanol in methylene chloride as eluent. The fractions containing the conjugate were pooled and evaporated to give the purified conjugate. This was dried under high vacuum to provide the conjugate as a solid foam in a yield of 1.55 g (54.6%). By integrating the NMR signals for the aromatic protons of the quinoline and comparing this to the integrated intensity of the lactic acid CH proton it was determined that the molecular weight of the conjugate was approximately 2 KD. GPC showed that the conjugate contained no detectable free R848.

Example 14: Polylactic Acid Conjugates of an Imidazoquinoline Using a Lithium Diisopropylamide Catalysis The imidazoquinoline (R-848), D/L lactide, and associated glassware were all dried under vacuum at 50° C. for 8 hours prior to use. To a round bottom flask equipped with a stir bar and condenser was added the R-848 (33 mg, $1.05 \times 10^{-4}$ moles), and dry toluene (5 mL). This was heated to reflux to dissolve all of the R-848. The solution was stirred under nitrogen and cooled to room temperature to provide a suspension of finely divided R-848. To this suspension was added a solution of lithium diisopropyl amide (2.0 M in THF, 504, $1.0 \times 10^{-4}$ moles) after which stirring was continued at room temperature for 5 minutes. The pale yellow solution that had formed was added via syringe to a hot (120° C.) solution of D/L lactide (1.87 g, $1.3 \times 10^{-2}$ moles) under nitrogen. The heat was removed and the pale yellow solution was stirred at room temperature for one hour. The solution was diluted with methylene chloride (200 mL) and this was then washed with 1% hydrochloric acid (2×50 mL) followed by saturated sodium bicarbonate solution (50 mL). The solution was dried over magnesium sulfate, filtered and evaporated under vacuum to give the polylactic acid-R-848 conjugate. TLC (silica, 10% methanol in methylene chloride) showed that the solution contained no free R-848. The polymer was dissolved in methylene chloride (10 mL) and the solution was dripped into stirred hexane (200 mL). The precipitated polymer was isolated by decantation and was dried under vacuum to give 1.47 grams of the polylactic acid—R-848 conjugate as a white solid. A portion of the polymer was hydrolyzed in base and examined by HPLC for R-848 content. By comparison to a standard curve of R-848 concentration vs. HPLC response, it was determined that the polymer contained 10.96 mg of R-848 per gram of polymer.

Example 15: Polylactic Acid Activation

PLA (D/L-polylactide) (Resomer R202H from Boehringer-Ingelheim, KOH equivalent acid number of 0.21 mmol/g, intrinsic viscosity (iv): 0.21 dl/g) (10 g, 2.1 mmol, 1.0 eq) was dissolved in dichloromethane (DCM) (35 mL). EDC (2.0 g, 10.5 mmol, 5 eq) and NHS (1.2 g, 10.5 mmol, 5 eq) were added. The solids were dissolved with the aid of sonication. The resulting solution was stirred at room temperature for 6 days. The solution was concentrated to remove most of DCM and the residue was added to a solution of 250 mL of diethyl ether and 5 mL of MeOH to precipitate out the activated PLA-NHS ester. The solvents were removed and the polymer was washed twice with ether (2×200 mL) and dried under vacuum to give PLA-NHS activated ester as a white foamy solid (~8 g recovered, $^1$H NMR confirmed the presence of NHS ester). The PLA-NHS ester is stored under argon in a below −10° C. freezer before use.

Alternatively, the reaction can be performed in DMF, THF, dioxane, or CHCl$_3$ instead of DCM. DCC can be used instead of EDC (resulting DCC-urea is filtered off before precipitation of the PLA-NHS ester from ether). The amount of EDC or DCC and NHS can be in the range of 2-10 eq of the PLA.

Example 16: PLA Activation

PLA (D/L-polylactide) with MW of 5000 (10.5 g, 2.1 mmol, 1.0 eq) is dissolved in dichloromethane (DCM) (35 mL). EDC (2.0 g, 10.5 mmol, 5 eq) and NHS (1.2 g, 10.5 mmol, 5 eq) are added. The resulting solution is stirred at room temperature for 3 days. The solution is concentrated to remove most of DCM and the residue is added to a solution of 250 mL of diethyl ether and 5 mL of MeOH to precipitate out the activated PLA-NHS ester. The solvents are removed and the polymer is washed twice with ether (2×200 mL) and dried under vacuum to give PLA-NHS activated ester as a white foamy solid (~8 g recovered, H NMR can be used to confirm the presence of NHS ester). The PLA-NHS ester is stored under argon in a below −10° C. freezer before use.

Alternatively, the reaction can be performed in DMF, THF, dioxane, or CHCl3 instead of DCM. DCC can be used instead of EDC (resulting DCC-urea is filtered off before precipitation of the PLA-NHS ester from ether). The amount of EDC or DCC and NHS can be in the range of 2-10 eq of the PLA.

Example 17: Low MW PLGA Activation

In the same manner as provided above for polymer activation, low MW PLGA with 50% to 75% glycolide is converted to the corresponding PLGA-NHS activated ester and is stored under argon in a below −10° C. freezer before use.

Example 18: Polylactic Acid Activation

PLA (R202H, acid number of 0.21 mmol/g) (2.0 g, 0.42 mmol, 1.0 eq) was dissolved in 10 mL of dry acetonitrile. N,N'-disuccinimidyl carbonate (DSC) (215 mg, 1.26 mmol, 3.0 eq) and catalytic amount of 4-(N,N-dimethylamino) pyridine (DMAP) were added. The resulting mixture was stirred under argon for 1 day. The resulting solution was concentrated to almost dryness. The residue was then added to 40 mL of ether to precipitate out the polymer which was washed twice with ether (2×30 mL) and dried under vacuum to give PLA-NHS activated ester (1H NMR showed the amount of NHS ester at about 80%).

Example 19: Polylactic Acid Activation

PLA (R202H) (5.0 g, 1.05 mmol) was dissolved in 25 mL of anhydrous DCM and 2.5 mL of anhydrous DMF. DCC (650 mg, 3.15 mmol, 5.0 eq) and pentafluorophenol (PFP) (580 mg, 3.15 mmol, 5.0 eq) were added. The resulting solution was stirred at room temperature for 6 days and then concentrated to remove DCM. The resulting residue was added to 250 mL of ether to precipitate out the activated PLA polymer which was washed with ether (2×100 mL) and dried under vacuum to give PLA-PFP activated ester as a white foamy solid (4.0 g).

Example 20: Polylactic Acid or PLGA Conjugates of an Imidazoquinoline

PLA-NHS (1.0 g), R848 (132 mg, 0.42 mmol), and diisopropylethylamine (DIPEA) (0.073 mL, 0.42 mmol) were dissolved in 2 mL of dry DMF under argon. The resulting solution was heated at 50-60° C. for 2 days. The solution was cooled to room temperature and added to 40 mL of de-ionized (DI) water to precipitate out the polymer product. The polymer was then washed with DI water (40 mL) and ether (2×40 mL) and dried at 30° C. under vacuum to give R848-PLA conjugate as a white foamy solid (0.8 g, H NMR showed the conjugation of R848 to PLA via the amide bond). The degree of conjugation (loading) of R848 on the polymer was confirmed by HPLC analysis as follows: a weighed amount of polymer was dissolved in THF/MeOH and treated with 15% NaOH. The resulting hydrolyzed polymer products were analyzed for the amount of R848 by HPLC in comparison with a standard curve.

Example 21: Polylactic Acid or PLGA Conjugates of an Imidazoquinoline

PLA-NHS (1.0 g, 0.21 mmol, 1.0 eq), R848 (132 mg, 0.42 mmol, 2.0 eq), DIPEA (0.15 mL, 0.84 mmol, 4.0 eq) and DMAP (25 mg, 0.21 mmol, 1.0 eq) were dissolved in 2 mL of dry DMF under argon. The resulting solution was heated at 50-60° C. for 2 days. The solution was cooled to room temperature and added to 40 mL of de-ionized (DI) water to precipitate out the polymer product. The polymer was then washed with DI water (40 mL) and ether (2×40 mL) and dried at 30° C. under vacuum to give PLA-R848 conjugate as a white foamy solid (0.7 g, 20 mg of the polymer was hydrolyzed in solution of 0.2 mL of THF, 0.1 mL of MeOH and 0.1 mL of 15% NaOH. The amount of R848 on the polymer was determined to be about 35 mg/g by reverse phase HPLC analysis (C18 column, mobile phase A: 0.1% TFA in water, mobile phase B: 0.1% TFA in CH3CN, gradient).

Example 22: Polylactic Acid Conjugates of an Imidazoquinoline

PLA (R202H) (2.0 g, 0.42 mmol, 1.0 eq), DCC (260 mg, 1.26 mmol, 3.0 eq), NHS (145 mg, 1.26 mmol, 3.0 eq), R848 (200 mg, 0.63 mmol, 1.5 eq), DMAP (77 mg, 0.63 mmol, 1.5 eq) and DIPEA (0.223 mL, 1.26 mmol, 3.0 eq) were dissolved in 4 mL of dry DMF. The mixture was heated at 50-55° C. for 3 days. The mixture was cooled to room temperature and diluted with DCM. The DCC-urea was filtered off and the filtrate was concentrated to remove DCM. The resulting residue in DMF was added to water (40 mL) to precipitate out the polymer product which was washed with water (40 mL), ether/DCM (40 mL/4 mL) and ether (40 mL). After drying under vacuum at 30° C., the desired PLA-R848 conjugate was obtained as a white foamy solid (1.5 g).

Example 23: Polylactic Acid Conjugates of an Imidazoquinoline

PLA (R202H) (2.0 g, 0.42 mmol, 1.0 eq), EDC (242 mg, 1.26 mmol, 3.0 eq), HOAt (171 mg, 1.26 mmol, 3.0 eq), R848 (200 mg, 0.63 mmol, 1.5 eq), and DIPEA (0.223 mL, 1.26 mmol, 3.0 eq) were dissolved in 4 mL of dry DMF. The mixture was heated at 50-55° C. for 2 days. The solution was cooled to room temperature and added to water (40 mL) to precipitate out the polymer product which was washed with water (40 mL), ether/MeOH (40 mL/2 mL) and ether (40 mL). The orange colored polymer was dissolved in 4 mL of DCM and the resulting solution was added to 40 mL of ether to precipitate out the polymer without much of the orange color. The light colored polymer was washed with ether (40 mL). After drying under vacuum at 30° C., the desired PLA-R848 conjugate was obtained as a light brown foamy solid (1.5 g).

Example 24: Polylactic Acid or PLGA Conjugates of an Imidazoquinoline

PLA (R202H) (1.0 g, 0.21 mmol, 1.0 eq), EDC (161 mg, 0.84 mmol, 4.0 eq), HOBt.H2O (65 mg, 0.42 mmol, 2.0 eq), R848 (132 mg, 0.42 mmol, 2.0 eq), and DIPEA (0.150 mL, 0.84 mmol, 4.0 eq) were dissolved in 2 mL of dry DMF. The mixture was heated at 50-55° C. for 2 days. The solution was cooled to room temperature and added to water (40 mL) to precipitate out the polymer product. The orange colored polymer was dissolved in 2 mL of DCM and the resulting solution was added to 40 mL of ether to precipitate out the polymer which was washed with water/acetone (40 mL/2 mL) and ether (40 mL). After drying under vacuum at 30° C., the desired PLA-R848 conjugate was obtained as an off-white foamy solid (1.0 g, loading of R848 on polymer was about 45 mg/g based on HPLC analysis and confirmed by $^1$H NMR). In the same manner, PLGA (75% Lactide)-R848 and PLGA (50% lactide)-R848 were prepared.

Example 25: Conjugation of R848 to Polyglycine, a Polyamide

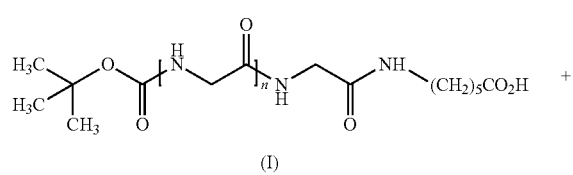

(I)

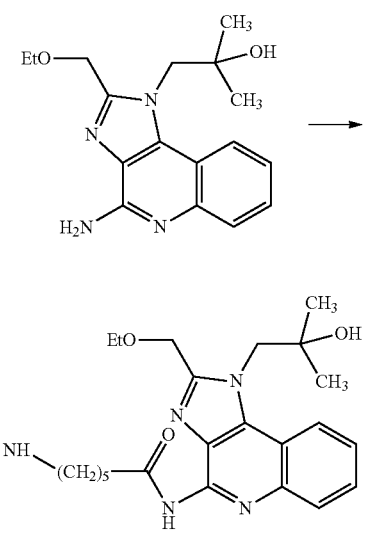

The t-butyloxycarbonyl (tBOC) protected polyglycine carboxylic acid (I) is prepared by ring opening polymerization of glycine N-carboxyanhydride (Aldrich cat #369772) using 6-aminohexanoic acid benzyl ester (Aldrich cat #S33465) by the method of Aliferis et al. (*Biomacromolecules*, 5, 1653, (2004)). Protection of the end amino group as the t-BOC carbamate followed by hydrogenation over palladium on carbon to remove the benzyl ester completes the synthesis of BOC protected polyglycine carboxylic acid (I).

A mixture of BOC-protected polyglycine carboxylic acid (5 gm, MW=2000, 2.5×10$^{-3}$ moles) and HBTU (3.79 gm, 1.0×10$^{-2}$ moles) in anhydrous DMF (100 mL) is stirred at room temperature under argon for 50 minutes. Then R848 (1.6 gm, 5.0×10$^{-3}$ moles) is added, followed by diisopropylethylamine (4 mL, 2.2×10$^{-2}$ moles). The mixture is stirred at RT for 6 h and then at 50-55° C. overnight (16 h). After cooling, the DMF is evaporated under vacuum and the residue is triturated in EtOAc (100 mL). The polymer is isolated by filtration and the polymer is then washed with 2-propanol (4×25 mL) to remove residual reagents and dried under vacuum at 35-40° C. for 3 days. The polymer is isolated as an off white solid in a yield of 5.1 g (88%). The R848 loading that can be determined by NMR is 10.1%.

The t-BOC protecting group is removed using trifluoroacetic acid and the resulting polymer is grafted to PLA with carboxyl end groups by conventional methods.

Example 26: Preparation of a PLGA Conjugate of the Polyglycine/R848 Polymer

Step 1: A t-BOC protected polyglycine/R848 conjugate (5 g) is dissolved in trifluoroacetic acid (25 mL) and this solution is warmed at 50° C. for one hour. After cooling, the trifluoroacetic acid is removed under vacuum and the residue is triturated in ethyl acetate (25 mL). The polymer is isolated by filtration and is washed well with 2-propanol. After drying under vacuum there is obtained 4.5 grams of polymer as an off white solid.

Step 2: A mixture of PLGA (Lakeshores Polymers, MW ~5000, 7525DLG1A, acid number 0.7 mmol/g, 10 g, 7.0 mmol) and HBTU (5.3 g, 14 mmol) in anhydrous DMF (100 mL) is stirred at RT under argon for 50 minutes. The polymer from above (1.4 g, 7 mmol) dissolved in dry DMF (20 mL) is added, followed by diisopropylethylamine (DIPEA) (5 mL, 28 mmol). The mixture is stirred at RT for 6 h and then at 50-55° C. overnight (16 h). After cooling, the DMF is evaporated under vacuum, and the residue is dissolved in methylene chloride (50 mL). The polymer is precipitated by the addition of 2-propanol (200 mL). The polymer is isolated by decantation and is washed with 2-propanol (4×50 mL) to remove residual reagents and then dried under vacuum at 35-40 C overnight. There is obtained 9.8 g (86%) of the block copolymer.

Example 27: Preparation of PLGA-2-Butoxy-8-Hydroxy-9-Benzyl Adenine Conjugate

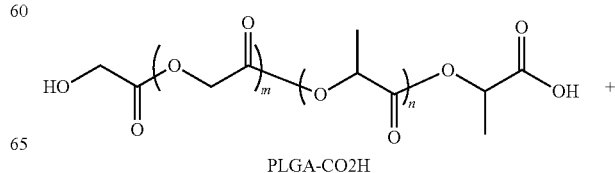

PLGA-CO2H

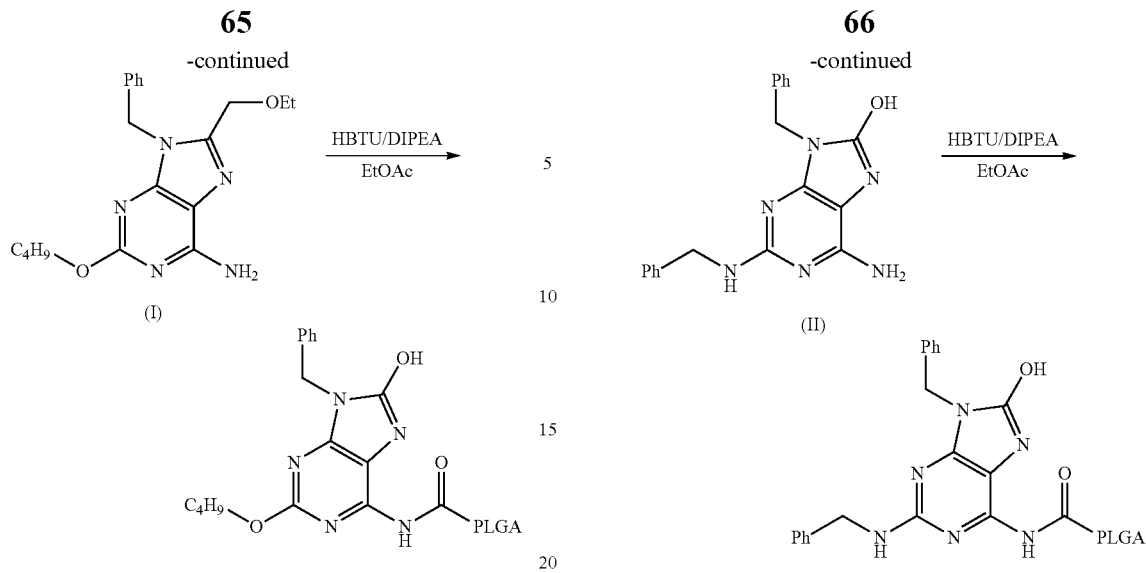

A mixture of PLGA (Lakeshores Polymers, MW ~5000, 7525DLG1A, acid number 0.7 mmol/g, 1.0 g, 7.0 mmol) and HBTU (0.8 g, 2.1 mmol) in anhydrous EtOAc (30 mL) is stirred at RT under argon for 30 minutes. Compound (I) (0.22 g, 0.7 mmol) in 2 mL of dry DMSO is added, followed by diisopropylethylamine (DIPEA) (0.73 mL, 4.2 mmol). The mixture is stirred at room temperature for 20 h. Additional amounts of HBTU (0.53 g, 1.4 mmol) and DIPEA (0.5 mL, 2.8 mmol) are added and the mixture is heated at 50-55° C. for 4 h. After cooling, the mixture is diluted with EtOAc (100 mL) and washed with saturated $NH_4Cl$ solution 20 mL), water (2×20 mL) and brine solution (20 mL). The solution is dried over $Na_2SO_4$ (10 g) and concentrated to a gel-like residue. Isopropyl alcohol (IPA) (35 mL) is then added and the brownish polymer conjugate precipitates out of solution. The polymer is then washed with IPA (2×20 mL) to remove residual reagents and dried under vacuum at 35-40° C. for 2 days as a brownish powder (1.0 g).

A mixture of PLGA (Lakeshores Polymers, MW ~5000, 7525DLG1A, acid number 0.7 mmol/g, 1.0 g, 7.0 mmol) and HBTU (0.8 g, 2.1 mmol) in anhydrous EtOAc (30 mL) is stirred at RT under argon for 30 minutes. Compound (II) (0.24 g, 0.7 mmol) in 2 mL of dry DMSO is added, followed by diisopropylethylamine (DIPEA) (0.73 mL, 4.2 mmol). The mixture is stirred at RT for 20 h. Additional amounts of HBTU (0.53 g, 1.4 mmol) and DIPEA (0.5 mL, 2.8 mmol) are added and the mixture is heated at 50-55° C. for 4 h. After cooling, the mixture is diluted with EtOAc (100 mL) and washed with saturated $NH_4Cl$ solution 20 mL), water (2×20 mL) and brine solution (20 mL). The solution is dried over $Na_2SO_4$ (10 g) and concentrated to a gel-like residue. Isopropyl alcohol (IPA) (35 mL) is then added and the brownish polymer conjugate precipitated out of solution. The polymer is then washed with IPA (2×20 mL) to remove residual reagents and dried under vacuum at 35-40° C. for 2 days as a brownish powder (1.2 g).

Example 28: Preparation of PLGA-2,9-Dibenzyl-8-Hydroxyadenine Conjugate

Example 29: Imide Ring Opening Used to Attach 2-Pentyl-8-Hydroxy-9-Benzyladenine to the Terminal Alcohol Groups of Poly-Hexamethylene Carbonate) Diol of Molecular Weight 2000

The poly(hexamethylene carbonate) diol is purchased from Aldrich Chemical Company, Cat #461164.

Poly(hexamethylene carbonate) diol:

HO—[$CH_2(CH_2)_4CH_2OCO_2$]$n$$CH_2(CH_2)_4CH_2$—OH

Poly(hexamethylene carbonate) diol-8-oxoadenine conjugate:

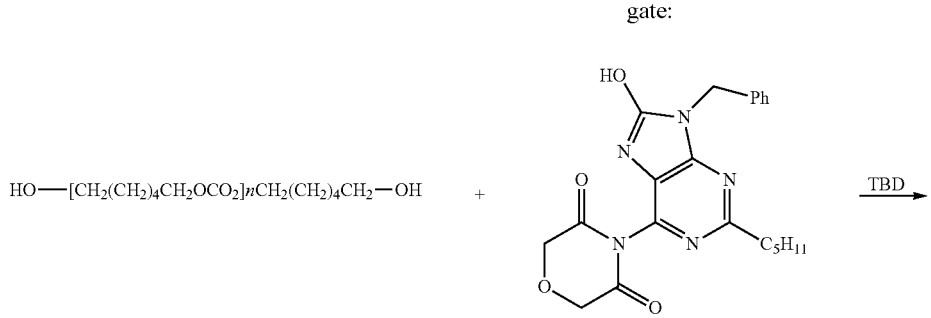

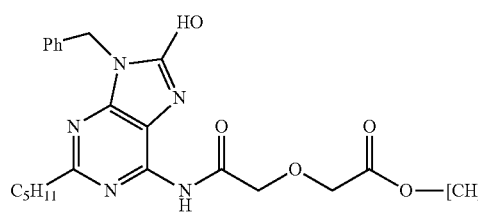
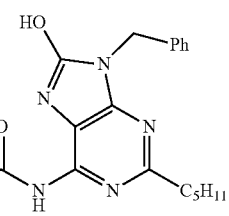

The polymer (5 g, 2.5×10⁻³ moles) is dissolved in methylene chloride 25 mL and the lactam of 2-pentyl-8-hydroxy-9-benzyladenine (2.05 g, 5.0×10⁻³ moles) is added. This slurry is stirred as 1,5,7-triazabicyclo-[4,4,0]dec-5-ene (TBD, 0.557 g, 4×10⁻³ moles) is added in a single portion. After stirring at room temperature overnight a clear pale yellow solution forms. The solution is diluted with methylene chloride (100 mL), and the solution is washed with 5% citric acid. This solution is dried over sodium sulfate after which it is filtered and evaporated under vacuum. After drying under high vacuum there is obtained 5.5 grams (78%) of polymer. NMR is used to determine the benzyladenine content which is 18%.

Example 30: Nicotine-Peg-Pla Conjugates

A 3-nicotine-PEG-PLA polymer was synthesized as follows:

First, monoamino poly(ethylene glycol) from JenKem® with a molecular weight of 3.5 KD (0.20 g, 5.7×10⁻⁵ moles) and an excess of 4-carboxycotinine (0.126 g, 5.7×10⁻⁴ moles) were dissolved in dimethylformamide (5.0 mL). The solution was stirred and dicyclohexylcarbodiimide (0.124 g, 6.0×10⁻⁴ moles) was added. This solution was stirred overnight at room temperature. Water (0.10 mL) was added and stirring was continued for an additional 15 minutes. The precipitate of dicyclohexyl urea was removed by filtration and the filtrates were evaporated under vacuum. The residue was dissolved in methylene chloride (4.0 mL) and this solution was added to diethyl ether (100 mL). The solution was cooled in the refrigerator for 2 hours and the precipitated polymer was isolated by filtration. After washing with diethyl ether, the solid white polymer was dried under high vacuum. The yield was 0.188 g. This polymer was used without further purification for the next step.

The nicotine/PEG polymer (0.20 g, 5.7×10⁻⁵ moles) was dissolved in dry tetrahydrofuran (10 mL) under nitrogen and the solution was stirred as a solution of lithium aluminum hydride in tetrahydrofuran (1.43 mL of 2.0 M, 2.85×10⁻³ moles) was added. The addition of the lithium aluminum hydride caused the polymer to precipitate as a gelatinous mass. The reaction was heated to 80° C. under a slow stream of nitrogen and the tetrahydrofuran was allowed to evaporate. The residue was then heated at 80° C. for 2 hours. After cooling, water (0.5 mL) was cautiously added. Once the hydrogen evolution had stopped, 10% methanol in methylene chloride (50 mL) was added and the reaction mixture was stirred until the polymer had dissolved. This mixture was filtered through Celite® brand diatomaceous earth (available from EMD Inc. as Celite® 545, part #CX0574-3) and the filtrates were evaporated to dryness under vacuum. The residue was dissolved in methylene chloride (4.0 mL) and this solution was slowly added to diethyl ether (100 mL). The polymer separated as a white flocculent solid and was isolated by centrifugation. After washing with diethyl ether, the solid was dried under vacuum. The yield was 0.129 g.

Next, a 100 mL round bottom flask, equipped with a stir bar and reflux condenser was charged with the PEG/nicotine polymer (0.081 g, 2.2×10⁻⁵ moles), D/L lactide (0.410 g, 2.85×10⁻³ moles) and anhydrous sodium sulfate (0.380 g). This was dried under vacuum at 55° C. for 8 hours. The flask was cooled and flushed with argon and then dry toluene (10 mL) was added. The flask was placed in an oil bath set at 120° C., and once the lactide had dissolved, tin ethylhexanoate (5.5 mg, 1.36×10⁻⁵ moles) was added. The reaction was allowed to proceed at 120° C. for 16 hours. After cooling to room temperature, water (15 mL) was added and stirring was continued for 30 minutes. Methylene chloride (200 mL) was added, and after agitation in a separatory funnel, the phases were allowed to settle. The methylene chloride layer was isolated and dried over anhydrous magnesium sulfate. After filtration to remove the drying agent, the filtrates were evaporated under vacuum to give the polymer as a colorless foam. The polymer was dissolved in tetrahydrofuran (10 mL) and this solution was slowly added to water (150 mL) with stirring. The precipitated polymer was isolated by centrifugation and the solid was dissolved in methylene chloride (10 mL). The methylene chloride was removed under vacuum and the residue was dried under vacuum. 3-nicotine-PEG-PLA polymer yield was 0.38 g Example 31: Synthetic Nanocarrier Formulation For encapsulated adjuvant formulations, Resiquimod (aka R848) was synthesized according to the synthesis provided in Example 99 of U.S. Pat. No. 5,389,640 to Gerster et al.

R848 was conjugated to PLA by a method provided above, and the PLA structure was confirmed by NMR.

PLA-PEG-nicotine conjugate was prepared according to Example 30.

PLA was purchased (Boehringer Ingelheim Chemicals, Inc., 2820 North Normandy Drive, Petersburg, Va. 23805). The polyvinyl alcohol (Mw=11 KD-31 KD, 85-89% hydrolyzed) was purchased from VWR scientific. Ovalbumin peptide 323-339 was obtained from Bachem Americas Inc. (3132 Kashiwa Street, Torrance Calif. 90505. Part #4064565).

The above materials were used to prepare the following solutions:

1. Resiquimod (R848) @ 10 mg/mL and PLA @ 100 mg/mL in methylene chloride or PLA-R848 conjugate @ 100 mg/mL in methylene chloride
2. PLA-PEG-nicotine in methylene chloride @ 100 mg/mL
3. PLA in methylene chloride @ 100 mg/mL
4. Ovalbumin peptide 323-339 in water @ 10 or 69 mg/mL
5. Polyvinyl alcohol in water @ 50 mg/mL.

Solution #1 (0.25 to 0.75 mL), solution #2 (0.25 mL), solution #3 (0.25 to 0.5 mL) and solution #4 (0.1 mL) were combined in a small vial and the mixture was sonicated at 50% amplitude for 40 seconds using a Branson Digital Sonifier 250. To this emulsion was added solution #5 (2.0 mL) and sonication at 35% amplitude for 40 seconds using the Branson Digital Sonifier 250 forms the second emulsion. This was added to a beaker containing phosphate buffer solution (30 mL) and this mixture was stirred at room temperature for 2 hours to form the nanoparticles.

To wash the particles a portion of the nanoparticle dispersion (7.4 mL) was transferred to a centrifuge tube and spun at 5,300 g for one hour, supernatant was removed, and the pellet was re-suspended in 7.4 mL of phosphate buffered saline. The centrifuge procedure was repeated and the pellet was re-suspended in 2.2 mL of phosphate buffered saline for a final nanoparticle dispersion of about 10 mg/mL.

Example 32: Double Emulsion with Multiple Primary Emulsions

Materials

Ovalbumin peptide 323-339, a 17 amino acid peptide known to be a T cell epitope of Ovalbumin protein, was purchased from Bachem Americas Inc. (3132 Kashiwa Street, Torrance Calif. 90505.)

Resiquimod (aka R848) was synthesized according to a method provided in U.S. Pat. No. 6,608,201.

PLA-R848, resiquimod, was conjugated to PLA with a molecular weight of approximately 2,500 Da according to a method provided above.

PLGA-R848, resiquimod, was conjugated to PLGA with a molecular weight of approximately 4,100 Da according to a method provided above.

PS-1826 DNA oligonucleotide with fully phosphorothioated backbone having nucleotide sequence 5'-TCC ATG ACG TTC CTG ACG TT-3' (SEQ ID NO: 1) with a sodium counter-ion was purchased from Oligos Etc (9775 SW Commerce Circle C-6, Wilsonville, Oreg. 97070.)

PO-1826 DNA oligonucleotide with phosphodiester backbone having nucleotide sequence 5'-TCC ATG ACG TTC CTG ACG TT-3' (SEQ ID NO: 2) with a sodium counter-ion was purchased from Oligos Etc. (9775 SW Commerce Circle C-6, Wilsonville, Oreg. 97070.)

PLA with an inherent viscosity of 0.21 dL/g was purchased from SurModics Pharmaceuticals (756 Tom Martin Drive, Birmingham, Ala. 35211. Product Code 100 DL 2A.)

PLA with an inherent viscosity of 0.71 dL/g was purchased from SurModics Pharmaceuticals (756 Tom Martin Drive, Birmingham, Ala. 35211. Product Code 100 DL 7A.)

PLA with an inherent viscosity of 0.19 dL/g was purchased from Boehringer Ingelheim Chemicals, Inc. (Petersburg, Va. Product Code R202H.)

PLA-PEG-nicotine with a molecular weight of approximately 18,500 to 22,000 Da was prepared according to a method provided above.

PLA-PEG-R848 with a molecular weight of approximately 15,000 Da was synthesized was prepared according to a method provided above.

Polyvinyl alcohol (Mw=11,000-31,000, 87-89% hydrolyzed) was purchased from J. T. Baker (Part Number U232-08).

Batches were produced using a double emulsion process with multiple primary emulsions. The table below references the solution suffix (e.g., B in Solution #1 column indicates Solution #1B was used) and volume of solution used.

| Sample Number | Solution #1 (Volume) | Solution #2 (Volume) | Solution #3 (Volume) | Solution #4 (Volume) | Solution #5 (Volume) |
|---|---|---|---|---|---|
| 1 | B (0.1 ml) | C (1.0 ml) | A (0.1 ml) | C (1.0 ml) | A (2.0 ml) |
| 2 | A (0.2 ml) | A (1.0 ml) | A (0.1 ml) | A (1.0 ml) | A (3.0 ml) |
| 3 | A (0.2 ml) | B (1.0 ml) | A (0.1 ml) | B (1.0 ml) | A (3.0 ml) |
| 4 | A (0.2 ml) | B (1.0 ml) | A (0.1 ml) | B (1.0 ml) | A (3.0 ml) |

Solution 1A: Ovalbumin peptide 323-339 @ 35 mg/mL in dilute hydrochloric acid aqueous solution. The solution was prepared by dissolving ovalbumin peptide in 0.13N hydrochloric acid solution at room temperature.

Solution 1B: Ovalbumin peptide 323-339 @ 70 mg/mL in dilute hydrochloric acid aqueous solution. The solution was prepared by dissolving ovalbumin peptide in 0.13N hydrochloric acid solution at room temperature.

Solution 2A: 0.21-IV PLA @ 75 mg/mL and PLA-PEG-nicotine @ 25 mg/ml in methylene chloride. The solution was prepared by first preparing two separate solutions at room temperature: 0.21-IV PLA @ 100 mg/mL in pure methylene chloride and PLA-PEG-nicotine @ 100 mg/mL in pure methylene chloride. The final solution was prepared by adding 3 parts PLA solution for each part of PLA-PEG-nicotine solution.

Solution 2B: 0.71-IV PLA @ 75 mg/mL and PLA-PEG-nicotine @ 25 mg/ml in methylene chloride. The solution was prepared by first preparing two separate solutions at room temperature: 0.71-IV PLA @ 100 mg/mL in pure methylene chloride and PLA-PEG-nicotine @ 100 mg/mL in pure methylene chloride. The final solution was prepared by adding 3 parts PLA solution for each part of PLA-PEG-nicotine solution.

Solution 2C: 0.19-IV PLA @ 75 mg/mL and PLA-PEG-nicotine @ 25 mg/ml in methylene chloride. The solution was prepared by first preparing two separate solutions at room temperature: 0.19-IV PLA @ 100 mg/mL in pure methylene chloride and PLA-PEG-nicotine @ 100 mg/mL in pure methylene chloride. The final solution was prepared by adding 3 parts PLA solution for each part of PLA-PEG-nicotine solution.

Solution 3A: Oligonucleotide (either PS-1826 or PO-1826) @ 200 mg/ml in purified water. The solution was prepared by dissolving oligonucleotide in purified water at room temperature.

Solution 4A: Same as Solution #2A.
Solution 4B: Same as Solution #2B.
Solution 4C: Same as Solution #2C.
Solution 5A: Polyvinyl alcohol @ 50 mg/mL in 100 mM pH 8 phosphate buffer.

Two separate primary water in oil emulsions were prepared. W1/O2 was prepared by combining solution 1 and solution 2 in a small pressure tube and sonicating at 50% amplitude for 40 seconds using a Branson Digital Sonifier 250. W3/O4 was prepared by combining solution 3 and solution 4 in a small pressure tube and sonicating at 50% amplitude for 40 seconds using a Branson Digital Sonifier 250. A third emulsion with two inner emulsion ([W1/O2, W3/O4]/W5) emulsion was prepared by combining 0.5 ml of each primary emulsion (W1/O2 and W3/O4) and solution 5 and sonicating at 30% amplitude for 40 to 60 seconds using the Branson Digital Sonifier 250.

The third emulsion was added to a beaker containing 70 mM phosphate buffer solution (30 mL) and stirred at room temperature for 2 hours to allow for the methylene chloride to evaporate and for the nanocarriers to form. A portion of the nanocarriers were washed by transferring the nanocarrier suspension to a centrifuge tube and spinning at 13,823 g for one hour, removing the supernatant, and re-suspending the pellet in phosphate buffered saline. The washing procedure was repeated and the pellet was re-suspended in phosphate buffered saline for a final nanocarrier dispersion of about 10 mg/mL.

The amounts of oligonucleotide and peptide in the nanocarrier were determined by HPLC analysis.

Example 33: Standard Double Emulsion

Materials

As provided in Example 32 above.

Batches were produced using a standard double emulsion process. The table below references the solution suffix (e.g., B in Solution #1 column indicates Solution #1B was used) and volume of solution used.

| Sample Number | Solution #1 (Volume) | Solution #2 (Volume) | Solution #3 (Volume) | Solution #4 (Volume) | Solution #5 (Volume) |
|---|---|---|---|---|---|
| 1 | A (0.1 ml) | A (0.75 ml) | A (0.25 ml) | None | A (2.0 ml) |
| 2 | A (0.1 ml) | None | A (0.25 ml) | A (0.75 ml) | A (2.0 ml) |
| 3 | A (0.1 ml) | B (0.75 ml) | A (0.25 ml) | None | A (2.0 ml) |
| 4 | B (0.1 ml) | C (0.75 ml) | A (0.25 ml) | None | B (2.0 ml) |
| 5 | B (0.1 ml) | D (0.25 ml) | A (0.25 ml) | A (0.50 ml) | B (2.0 ml) |
| 6 | C (0.2 ml) | None | A (0.25 ml) | A (0.75 ml) | B (2.0 ml) |
| 7 | D (0.1 ml) | None | A (0.25 ml) | A (0.75 ml) | B (2.0 ml) |

Solution 1A: Ovalbumin peptide 323-339 @ 69 mg/mL in de-ionized water. The solution was prepared by slowly adding ovalbumin peptide to the water while mixing at room temperature.

Solution 1B: Ovalbumin peptide 323-339 @ 70 mg/mL in dilute hydrochloric acid aqueous solution. The solution was prepared by dissolving ovalbumin peptide in 0.13N hydrochloric acid solution at room temperature.

Solution 1C: Oligonucleotide (PS-1826) @ 50 mg/ml in purified water. The solution was prepared by dissolving oligonucleotide in purified water at room temperature.

Solution 1D: Ovalbumin peptide 323-339 @ 17.5 mg/mL in dilute hydrochloric acid aqueous solution. The solution was prepared by dissolving ovalbumin peptide @ 70 mg/ml in 0.13N hydrochloric acid solution at room temperature and then diluting the solution with 3 parts purified water per one part of starting solution.

Solution 2A: R848 @ 10 mg/ml and 0.19-IV PLA @ 100 mg/mL in pure methylene chloride prepared at room temperature.

Solution 2B: PLA-R848 @ 100 mg/ml in pure methylene chloride prepared at room temperature.

Solution 2C: PLGA-R848 @ 100 mg/ml in pure methylene chloride prepared at room temperature.

Solution 2D: PLA-PEG-R848 @ 100 mg/ml in pure methylene chloride prepared at room temperature.

Solution 3A: PLA-PEG-nicotine @ 100 mg/ml in pure methylene chloride prepared at room temperature.

Solution 4A: 0.19-IV PLA @ 100 mg/mL in pure methylene chloride prepared at room temperature.

Solution 5A: Polyvinyl alcohol @ 50 mg/mL in de-ionized water.

Solution 5B: Polyvinyl alcohol @ 50 mg/mL in 100 mM pH 8 phosphate buffer.

The water in oil (W/O) primary emulsion was prepared by combining solution 1 and solution 2, solution 3, and solution 4 in a small pressure tube and sonicating at 50% amplitude for 40 seconds using a Branson Digital Sonifier 250. The water/oil/water (W/O/W) double emulsion was prepared by adding solution 5 to the primary emulsion and sonicating at 30% to 35% amplitude for 40 seconds using the Branson Digital Sonifier 250.

The double emulsion was added to a beaker containing phosphate buffer solution (30 mL) and stirred at room temperature for 2 hours to allow for the methylene chloride to evaporate and for the nanocarriers to form. A portion of the nanocarriers were washed by transferring the nanocarrier suspension to a centrifuge tube and spinning at 5,000 to 9,500 RPM for one hour, removing the supernatant, and re-suspending the pellet in phosphate buffered saline. The washing procedure was repeated and the pellet was re-suspended in phosphate buffered saline for a final nanocarrier dispersion of about 10 mg/mL.

Example 34: Determination of Amount of Agents

Method for R848 and Peptides (e.g., Ova Peptide, Human Peptide, TT2pDT5t)

The amount of R848 (immunostimulatory agent) and ova peptide (T cell antigen) was measured using reverse phase HPLC on an Agilent 1100 system at appropriate wavelengths ($\lambda$=254 nm for R848 and 215 nm for ova peptide) equipped with an Agilent Zorbax SB-C18 column (3.5 µm. 75×4.6 mm. Column Temp=40° C. (part no. 866953-902)) using Mobile Phase A (MPA) of 95% water/5% acetonitrile/0.1% TFA and Mobile Phase B (MPB) of 90% acetonitrile/10% water/0.09% TFA (Gradient: B=5 to 45% in 7 minutes; ramp to 95% B to 9 min; decrease back to 5% B to 9.5 min and kept equilibrating to end. Total run time was 13 minute with flow rate of 1 mL/min).

Method for CpG

The amount of CpG (immunostimulatory agent) was measured using reverse phase HPLC on Agilent 1100 system at 260 nm equipped with Waters XBridge C-18 (2.5 micron particle, 50×4.6 mm ID (part No. 186003090), column temp. 600C) using mobile phase A of 2% acetonitrile in 100 mM TEA-acetic acid buffer, pH about 8.0 and mobile B as 90% acetonitrile, 10% water (column equilibrated at 5% B, increased to 55% B in 8.5 min, then ramped to 90% B to 12 minutes. Strength of B was rapidly decreased to 5% in one minute and equilibrated until stop time, 16 minutes. The flow rate was 1 mL/min until end of the method, 16 minutes).

Method for Nicotine Analog

Nicotine analog was measured using reverse phase HPLC on Agilent 1100 system at 254 nm equipped with Waters X-Bridge C-18 (5 micron particle, 100×4.6 mm ID, column temp at 400 C) using Mobile Phase A (MPA) of 95% water/5% acetonitrile/0.1% TFA and Mobile Phase B (MPB) of 90% acetonitrile/10% water/0.09% TFA (gradient: column was equilibrated at 5% B increased to 45% B in 14 minutes. Then ramped up to 95% B from 14 to 20 minutes. Mobile B strength was quickly decreased back to 5% and requilibrated until the end of the method. The flow rate of the method was maintained at 0.5 ml/min with total run time of 25 minutes. The NC suspension was centrifuged @ 14000 rpm for about 15-30 minutes depending on particle size. The collected pellets were treated with 200 uL of conc. NH₄OH (8 M) for 2 h with agitation until the solution turns clear. A 200 uL of 1% TFA was added to neutralize the mixture solution, which brought the total volume of the pellet solution to 200 uL. An aliquot of 50 uL of the solution was diluted with MPA (or water) to 200 uL and analyzed on HPLC as above to determine the amount present in the pellets.

Encapsulated Free R848 in Nanocarrier 0.5 mL of the NC suspension was centrifuged @ 14000 rpm for about 15 minutes. The collected pellet was dissolved with 0.3 mL of acetonitrile and centrifuged briefly @ 14000 rpm to remove any residual insolubles. The clear solution was further diluted with 4 times equivalent volume of MPA and assayed on reverse phase HPLC described above.

Encapsulated CpG in Nanocarrier 330 uL of NC suspension from the manufacture (about 10 mg/mL suspension in PBS) was spun down at 14000 rpm for 15 to 30 minutes depending on particle size. The collected pellets were re-suspended with 500 uL of water and sonicated for 30 minutes to fully disperse the particles. The NC was then heated at 600° C. for 10 minutes. Additional 200 uL of 1 N NaOH was added to the mixture, heated for another 5 minutes where the mixture becomes clear. The hydrolyzed NC solution was centrifuged briefly at 14000 rpm. A final 2× dilution of the clear solution using water was then made and assayed on the reverse HPLC described above.

Encapsulated T Cell Antigens (e.g., Ova Peptide, or Human Peptide, TT2pDT5t)

330 uL of NC suspension from the manufacture (about 10 mg/mL suspension in PBS) was spun down at 14000 rpm for 15 to 30 minutes. 100 uL of acetonitrile was added to the pellets to dissolve the polymer components of the NC. The mixture was vortexed and sonicated for 1 to 5 minutes. 100 uL 0.2% TFA was added to the mixture to extract the peptides and sonicated for another 5 minutes to ensure the break down of the aggregates. The mixture was centrifuged at 14000 rpm for 15 minutes to separate any insoluble materials (e.g., polymers). A 50 uL aliquot of the supernatant diluted with 150 uL of MPA (or water) was taken and assayed on the reverse phase HPLC as described above.

Amount of Conjugated Nicotine Analog (B Cell Antigen) in Nanocarriers 1.5 mL of NC suspension was spun down @ 14000 rpm for about 15 minutes, the pellets were hydrolyzed using 150 uL of concentrated NH₄OH (8M) for about 2-3 h until the solution turns clear. A 150 uL of 2% TFA(aq) solution was added to the pellet mixture to neutralize the solution. A 100 uL aliquot of the mixture was diluted with 200 uL of water and assayed on reverse phase HPLC described above and quantified based on the standard curve established using the precursor (PEG-nicotine) of the PLA-PEG-nicotine used in the manufacture.

Example 35: Release Rate of Immunomodulatory Agent from Synthetic Nanocarriers

The following data show the rates of release of R-848 from nanoparticles made from the low molecular weight polylactic acid-R-848 conjugate shown above. Table 1 provides relevant formulation information for the experiments.

The release of T-cell antigen, ova peptide and adjuvant, R848 from the synthetic nanocarrier (nanoparticles) in PBS (100 mM, pH=7.4) and Citrate buffer (100 mM, pH=4.5) at 37° C. were performed as follows:

Analytical Method: The amount of R848 and ova peptide released is measured using reverse phase HPLC on a Agilent 1100 system at λ=215 nm equipped with an Agilent Zorbax SB-C18 column (3.5 μm. 75×4.6 mm. Column Temp=40° C. (part no. 866953-902)) using Mobile Phase A (MPA) of 98% water/2% acetonitrile/0.1% TFA and Mobile Phase B (MPB) of 90% acetonitrile/10% water/0.09% TFA with Gradient: B=5 to 45% in 7 minutes; ramp to 95% B to 9 min; re-EQ to end. 13 minute run time. Flow=1 mL/min.

The total amount of R848 and ova peptide present in the nanoparticles was as shown in Table 1. An aqueous suspension of the tested synthetic nanocarriers was then diluted to a final stock volume of 4.4 mL with PBS.

(A) In Vitro Release Rate Measurement in PBS (pH=7.4):

For T0 sample, a 200 μL aliquot was immediately removed from each of the NP sample and centrifuged @ 14000 rpm in a microcentrifuge tubes using a Microcentrifuge (Model: Galaxy 16). 100 μL of supernatant was removed and diluted to 200 μL in HPLC Mobile Phase A (MPA) and assayed for the amount of R848 and ova peptide released on the reverse phase HPLC.

For time point measurements: 9×200 μL of each of the samples were added to microcentrifuge tubes (3×200 for unconjugated) and 300 μL of 37 C PBS was added to each above aliquot and the samples were placed immediately in 37° C. oven. At the following time points: 24 hr, 48 hr, 96 hr and 144 hr (for conjugated R848) or 2 h, 16 h and 24 h (for unconjugated (encapsulated) R848), the samples were centrifuged and assayed for the amount of R848 and ova peptide released as above for T0 sample.

(B) In Vitro Release Rate Measurement in Citrate Buffer (pH=4.5):

For T0 sample, a 200 μL aliquot was removed from each of the samples and centrifuged @ 6000 rpm for 20 minutes and the supernatant was removed. The residue nanoparticles was resuspended in 200 uL of citrate buffer and centrifuged @ 14000 rpm for 15 minutes. 100 uL of the supernatant was removed and diluted to 200 uL with MPA and assayed for R848 and peptide as above.

For time point measurements: 9×200 uL of each of the samples were added to microcentrifuge tubes (3×200 for unconjugated) and centrifuged for 20 minutes @ 6000 rpm and the supernatants were removed. The residue NPs were then resuspended in 500 uL of citrate buffer and placed in 37° C. oven. At the following time points: 24 hr, 48 hr, 96 hr and 144 hr (for conjugated R848) or 2 h, 16 h and 24 h (for unconjugated (encapsulated) R848), the samples were centrifuged and assayed for the amount of R848 and ova peptide released as above for T0 sample.

In order to complete the mass balance from above measurements in PBS and Citrate buffer, the remaining pellets (conjugated R848 samples only) from each sample was treated with 200 uL of conc. NH4OH (8 M) for 3 h with mixing. After the mixture was settled, 200 uL of 1% TFA was added to bring total volume of the pellet to 400 uL. An aliquot of 50 uL of the solution was diluted with MPA to 200 uL and analyzed on HPLC as above to determine the amount of R848 and ova peptide that remained in the pellet after in vitro release to close the mass balance. For unconjugated samples, the sample was diluted with TFA in acetonitrile and assayed as above for R848 and peptide.

Figure 2:
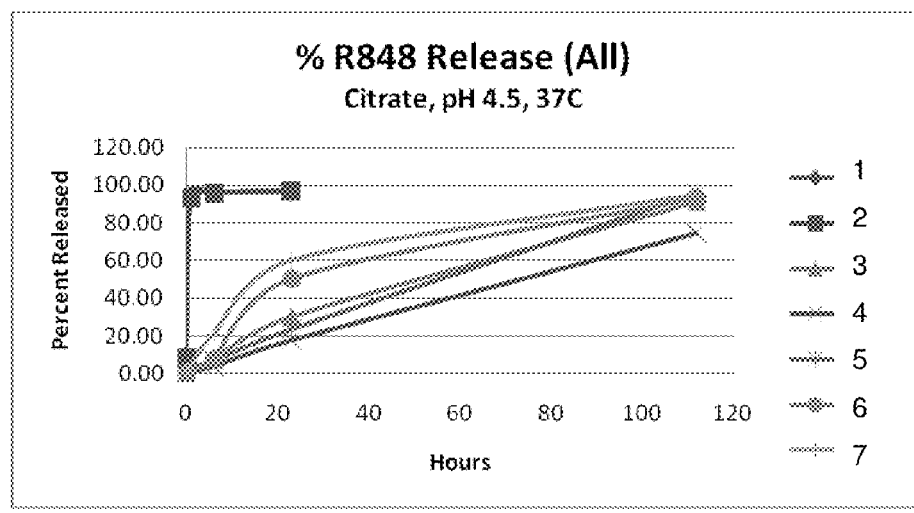
FIG. 2 shows the release of R848 from synthetic nanocarrier formulations at pH 4.5, 37° C.
Figure 3:
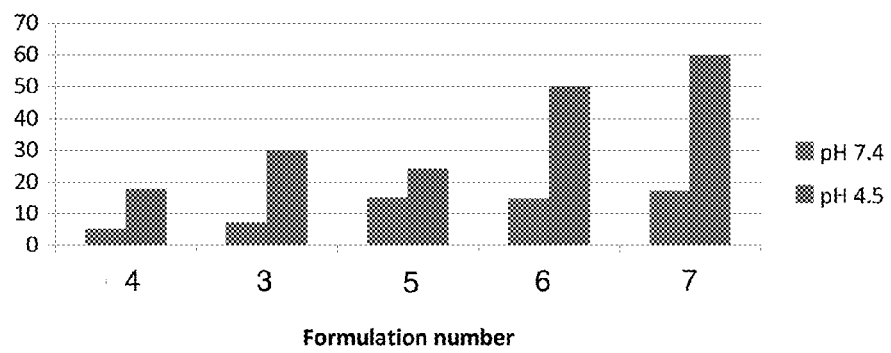
FIG. 3 shows the release of R848 from synthetic nanocarrier formulations at pH 7.4 and pH 4.5 at 24 hours.

The results are summarized in FIGS. 1-3.

TABLE 1

Formulation Targets With A Covalent R848

| For-mula-tion | R848 load* | Ova peptide load | PLA-PEG-NIC | PLA-R848 conju-gate type** | PLA (15-20K, BI R202H) | Chem-istry |
|---|---|---|---|---|---|---|
| 1 | E1.5% | 1.1-2.2% | 25% | | 75% | |
| 2 | E1.5%++ | 1.1-2.2% | 25% | | 75% | |
| 3 | C75% | 0.15-0.31% | 25% | Method 1 | | Amine |
| 4 | C75% | 0.15-0.31% | 25% | Method 1 | | Amine |
| 5 | C75% | 0.15-0.31% | 25% | Method 5 | | ROP-hi MW |
| 6 | C75% | 0.15-0.31% | 25% | Method 5 | | ROP-lo MW |
| 7 | C50% | 0.15-0.31% | 25% | Method 5 | 25% | ROP-lo MW |
| 8 | C25% | 0.15-0.31% | 25% | Method 5 | 50% | ROP-lo MW |

*C = covalent R848; E = encapsulation of R848

Materials and Method—
HPLC—Agilent 1100. λ=215 nm. Column Temp=40° C.
Column—Agilent Zorbax SB-C18, 3.5 μm. 75×4.6 mm. (part no. 866953-902) C18 guard column
Mobile Phase A (MPA)—98% water/2% acetonitrile/0.1% TFA
Mobile Phase B (MPB)—90% acetonitrile/10% water/0.09% TFA
Gradient: B=5 to 45% in 7 minutes; ramp to 95% B to 9 min; re-EQ to end. 13 minute run time. Flow=1 mL/min.
PBS—100 mM, pH=7.4.
Citrate Buffer—100 mM, pH=4.5.
Oven—
Microcentrifuge—Galaxy 16
Microcentrifuge tubes
Sonicator
Pipets—20, 200, 1000 μL adjustable
HPLC grade water—EMD-#WX0008-1.
$NH_4OH$—~8M. Mallinkcrodt.
TFA, 0.2%. Prep 4/27/09.
TFA, 1%. Prep 5/13/09.
Thermometer
Samples—
"6-1" and "6-2" have entrapped R848. All of the rest have conjugated R848.

The estimated values are based on the loading results from the "62" series.

TABLE 2

Estimated R848 and Ova peptide in synthetic nanocarriers:

| Sample ID | Estimated R848 in NPs (μg/mL) | Estimated Ova in NPs (μg/mL) |
|---|---|---|
| 1 | 54 | 146 |
| 2 | 166 | 184 |
| 3 | 119 | 32 |
| 4 | 114 | 34 |
| 5 | 465 | 37 |
| 6 | 315 | 34 |
| 7 | 116 | 40 |

Sample volumes were slightly below what was planned. To ensure enough material is available for all time points, the following volumes of PBS were added to the samples to bring them all to 4.4 mL.

TABLE 3

| Sample ID | Sample Volume (mL) | Volume PBS added (mL) |
|---|---|---|
| 1 | 4.35 | 0.05 |
| 2 | 4.23 | 0.17 |
| 3 | 4.21 | 0.19 |
| 4 | 4.20 | 0.20 |
| 5 | 4.21 | 0.19 |
| 6 | 4.19 | 0.21 |
| 7 | 4.20 | 0.20 |

Procedure—
1) T=0 Sample Prep
   a. PBS
      i. Remove a 200 μL aliquot from each of the samples. Microcentrifuge @ 14000 rpm. Remove supernatant.
      ii. Dilute supernatant 100 μL>200 μL in MPA. (DF=2).
      iii. Assay for peptide and R848.
   b. Citrate
      i. Remove a 200 μL aliquot from each of the samples. Microcentrifuge @ 6000 rpm for 20 minutes. Remove supernatant.
      ii. Add 200 uL of citrate buffer and thoroughly resuspend.
      iii. Microcentrifuge @ 14000 rpm for 15 minutes. Remove supernatant.
      iv. Dilute supernatant 100 μL >200 μL in MPA. (DF=2)
      v. Assay for peptide and R848.
2) PBS IVR
   a. Add 9×200 μL of each of the samples to microcentrifuge tubes. (3×200 for unconjugated)
   b. To each aliquot add 300 μL of 37 C PBS.
   c. Immediately place samples in 37 C oven.
3) Citrate IVR
   a. Add 9×200 uL of each of the samples to microcentrifuge tubes. (3×200 for unconjugated)
   b. Centrifuge for 20 minutes @ 6000 rpm.
   c. Remove the supernatants.
   d. To each tube, add 500 μL of citrate buffer and resuspend thoroughly.
   e. Place samples in 37 C oven
4) For lots 1-4 and 8, remove the samples (see step 6) at the following time points:
   a. Conjugated
      i. 24 hr
      ii. 48 hr (2 days)
      iii. 96 hr (4 days)
      iv. 144 hr (6 days)
      v. Further time points TBD based on the above data.

b. Non conjugated
  i. 2 hr
  ii. 16 hr
  iii. 24 hr
5) For lots 6 and 7, remove samples at the following time points:
  a. PBS
    i. 24 hr
    ii. 48 hr (2 days)
    iii. 96 hr (4 days)
    iv. 144 hr (6 days)
    v. Further time points TBD based on the above data.
  b. Citrate
    i. 2 hr
    ii. 16 hr
    iii. 24 hr
    iv. 48 hr (2 days)
    v. 72 hr (3 days)
    vi. 96 hr (4 days)
    vii. 120 hr (5 days)
    viii. Further time points TBD based on the above data.
6) Sample as follows:
  a. Microcentrifuge @ 14000 rpm for 15 minutes.
  b. Remove supernatant.
  c. Dilute 100 μL to 200 μL in MPA. (DF=2)
7) Assay for peptide and R848. This will provide the amount released at each time point.
To Complete Mass Balance, Perform the Following:
8) To the remaining pellets (conjugated only) add 200 uL NH$_4$OH.
9) Vortex briefly and sonicate to disperse.
10) Add stir bar. Allow to sit until clear (at least 3 hours).
11) Add 200 uL of 1% TFA (total pellet volume=400 μL).
12) Dilute 50 μL to 200 μL in MPA. Analyze by HPLC to determine peptide and R848 remaining in the pellet. (DF=4).
13) For unconjugated lots, assay for peptide and R848 with typical AcN/TFA method.

Example 36: Release Rate Testing

The release of antigen (e.g., ova peptide, T cell antigen) and immunostimulatory agents (e.g., R848, CpG) from synthetic nanocarriers in phosphate buffered saline solution (PBS) (100 mM, pH=7.4) and citrate buffer (100 mM, pH=4.5) at 37° C. was determined as follows:

The release of R848 from the nanocarrier composed of conjugated R848 and the ova peptide was achieved by exchanging desired amount of the aqueous suspension of the tested synthetic nanocarriers obtained from the manufacture (e.g., about 10 mg/mL in PBS) into the same volume of the appropriate release media (Citrate buffer 100 mM) via centrifugation and re-suspension.

In Vitro Release Rate Measurement in PBS (pH=7.4)

1 mL of the PBS suspension NC was centrifuged @ 14000 rpm in microcentrifuge tubes generally from 15-30 minutes depending on particle size. The collected supernatant was then diluted with equal volume of the mobile phase A (MPA) or water and assayed on reverse phase HPLC for the amount of the R848 release during the storage. The remaining pellet was re-suspended to homogeneous suspension in 1 mL of PBS and placed to 37° C. thermal chamber with constant gentle agitation For T0 sample, a 150 μL aliquot was immediately removed from NC suspension prior placing the NC suspension to 37° C. thermal chamber and centrifuged @ 14000 rpm in microcentrifuge tubes using a microcentrifuge (Model: Galaxy 16). 100 μL of the supernatant was removed and diluted to 200 μL with HPLC Mobile Phase A (MPA) or water and assayed for the amount of R848 and ova peptide released on the reverse phase HPLC.

For time point measurements, 150 μL aliquot was removed from the 37° C. NC sample suspension, and the samples were centrifuged and assayed for the amount of R848 and ova peptide released in the same manner as for T0 sample. The R848 and ova peptide released was tested at 6 h, 24 h for routine monitoring with additional 2 h, 48 h, 96 h and 144 h for complete release profile establishment.

In Vitro Release Rate Measurement in Citrate Buffer (pH=4.5)

A 100 mM sodium citrate buffer (pH=4.5) was applied to exchange the original NC storage solution (e.g., PBS) instead of the PBS buffer, pH=7.4. In order to complete the mass balance from above measurements in PBS and Citrate buffer, the remaining pellets from each time point were treated with 100 uL of NH$_4$OH (8 M) for 2 h (or more) with agitation until solution turn clear. A 100 uL of 1% TFA was added to neutralize the mixture, which brought the total volume of the pellet solution to 200 uL. An aliquot of 50 uL of the mixture was diluted with MPA (or water) to 200 uL and analyzed on HPLC as above to determine the amount of unreleased R848 remaining in the pellets after in vitro release to close the mass balance. For unconjugated samples, the sample was diluted with TFA in acetonitrile and assayed as above for R848.

The release of CpG was determined similar to the measurement of R848 and ova peptide in terms of sample preparation and monitored time points. However, the amount of the CpG in the release media was assayed by the reverse phase HPLC method described above.

Example 37: Immunization with NC-Nic Carrying CpG Adjuvant

Groups of five mice were immunized three times (subcutaneously, hind limbs) at 2-week intervals (days 0, 14 and 28) with 100 μg of NC-Nic. NC-Nic was a composition of nanocarriers exhibiting nicotine on the outer surface and, for all groups of mice except for Group 1, carrying CpG-1826 (thioated) adjuvant, which was released from the nanocarriers at different rates. The nanocarriers were prepared according to a method provided above. Serum anti-nicotine antibodies were then measured on days 26 and 40. $EC_{50}$ for anti-nicotine antibodies as measured in standard ELISA against polylysine-nicotine are shown in FIG. 4.

The Group 1 mice were administered NC-Nic w/o CpG-1826 containing Ova peptide and polymers, 75% of which were PLA and 25% were PLA-PEG-Nic. The Group 2 mice were administered NC-Nic containing ova peptide, polymers, 75% of which were PLA and 25% were PLA-PEG-Nic, and 3.2% CpG-1826; release rate at 24 hours: 4.2 μg CpG per mg of NC. The Group 3 mice were administered NC-Nic containing polymers, 75% of which were PLA and 25% were PLA-PEG-Nic, and 3.1% CpG-1826; release rate at 24 hours: 15 µg CpG per mg of NC. Release was determined at a pH of 4.5.

Figure 4:
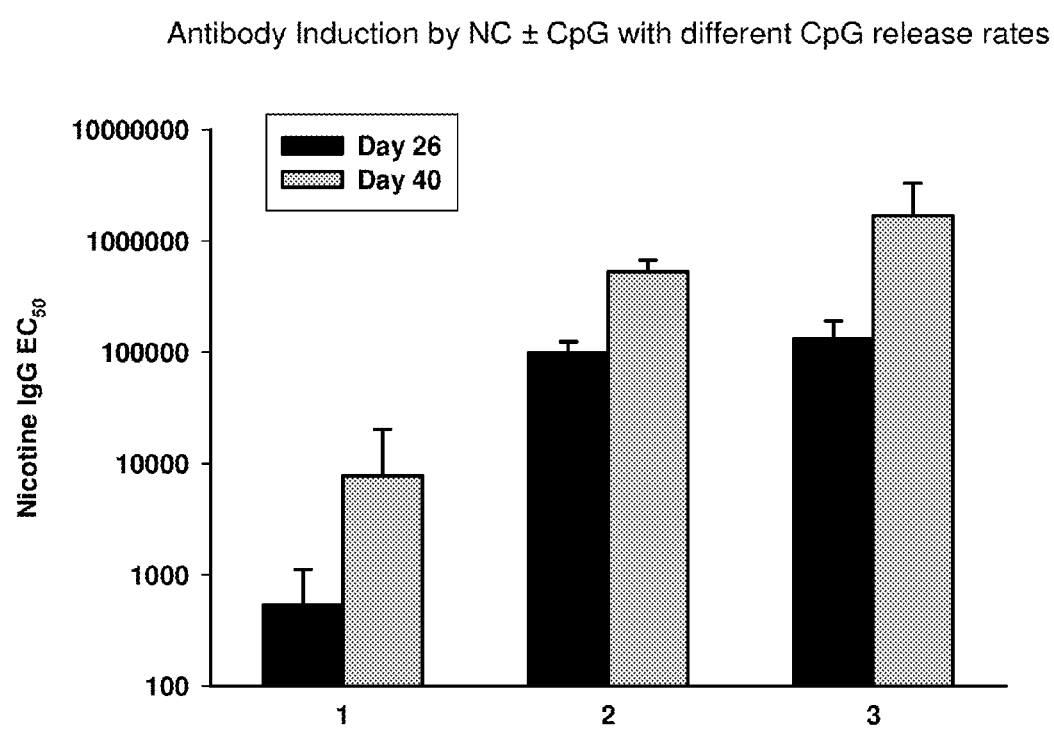
FIG. 4 shows the level of antibody induction by synthetic nanocarriers with a CpG-containing immunostimulatory nucleic acid (Groups 2 and 3) as compared to the level of antibody induction by synthetic nanocarriers without the CpG-containing immunostimulatory nucleic acid (Group 1).

The results shown in FIG. 4 demonstrate that entrapment of adjuvant into nanocarriers is beneficial for the immune response against NC-associated antigen, and, furthermore, that the higher release rate of entrapped CpG adjuvant from within the nanocarriers (NC) at 24 hours produced an immune response, which was elevated compared to one induced by NC with a slower release rate of CpG adjuvant (a TLR9 agonist).

Example 38: Immunization with NC-Nic Carrying Two Forms of CpG Adjuvant

Groups of five mice were immunized two times (subcutaneously, hind limbs) at 4-week intervals (days 0, and 28) with 100 µg of NC-Nic and serum anti-nicotine antibodies were then measured on days 12, 24 and 40. NC-Nic was a composition of nanocarriers exhibiting nicotine on the outer surface and carrying one of two forms of CpG-1826 adjuvant. The nanocarriers were prepared according to a method provided above. $EC_{50}$ for anti-nicotine antibodies as measured in standard ELISA against polylysine-nicotine are shown in FIG. 5.

The Group 1 mice were administered NC-Nic containing ova peptide, polymers, 75% of which were PLA and 25% were PLA-PEG-Nic, and 6.2% CpG-1826 (thioated); release rate at 24 hours: 16.6 µg CpG per mg of NC. The Group 2 mice were administered NC-Nic containing ova peptide, polymers, 75% of which were PLA and 25% were PLA-PEG-Nic, and 7.2% CpG-1826 (thioated); release rate at 24 hours: 13.2 µg CpG per mg of NC. The Group 3 mice were administered NC-Nic containing ova peptide, polymers, 75% of which were PLA and 25% were PLA-PEG-Nic, and 7.9% CpG-1826 (phosphodiester or PO, non-thioated); release rate at 24 hours: 19.6 µg CpG per mg of NC. The Group 4 mice were administered NC-Nic containing ova peptide, polymers, 75% of which were PLA and 25% were PLA-PEG-Nic, and 8.5% CpG-1826 (PO, non-thioated); release rate at 24 hours: 9.3 µg CpG per mg of NC. Release was determined at a pH of 4.5.

Figure 5:
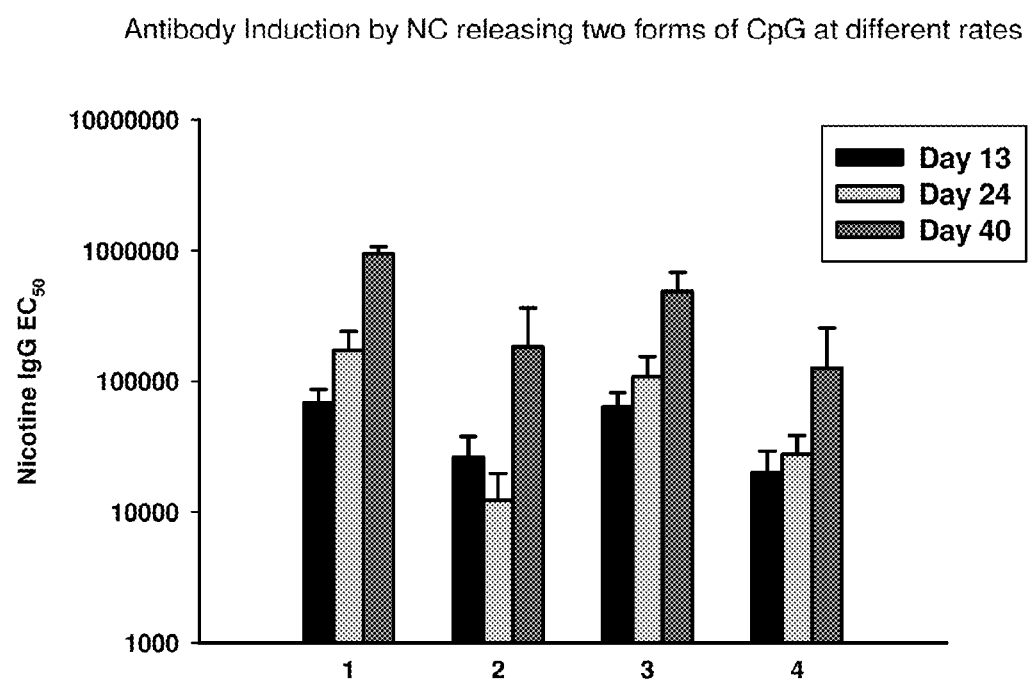
FIG. 5 shows the level of antibody induction by synthetic nanocarriers that release a phosphodiester, non-thioated CpG-containing immunostimulatory nucleic acid or a thioated CpG-containing immunostimulatory nucleic acid.

The results shown in FIG. 5 demonstrate that the rate of release of entrapped adjuvant (CpG, TLR9 agonist) from nanocarriers influenced production of an antibody to NC-bound antigen (nicotine) with the nanocarrier exhibiting higher release rate at 24 hours induced stronger humoral immune response (group 1>group 2 and group 3>group 4). This was true irrespective of CpG form used (more stable, thioated or less stable non-thioated).

Example 39: Immunization with NC-Nic Carrying R848

Groups of five mice were immunized three times (subcutaneously, hind limbs) at 2-week intervals (days 0, 14 and 28) with 100 µg of NC-Nic and serum anti-nicotine antibodies were then measured on days 26, 40 and 54. The nanocarriers were prepared according to a method provided above. $EC_{50}$ for anti-nicotine antibodies as measured in standard ELISA against polylysine-nicotine are shown in FIG. 6.

The Group 1 mice were administered NC-Nic containing ova peptide and polymers, 75% of which were PLA and 25% were PLA-PEG-Nic, but without adjuvant. The Group 2 mice were administered NC-Nic containing ova peptide, polymers, 75% of which were PLA and 25% were PLA-PEG-Nic, and 1.0% R848; of which 92% is released at 2 hours and more than 96% is released at 6 hours. The Group 3 mice were administered NC-Nic containing ova peptide, polymers, 75% of which were PLA-R848 and 25% were PLA-PEG-Nic, and 1.3% R848, of which 29.4% is released at 6 hours and 67.8% is released at 24 hours. The Group 4 mice were administered NC-Nic containing ova peptide, polymers, 75% of which were PLA-R848 and 25% were PLA-PEG-Nic, and 1.4% of R848, of which 20.4% is released at 6 hours and 41.5% is released at 24 hours. The Group 5 mice were administered NC-Nic containing ova peptide, polymers, 25% of which were PLA-PEG-R848, 50% PLA, and 25% were PLA-PEG-Nic, and 0.7% of R848; of which less than 1% is released at 24 hours. Release was determined at a pH of 4.5.

Figure 6:
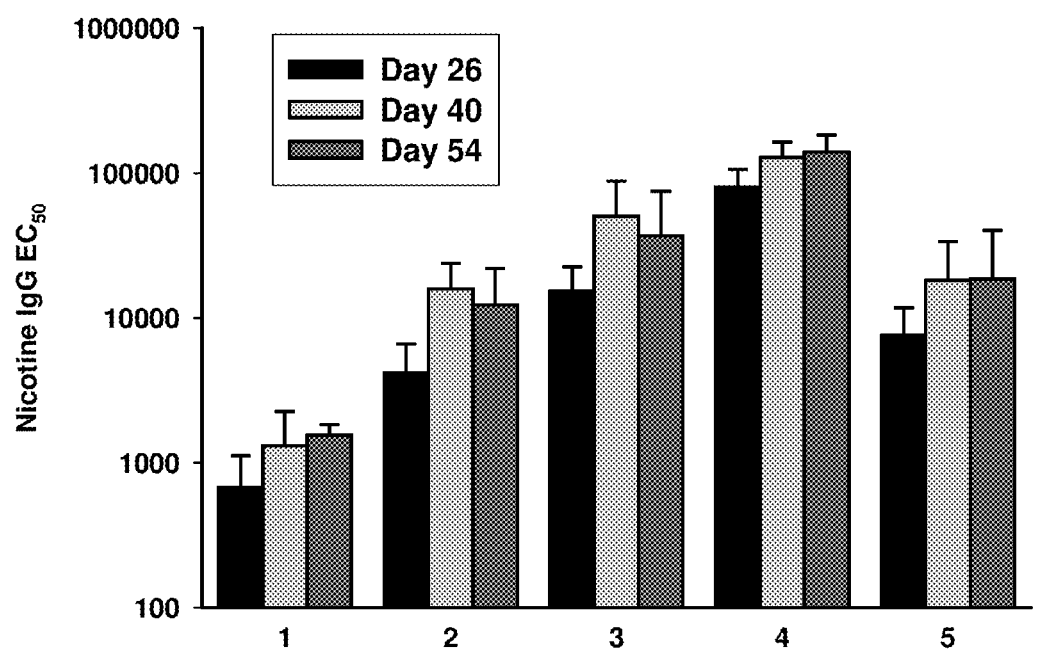
FIG. 6 shows the level of antibody induction by synthetic nanocarriers that release R848 at different rates.

The results shown in FIG. 6 demonstrate that R848 adjuvant (a TLR 7/8 agonist) contained in the NC augments humoral immune response against NC-associated antigen (groups 2-5>>group 1). Furthermore, neither fast (group 2), nor slow (group 5) release of R848 was elevated an immune response to the same level as NC releasing R848 at intermediate rate (group 3≈group 4>group 2≈group 5).

What is claimed is:

1. A compound that comprises a structure as in formula (IV):

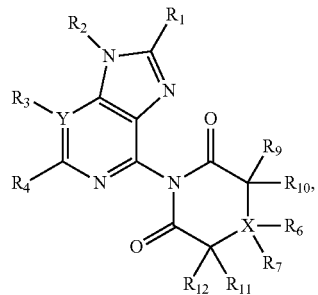

(IV)

wherein $R_1$=H, OH, SH, $NH_2$, or substituted or unsubstituted alkyl, alkoxy, alkylthio, or alkylamino;

$R_2$=H, alkyl, or substituted alkyl;

Y=N or C;

$R_3$ is absent if Y=N; or is H, alkyl, substituted alkyl, or combined with $R_4$ to form a carbocycle or heterocycle with the carbon atoms of the pyridine ring to which they are connected if Y=C;

$R_4$ is H, or substituted or unsubstituted alkyl, alkoxy, alkylthio, or alkylamino when not combined with $R_3$ to form a carbocycle or heterocycle with the carbon atoms of the pyridine ring to which they are connected; or is combined with $R_3$ to form a carbocycle or heterocycle with the carbon atoms of the pyridine ring to which they are connected;

X is C, N, O, or S;

$R_6$ and $R_7$ are each independently H or substituted; and $R_9$, $R_{10}$, $R_{11}$, and $R_{12}$ are each independently H, a halogen, OH, thio, $NH_2$, or substituted or unsubstituted alkyl, aryl, heterocyclic, alkoxy, aryloxy, alkylthio, arylthio, alkylamino, or arylamino.

2. A method for making a compound that comprises a structure as in formula (IV):

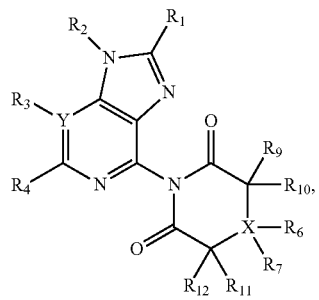

(IV)

comprising:

combining, in the presence of a solvent and/or heat, a compound that comprises a structure as in formula (III):

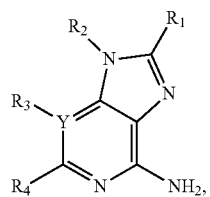

(III)

and a compound comprising a structure as in formula (V):

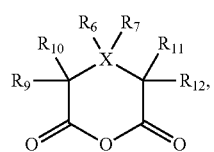

(V)

wherein $R_1$=H, OH, SH, $NH_2$, or substituted or unsubstituted alkyl, alkoxy, alkylthio, or alkylamino;

$R_2$=H, alkyl, or substituted alkyl;

Y=N or C;

$R_3$ is absent if Y=N; or is H, alkyl, substituted alkyl, or combined with $R_4$ to form a carbocycle or heterocycle with the carbon atoms of the pyridine ring to which they are connected if Y=C;

R₄ is H, or substituted or unsubstituted alkyl, alkoxy, alkylthio, or alkylamino when not combined with R₃ to form a carbocycle or heterocycle with the carbon atoms of the pyridine ring to which they are connected; or is combined with R₃ to form a carbocycle or heterocycle with the carbon atoms of the pyridine ring to which they are connected;

X is C, N, O, or S;

R₆ and R₇ are each independently H or substituted; and

R₉, R₁₀, R₁₁, and R₁₂ are each independently H, a halogen, OH, thio, NH₂, or substituted or unsubstituted alkyl, aryl, heterocyclic, alkoxy, aryloxy, alkylthio, arylthio, alkylamino, or arylamino.

3. The compound of claim 1, wherein R₁ is H, R₂ is isobutyl, Y is C, and R₃ and R₄ are combined to form a benzene ring with the carbon atoms of the pyridine ring to which they are connected.

4. The compound of claim 1, wherein R₁ is ethoxymethyl, R₂ is hydroxyisobutyl, Y=C, and R₃ and R₄ are combined to form a benzene ring with the carbon atoms of the pyridine ring to which they are connected.

5. The compound of claim 1, wherein R₁ is ethoxymethyl, R₂ is methanesulfonamidoisobutyl, Y=C, and R₃ and R₄ are combined to form a benzene ring with the carbon atoms of the pyridine ring to which they are connected.

6. The compound of claim 1, wherein R₁ is OH, R₂ is benzyl, Y=N, R₃ is absent, and R₄ is butoxy.

7. The compound of claim 1, wherein Y is N, R₁ is OH, R₂ is benzyl, R₃ is absent, and R₄ is butylamino.

8. The compound of claim 1, wherein Y is N, R₁ is OH, R₂ is benzyl, R₃ is absent, and R₄ is butoxy.

9. The compound of claim 1, wherein Y is N, R₁ is OH, R₂ is benzyl, R₃ is absent, and R₄ is benzylamino.

10. The compound of claim 1, wherein Y is N, R₁ is OH, R₂ is benzyl, R₃ is absent, and R₄ is pentyl.

11. A composition comprising the compound of claim 1.

12. The method of claim 2, wherein R₁ is H, R₂ is isobutyl, Y is C, and R₃ and R₄ are combined to form a benzene ring with the carbon atoms of the pyridine ring to which they are connected.

13. The method of claim 2, wherein R₁ is ethoxymethyl, R₂ is hydroxyisobutyl, Y=C, and R₃ and R₄ are combined to form a benzene ring with the carbon atoms of the pyridine ring to which they are connected.

14. The method of claim 2, wherein R₁ is ethoxymethyl, R₂ is methanesulfonamidoisobutyl, Y=C, and R₃ and R₄ are combined to form a benzene ring with the carbon atoms of the pyridine ring to which they are connected.

15. The method of claim 2, wherein R₁ is OH, R₂ is benzyl, Y=N, R₃ is absent, and R₄ is butoxy.

16. The method of claim 2, wherein Y is N, R₁ is OH, R₂ is benzyl, R₃ is absent, and R₄ is butylamino.

17. The method of claim 2, wherein Y is N, R₁ is OH, R₂ is benzyl, R₃ is absent, and R₄ is butoxy.

18. The method of claim 2, wherein Y is N, R₁ is OH, R₂ is benzyl, R₃ is absent, and R₄ is benzylamino.

19. The method of claim 2, wherein Y is N, R₁ is OH, R₂ is benzyl, R₃ is absent, and R₄ is pentyl.

20. A compound that comprises a structure as in formula (VI):

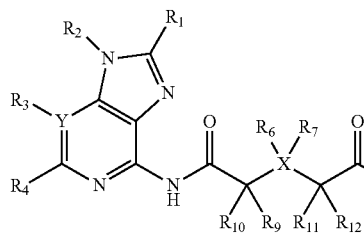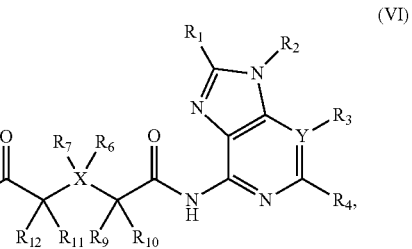

(VI)

wherein R₁=H, OH, SH, NH₂, or substituted or unsubstituted alkyl, alkoxy, alkylthio, or alkylamino;

R₂=H, alkyl, or substituted alkyl;

Y=N or C;

R₃ is absent if Y=N; or is H, alkyl, substituted alkyl, or combined with R₄ to form a carbocycle or heterocycle with the carbon atoms of the pyridine ring to which they are connected if Y=C;

R₄ is H, or substituted or unsubstituted alkyl, alkoxy, alkylthio, or alkylamino when not combined with R₃ to form a carbocycle or heterocycle with the carbon atoms of the pyridine ring to which they are connected; or is combined with R₃ to form a carbocycle or heterocycle with the carbon atoms of the pyridine ring to which they are connected;

X is C, N, O, or S;

R₆ and R₇ are each independently H or substituted;

R₉, R₁₀, R₁₁, and R₁₂ are each independently H, a halogen, OH, thio, NH₂, or substituted or unsubstituted alkyl, aryl, heterocyclic, alkoxy, aryloxy, alkylthio, arylthio, alkylamino, or arylamino; and the polymer is insoluble in water at pH=7.4 and at 25° C.

21. The compound of claim 20, wherein the polymer is selected from the group consisting of polyketaldiols, poly(ethylene)glycol, polycaprolactone diol, diblock polylactide-co-poly(ethylene)glycol, diblock polylactide/polyglycolide-co-poly(ethylene)glycol, diblock polyglycolide-co-poly(ethylene)glycol, poly(propylene) glycol, poly(hexamethylene carbonate)diol, and poly(tetrahydrofuran).

22. The compound of claim 20, wherein the polymer has a weight average molecular weight ranging from 800 Daltons to 10,000 Daltons, as determined using gel permeation chromatography.

23. The compound of claim 20, wherein the polymer does not comprise polyketal or unit thereof.

24. The compound of claim 20, wherein R₁ is H, R₂ is isobutyl, Y is C, and R₃ and R₄ are combined to form a benzene ring with the carbon atoms of the pyridine ring to which they are connected.

25. The compound of claim 20, wherein R₁ is ethoxymethyl, R₂ is hydroxyisobutyl, Y=C, and R₃ and R₄ are combined to form a benzene ring with the carbon atoms of the pyridine ring to which they are connected.

26. The compound of claim 20, wherein R₁ is ethoxymethyl, R₂ is methanesulfonamidoisobutyl, Y=C, and R₃ and $R_4$ are combined to form a benzene ring with the carbon atoms of the pyridine ring to which they are connected.

27. The compound of claim 20, wherein Y=N, $R_1$ is OH, $R_2$ is benzyl, $R_3$ is absent, and $R_4$ is butoxy.

28. The compound of claim 20, wherein Y is N, $R_1$ is OH, $R_2$ is benzyl, $R_3$ is absent, and $R_4$ is butylamino.

29. The compound of claim 20, wherein Y is N, $R_1$ is OH, $R_2$ is benzyl, $R_3$ is absent, and $R_4$ is benzylamino.

30. The compound of claim 20, wherein Y is N, $R_1$ is OH, $R_2$ is benzyl, $R_3$ is absent, and $R_4$ is pentyl.

31. A composition comprising the compound of claim 20.

32. A synthetic nanocarrier that comprises the compound of claim 20.

33. A composition comprising the synthetic nanocarrier of claim 32.

34. A composition comprising a vaccine comprising the compound of claim 20.

35. A composition comprising a vaccine comprising the synthetic nanocarrier of claim 32.

36. A method comprising:
    administering the compound of claim 20 to a subject.

* * * * *